(12) United States Patent
Bu

(10) Patent No.: US 8,198,236 B2
(45) Date of Patent: Jun. 12, 2012

(54) METHODS AND COMPOSITIONS FOR THE TREATMENT OF CANCER

(75) Inventor: Guojun Bu, Chesterfield, MO (US)

(73) Assignee: Washington University, St. Louis, MO (US)

( * ) Notice: Subject to any disclaimer, the term of this patent is extended or adjusted under 35 U.S.C. 154(b) by 5 days.

(21) Appl. No.: 12/598,240

(22) PCT Filed: Apr. 30, 2008

(86) PCT No.: PCT/US2008/062092
§ 371 (c)(1),
(2), (4) Date: Oct. 30, 2009

(87) PCT Pub. No.: WO2008/134752
PCT Pub. Date: Nov. 6, 2008

(65) Prior Publication Data
US 2010/0120685 A1    May 13, 2010

Related U.S. Application Data

(60) Provisional application No. 60/914,902, filed on Apr. 30, 2007.

(51) Int. Cl.
*A61K 38/00* (2006.01)
*A61K 38/08* (2006.01)
(52) U.S. Cl. .......................................... 514/2
(58) Field of Classification Search .................. None
See application file for complete search history.

(56) References Cited

U.S. PATENT DOCUMENTS

| 2003/0166105 A1 | 9/2003 | Baker et al. | |
| 2008/0227698 A1* | 9/2008 | Bu et al. | 514/12 |

FOREIGN PATENT DOCUMENTS

| WO | 01/36440 | 5/2001 |
| WO | WO 01/36440 A1 * | 5/2001 |
| WO | WO 2005/115354 A2 | 12/2005 |
| WO | WO 2007/035716 A2 | 3/2007 |

OTHER PUBLICATIONS

Score sequence search results, Geneseq database, "20110429_075352_us-12-598-240-15.rag" Apr. 29, 2011.*
Li et al. Mesd binds to mature LDL-receptor-related protein-6 and antagonizes ligand binding. J Cell Sci 2005, 118 pp. 5305-5309.
International Search Report issued on Aug. 21, 2009 in connection to related application No. PCT/US08/62092.
Bu et al., Receptor-mediated endocytosis of tissue-type plasminogen activator by low density lipoprotein receptor-related protein on human hepatoma HepG2 cells. J Biol Chem. 1993, 268:13002-13009.

Bu, The roles of receptor-associated protein (RAP) as a molecular chaperone for members of the LDL receptor family, Int. Rev. Cytol. 2001, 209:79-116.
Cong et al., Wnt signals across the plasma membrane to activate the beta-catenin pathway by forming oligomers containing its receptors, Frizzled and LRP, Development 2004, 131(20):5103-15.
Culi, Boca, an endoplasmic reticulum protein required for wingless signaling and trafficking of LDL receptor family members in *Drosophila*, Cell 2003, 112:343-354.
He, LDL receptor-related proteins 5 and 6 in Wnt/beta-catenin signaling: arrows point the way, Development 131:1663-1677, 2004.
Howe and Brown, Wnt signaling and breast cancer. Cancer Biol. Ther. 2004, 3:36-41.
Iadonato, Interaction of a 39 kDa protein with the low-density-lipoprotein-receptor-related protein (LRP) on rat hepatoma cells. Biochem. J. 1993, 296:867 875.
Korinek et al., Constitutive transcriptional activation by a beta-catenin-Tcf complex in APC-/- colon carcinoma. Science 1997, 275:1784 -1787.
Kuhnert et al., Essential requirement for WNT signaling in porliferation of adult small intestine and colon revealed by adenoviral expression of Dickkopf-1, Proc. Nat'l Acad. Sci. USA 2004, 101:266-271.
Li et al, Mesd binds to mature LDL-receptor-related protein-6 and antagonizes ligand binding, J Cell Sci. 2005 118:5305-5314.
Li, Essential role of the low density lipoprotein receptor-related protein in vascular smooth muscle cell migration. FEBS Lett. 2003, 555:346-350.
Li, The YXXL motif, but not the two NPXY motifs, serves as the dominant endocytosis signal for low density lipoprotein receptor-related protein. J. Biol. Chem. 2000, 276:17187 17194.
Li, Differential functions of members of the low density lipoprotein receptor family suggested by their distinct endocytosis rates J. Biol. Chem. 2001, 276:18000-18006.
Li et al., LRP6 expression promotes cancer cell proliferation and tumorigenesis by altering β-catenin subcellular distribution. 2004, Oncogene 23:9129 9135.
Liu et al., The putative tumor suppressor LRP1B, a novel member of the low density lipoprotein (LDL) receptor family, exhibits both overlapping and distinct properties with the LDL receptor-related protein. J. Biol. Chem. 2001, 276:28889-28896.
Liu et al., Mammary stem cells, self-renewal pathways, and carcinogenesis, Breast Cancer Res. 2005, 7:86-95.
Tian et al., The role of the Wnt-signaling antagonist DKK1 in the development of osteolytic lesions in multiple myeloma. New Engl. J. Med. 2003, 349:2483-2494.
Westendorf, Wnt signaling in osteoblasts and bone diseases. Gene 2004, 341:19-39.

* cited by examiner

*Primary Examiner* — Laura B Goddard
(74) *Attorney, Agent, or Firm* — Zackson Law LLC; Saul L. Zackson

(57) ABSTRACT

Oligopeptides which can be used to treat cancer are disclosed. Further disclosed are methods of treating cancer, including breast cancer, skin cancer, prostate cancer and multiple myeloma (MM). These methods include administration of a polypeptide encoded by the Mesd gene, or an oligopeptide comprising a contiguous subsequence of a Mesd polypeptide.

7 Claims, 29 Drawing Sheets

FIG. 1
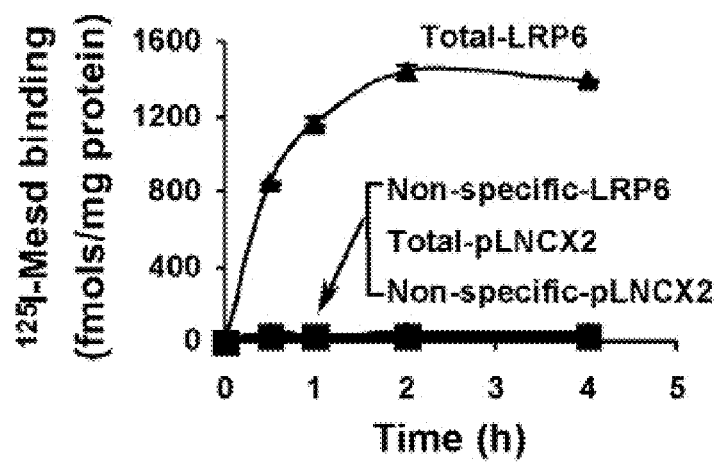
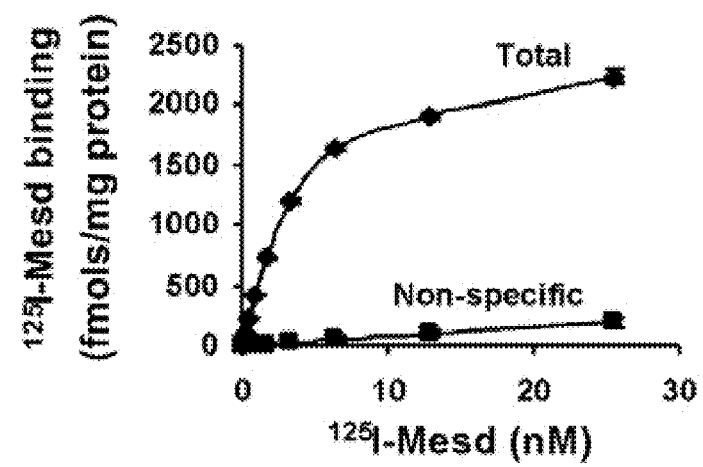
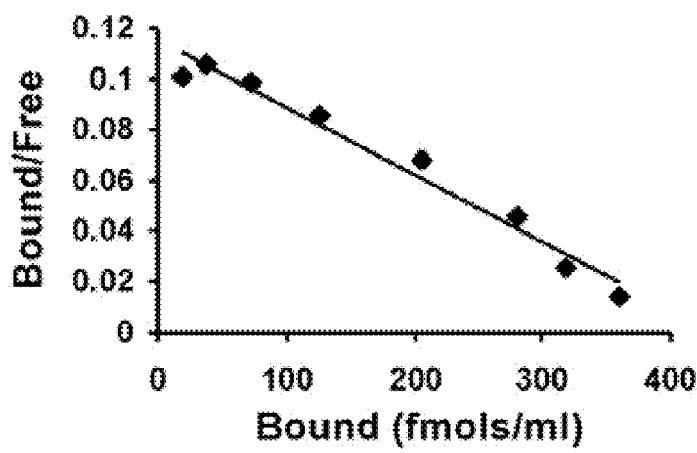

FIG. 8
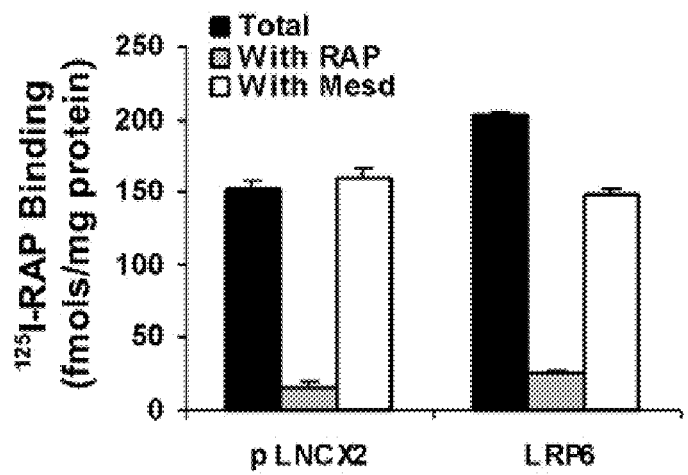
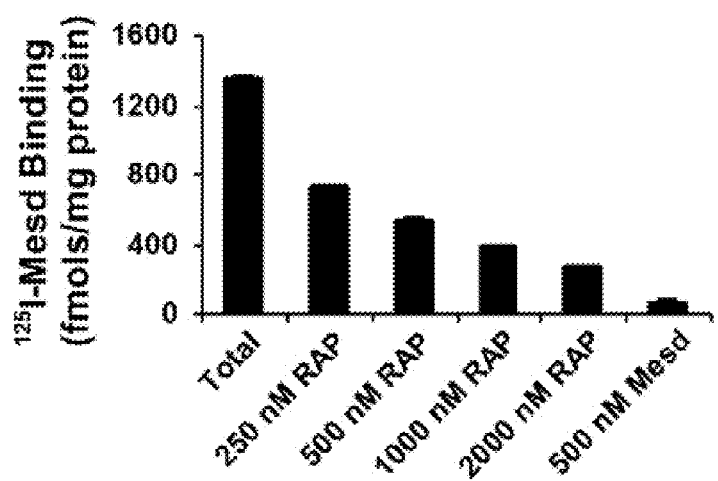
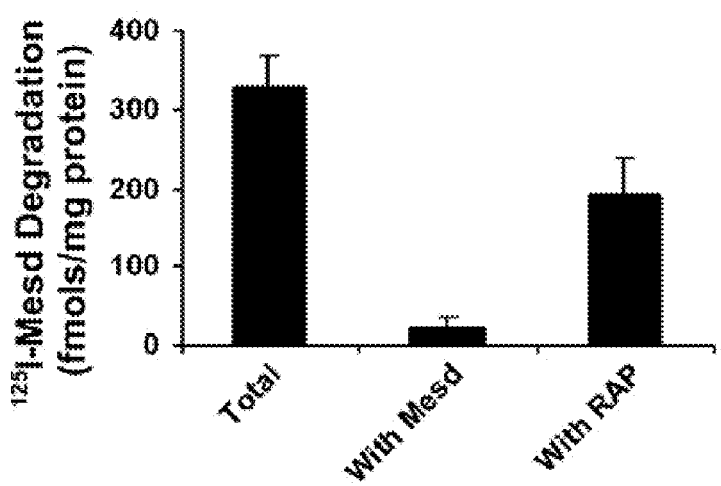

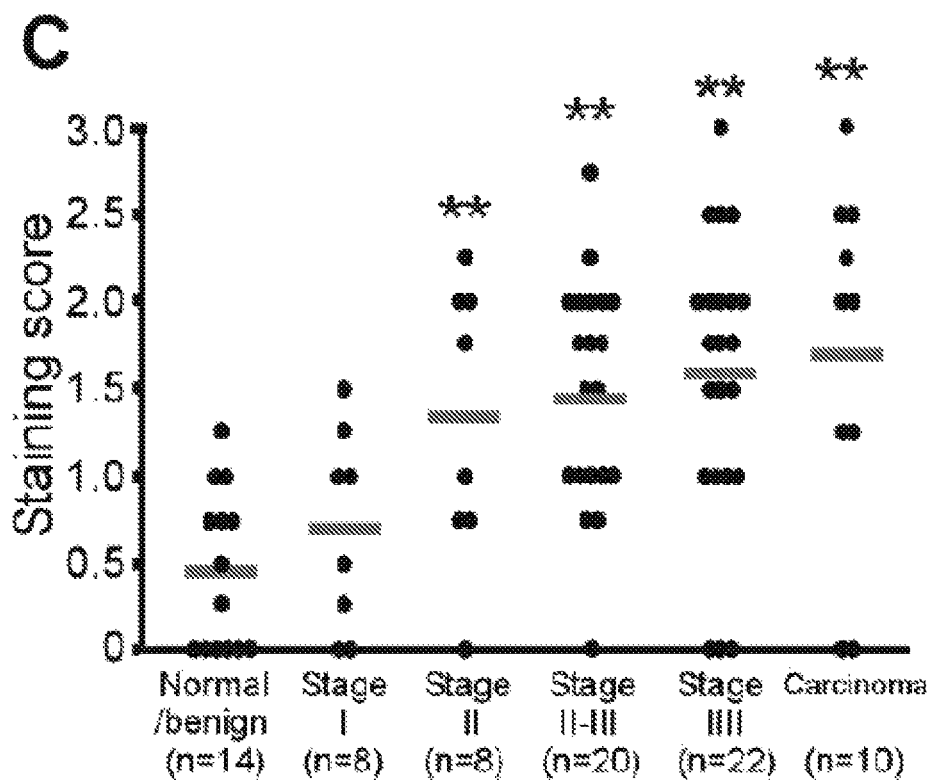
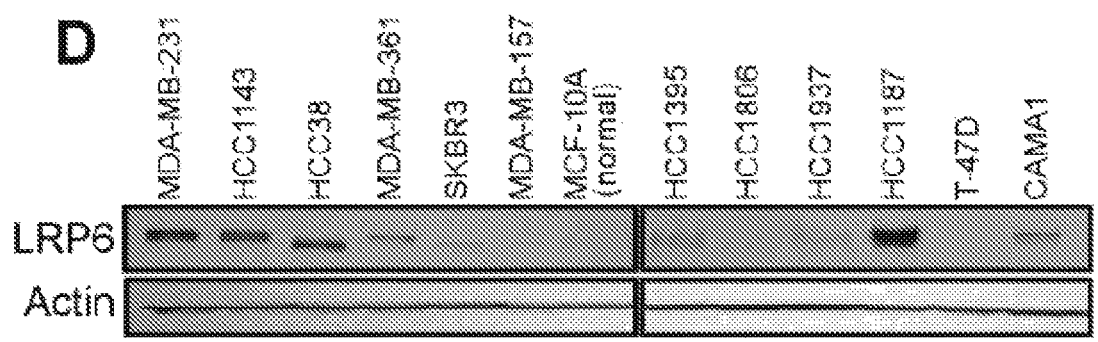
FIG. 13 Continued

FIG. 15
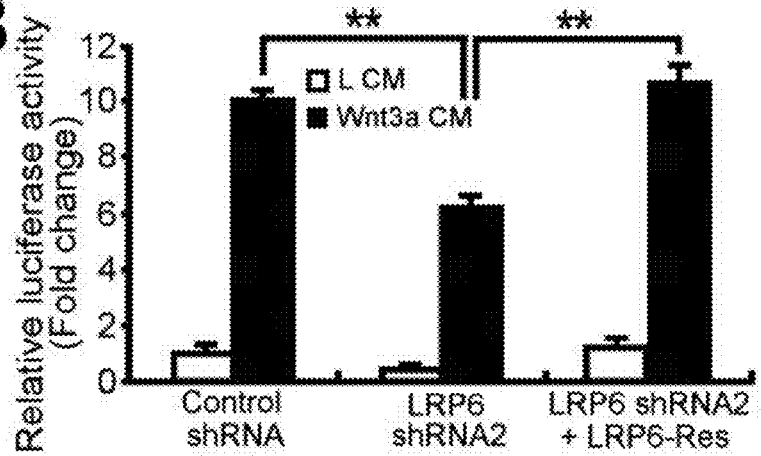
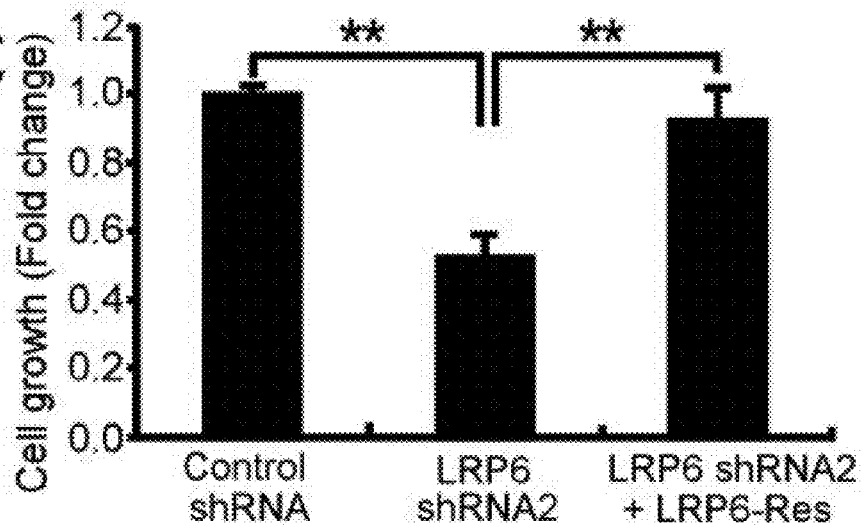

FIG. 15 Continued
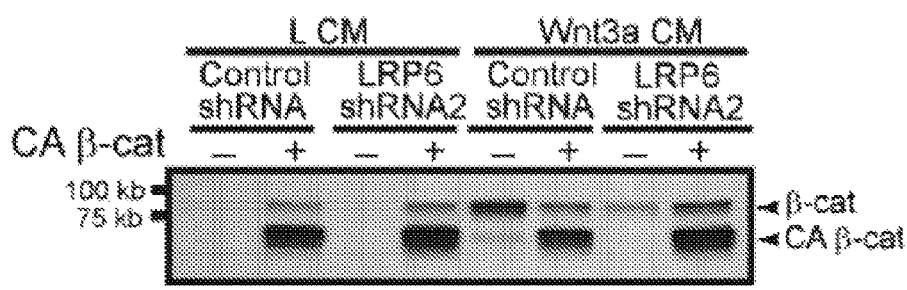
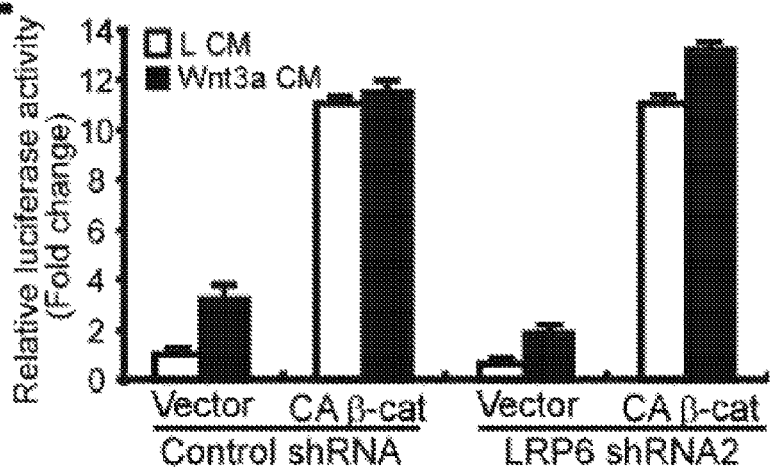
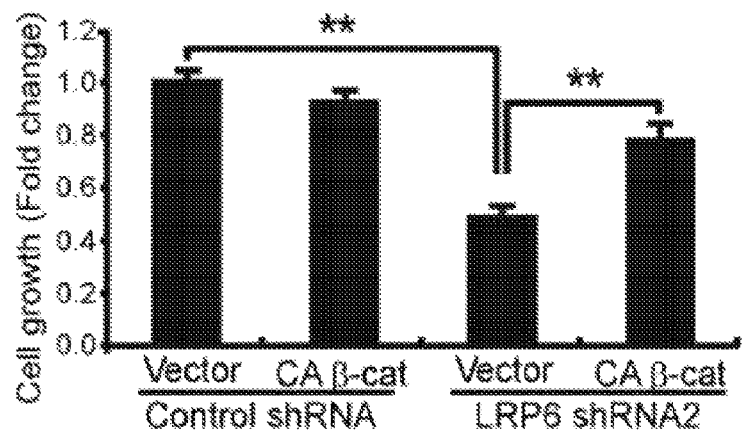

FIG. 16 Continued
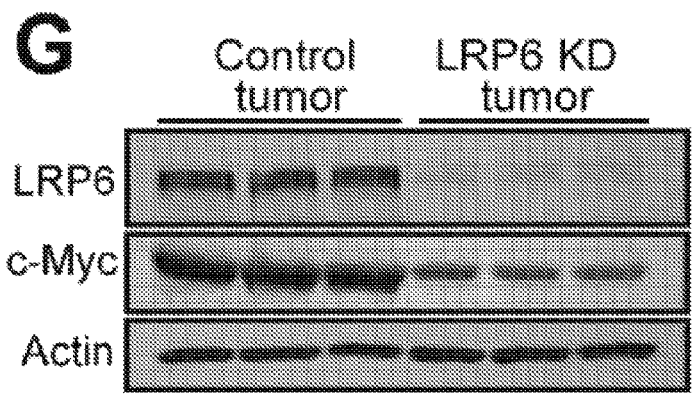
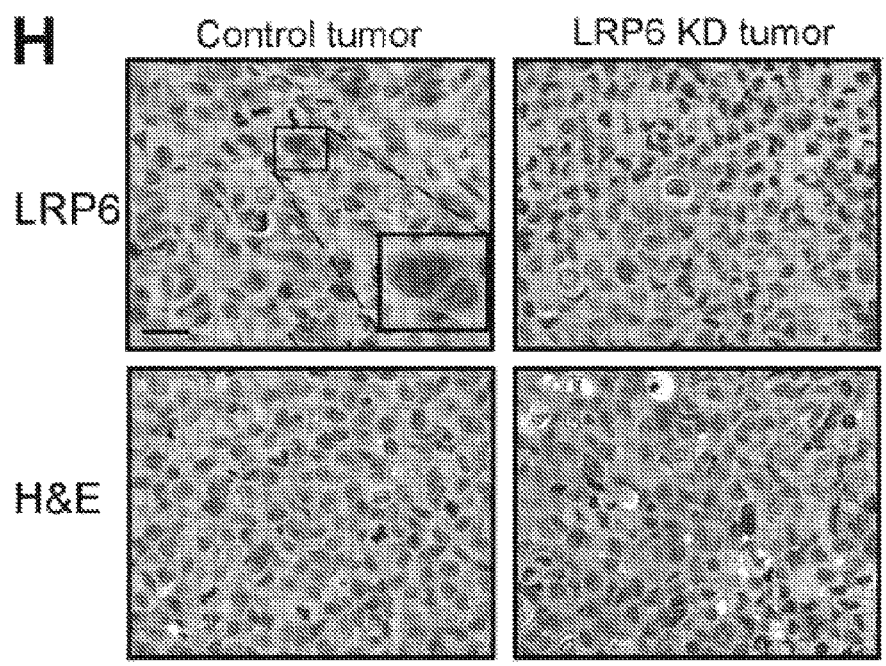
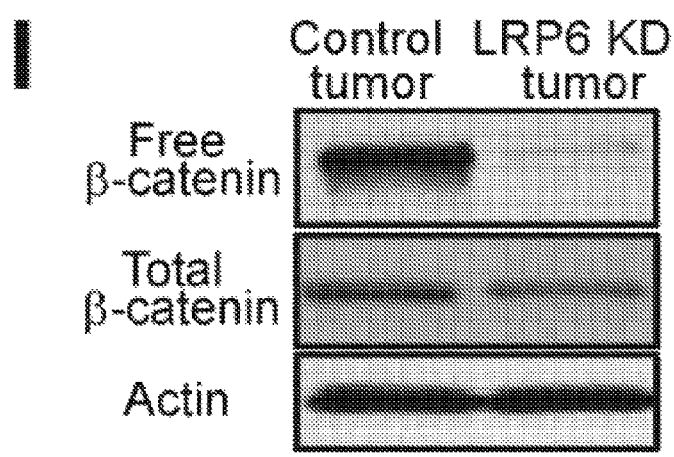

FIG. 21
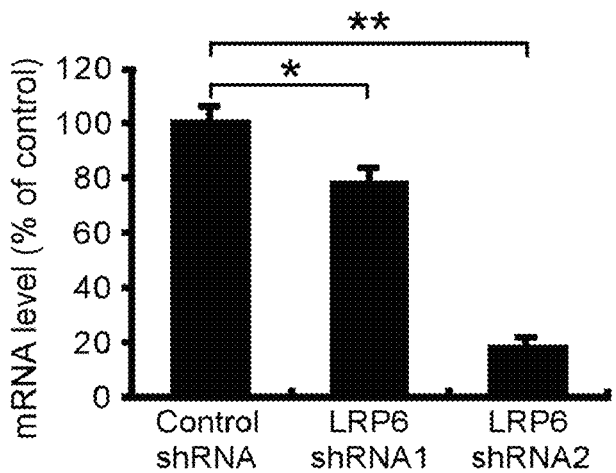
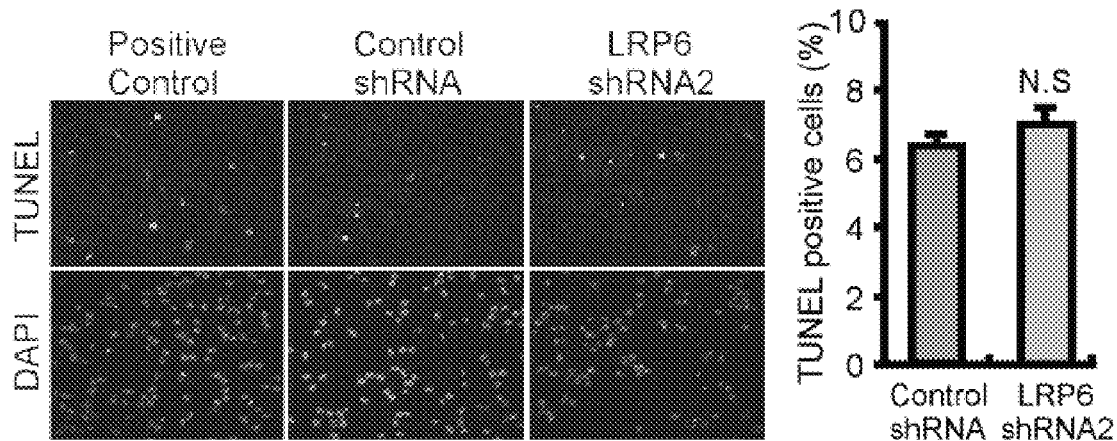
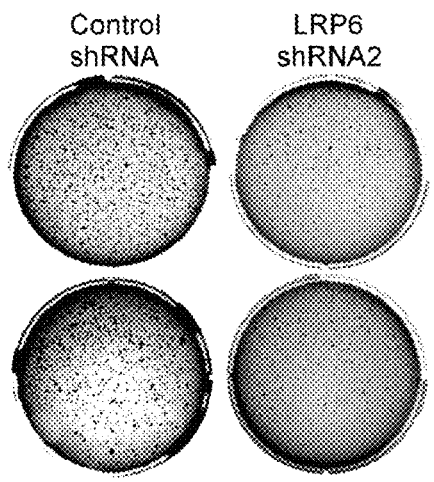

FIG. 22
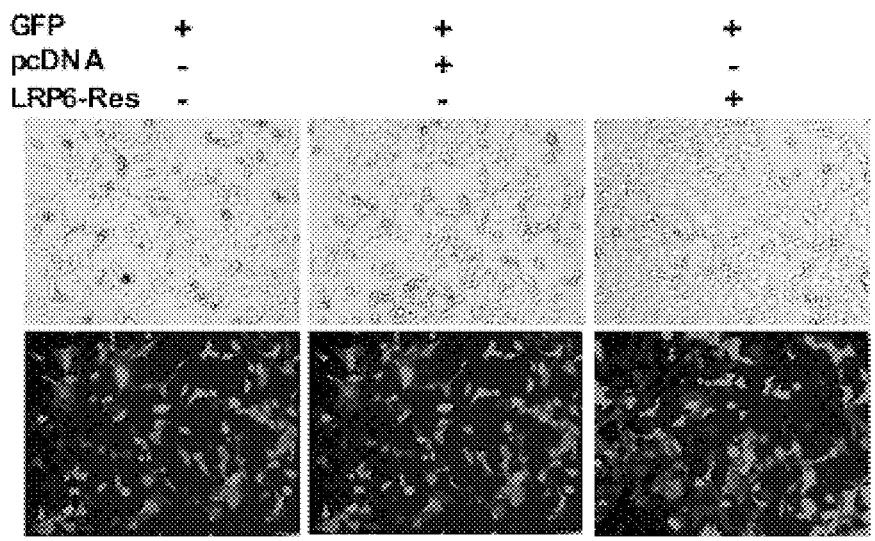
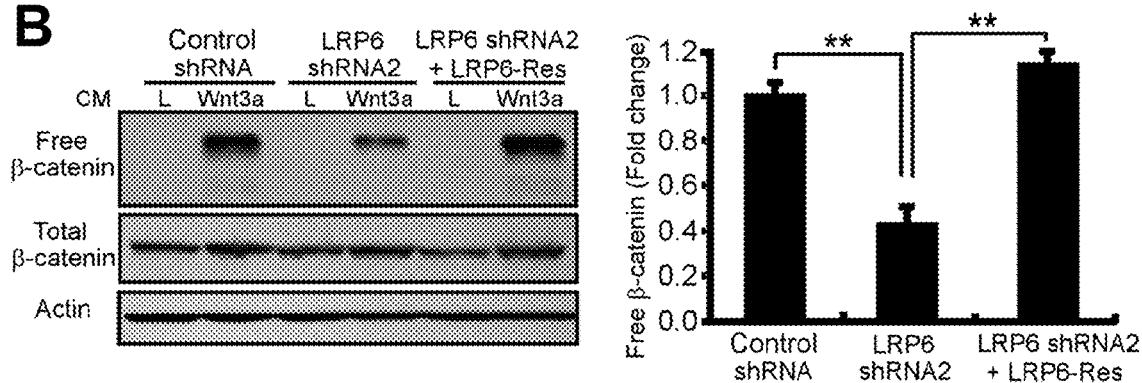
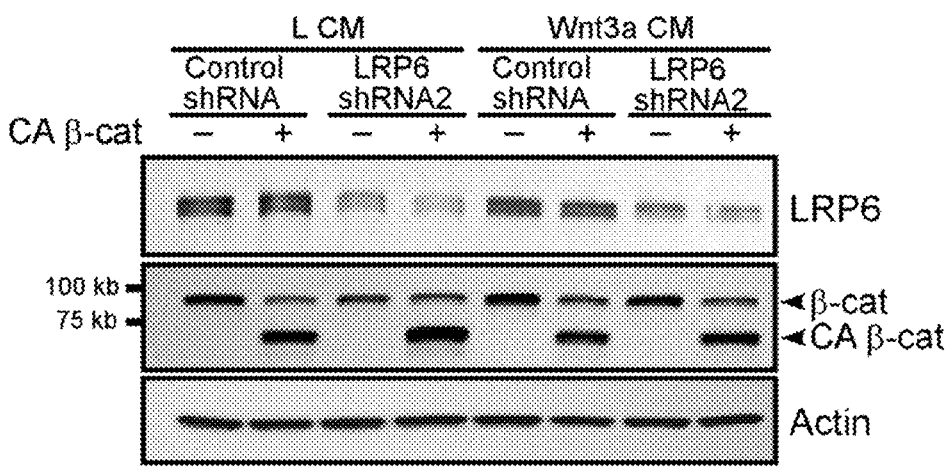

FIG. 23
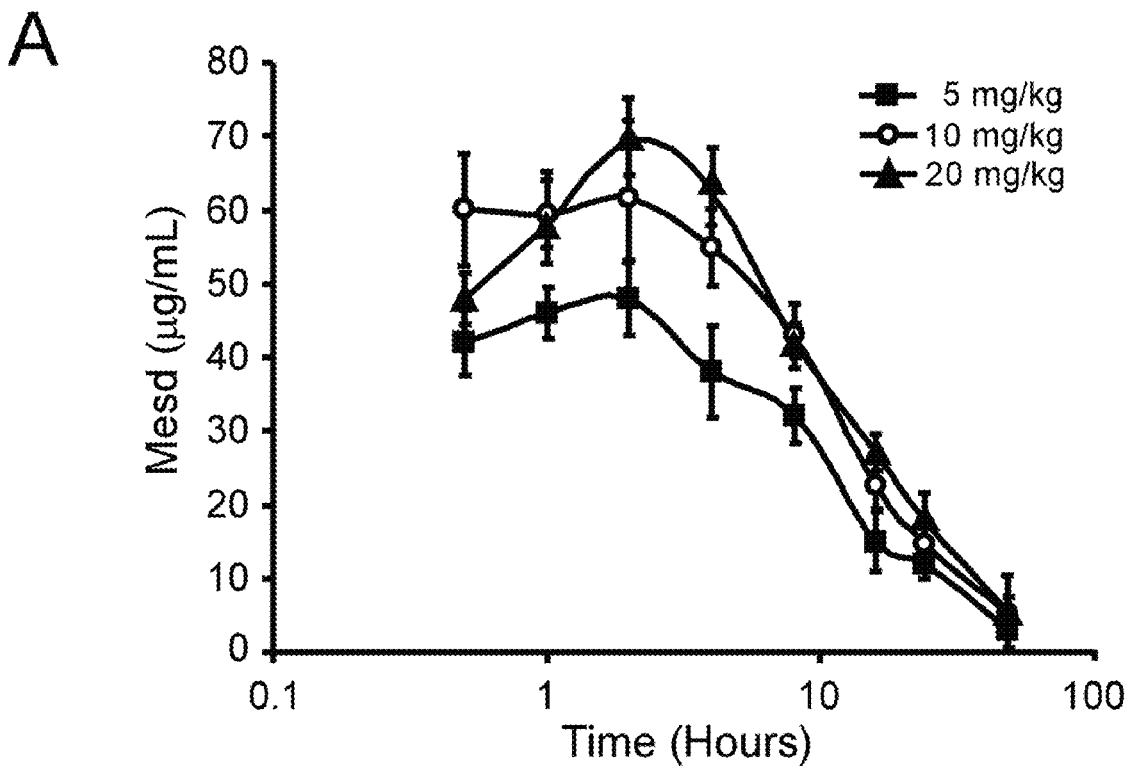
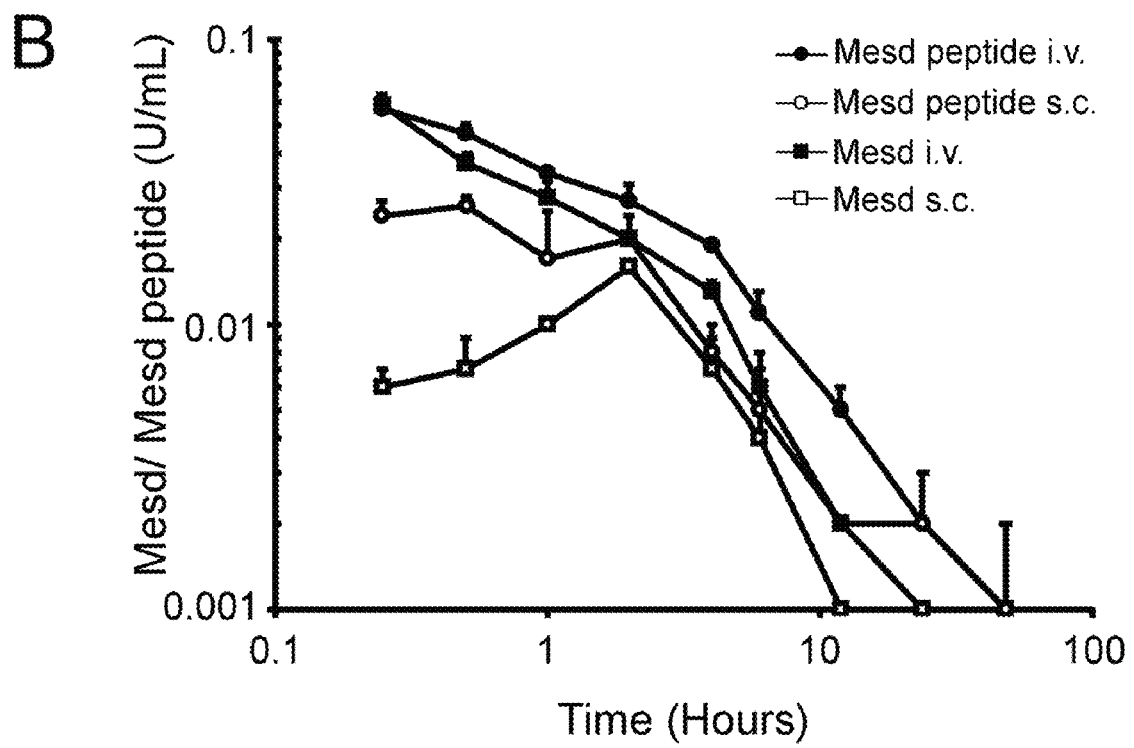

METHODS AND COMPOSITIONS FOR THE TREATMENT OF CANCER

CROSS-REFERENCE TO RELATED APPLICATIONS

This application claims priority from U.S. Provisional Application Ser. No. 60/914,902 filed Apr. 30, 2007, and PCT Application No. PCT/US2008/062092, filed Apr. 30, 2008, each of which is incorporated herein by reference in its entirety.

STATEMENT REGARDING FEDERALLY SPONSORED RESEARCH OR DEVELOPMENT

This invention was made with Government support under grant R01-CA100520 awarded by the National Institutes of Health. The Government has certain rights in the invention.

INCORPORATION-BY-REFERENCE OF MATERIAL SUBMITTED IN COMPUTER READABLE FORM

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

INTRODUCTION

Dysregulation of the Wnt signaling pathway can result in cancer. Several components of the Wnt signaling pathway have been identified as oncogenes or tumor suppressors (showing gain-of-function or loss-of-function mutations, respectively) in human cancers. Dysregulation of Wnt signaling can cause excess proliferation of mammary progenitor cells and predisposes these cells to cancer. For example, activation of the Wnt signaling pathway in the mammary gland is sufficient to induce mammary tumorigenesis, and overexpression of Wnt-1 can result in mammary tumorigenesis (Woodward, W. A., et al., J. Cell Sci. 118: 3585-2598, 2005; Liu, S., et al., Breast Cancer Res. 86-95, 2005; Howe, L. R. and Brown, A. M., Cancer Biol. Ther. 3: 36-41, 2004).

SUMMARY

In view of an unmet need for new treatments for cancer, the present inventors have developed oligopeptides which can prevent, slow or reverse cancer progression. These oligopeptides include full-length polypeptides encoded by the mesd gene, a gene identified as contributing to mesodermal development, as well as fragments thereof.

In some configurations of the present teachings, the inventors have developed oligopeptides, each of which comprises, consists essentially of, or consists of a contiguous subsequence of a polypeptide encoded by a mesd gene. An oligopeptide of these configurations can comprise a full-length mesd polypeptide or a fragment thereof. An oligopeptide of these configurations can comprise, consist essentially of, or consist of an amino acid sequence of from about 10 contiguous amino acids in length up to about 70 contiguous amino acids in length, or from about 30 contiguous amino acids in length up to about 67 contiguous amino acids in length. In various aspects, an oligopeptide can comprise, consist essentially of, or consist of an amino acid sequence selected from (SEQ ID NO: 1)
CADVTLEGQVYPGKGGGSKEKNQTKQEKGKKKKERDLKPRASKEDNRAGS
KKEEL, (SEQ ID NO: 2)
CADVTLEGQVYPGKGGGSQEKNKTKQEKGKKKKEGVPKSRAKVVQEDNRA
GNKREEL, (SEQ ID NO: 3)
CADVTLEGQVYPGKGGGSKEKNKTKQDKGKKKKEGDLKSRSSKEENRAGN
KREDL, (SEQ ID NO: 4)
CALVTLEGQMYPGKGGGSKEKNKTKPEKAKKKEGDPKPRASKEDNRAGSR
REDL, (SEQ ID NO: 5)
CAEVTLEGQMYPGKGGGSKEKNKTKPEKAKKKEGDRKPRASKEDNRAGSR
REDL, (SEQ ID NO: 6)
CADVTLEGQVYPGKGGGSKEKNKTKQDKGKKKKEGDLKSRSSKEDNRARN
KREDL, (SEQ ID NO: 7)
CAEVTLEGQMYPGKGGGSKEKNKTKPEKGKKKEGDPKPRASKEDNRAGSR
REDL, (SEQ ID NO: 8)
CADVTLEGQVYPGKGADGSEKGRNKTKPEKAKKKKDAEKSKSSHEDNRAN
QTERG, (SEQ ID NO: 9)
KGGGSKEKNK, (SEQ ID NO: 10)
KGGGSQEKNK, (SEQ ID NO: 11)
KGGGSKEKINQ, (SEQ ID NO: 12)
KGGGSKERQL, (SEQ ID NO: 13)
KGGGSKEKNKTKQDKGKKKKEGDLKSRSSKEENR, (SEQ ID NO: 14)
KGGGSKEKNKTKQDKGKKKKEGDLKSRSSKEENRAGNK, (SEQ ID NO: 15)
QVYPGKGGGSKEKNKTKQDKGKKKKEGDLKSRSSKEENRAGNKREDL, (SEQ ID NO: 16)
KGGGSKEKNKTKPEKAKKKEGDPKPRASKEDNR, (SEQ ID NO: 17)
KGGGSKEKNKTKPEKAKKKEGDRKPRASKEDNR, (SEQ ID NO: 18)
SKEKNKTKPEKAKKKEGDPKPRASKEDNRAGSRREDL, (SEQ ID NO: 19)
SKEKNKTKPEKAKKKEGDRKPRASKEDNRAGSRREDL, (SEQ ID NO: 20)
KGGGSKEKNKTKPEKAKKKEGDPKPRASKEDNRAGSR, (SEQ ID NO: 21)
KGGGSKEKNKTKPEKAKKKEGDRKPRASKEDNRAGSR, (SEQ ID NO: 22)
QMYPGKGGGSKEKNKTKPEKAKKKEGDPKPRASKEDNRAGSRREDL, (SEQ ID NO: 23)
EGDPKPRASKEDNRAGSR,

EGDRKPRASKEDNRAGSR,
(SEQ ID NO: 24)

TKPEKAKKKEGDPKPRAS,
(SEQ ID NO: 25)

KGGGSKEKNKTKPEKAKKK,
(SEQ ID NO: 26)

TKPEKAKKKEGDRKPRAS,
(SEQ ID NO: 27)

KEDNRAGSR and
(SEQ ID NO: 28)

KEKNKTKPEK.
(SEQ ID NO: 29)

In some aspects, an oligopeptide can comprise a sequence selected from the group consisting of

KGGGSKEKNKTKQDKGKKKKEGDLKSRSSKEENRAGNK,
(SEQ ID NO: 14)

KGGGSKEKNKTKPEKAKKKEGDPKPRASKEDNRAGSR,
(SEQ ID NO: 20)

KGGGSKEKNKTKPEKAKKKEGDRKPRASKEDNRAGSR and
(SEQ ID NO: 21)

QMYPGKGGGSKEKNKTKPEKAKKKEGDPKPRASKEDNRAGSRREDL.
(SEQ ID NO: 22)

In some aspects, an oligopeptide can consist essentially of a sequence selected from the group consisting of

KGGGSKEKNKTKQDKGKKKKEGDLKSRSSKEENRAGNK
(SEQ ID NO: 14)

KGGGSKEKNKTKPEKAKKKEGDPKPRASKEDNRAGSR,
(SEQ ID NO: 20)

KGGGSKEKNKTKPEKAKKKEGDRKPRASKEDNRAGSR and
(SEQ ID NO: 21)

QMYPGKGGGSKEKNKTKPEKAKKKEGDPKPRASKEDNRAGSRREDL.
(SEQ ID NO: 22)

In some aspects, an oligopeptide can consist of a sequence selected from the group consisting of

KGGGSKEKNKTKQDKGKKKKEGDLKSRSSKEENRAGNK
(SEQ ID NO: 14)

KGGGSKEKNKTKPEKAKKKEGDPKPRASKEDNRAGSR,
(SEQ ID NO: 20)

KGGGSKEKNKTKPEKAKKKEGDRKPRASKEDNRAGSR and
(SEQ ID NO: 21)

QMYPGKGGGSKEKNKTKPEKAKKKEGDPKPRASKEDNRAGSRREDL.
(SEQ ID NO: 22)

In some aspects, an oligopeptide of the present teachings which is at least about 10 contiguous amino acids in length up to about 70 contiguous amino acids in length can include conservative amino acid substitutions at one or more positions, as compared to an oligopeptide of a sequence set forth as SEQ ID NO: 1 through SEQ ID NO: 38. In various aspects, an oligopeptide of the present teachings can exhibit a biochemical property of antagonizing binding of a Wnt ligand to an LRP5 receptor and/or LRP6 receptor.

Further aspects of the present teachings include a full-length mesd polypeptide which differs in one or more amino acids from those of a polypeptide presented herein by one or more conservative amino acid substitutions, in which the polypeptide antagonizes binding of a Wnt ligand to an LRP5 receptor and/or LRP6 receptor.

In related aspects, the present teachings also include oligopeptides having at least about 70%, 71%, 72%, 73%, 74%, 75%, 76%, 77%, 78%, 79% sequence identity, at least about 80%, 81%, 82%, 83%, 84%, 85%, 86%, 87%, 88%, 89% sequence identity, or at least 90%, 91%, 92%, 93%, 94%, 95%, 96%, 97%, 98%, 99% sequence identity with a polypeptide set forth as SEQ ID NO: 1 through SEQ ID NO: 32, and also inhibits Wnt binding an LRP5 receptor and/or LRP6 receptor. In various configurations, an oligopeptide can be a substantially pure oligopeptide or an isolated oligopeptide, including a substantially pure or isolated full-length Mesd polypeptide or a portion thereof such as an oligopeptide having a sequence set forth in SEQ ID NO: 1 through SEQ ID NO: 32, or an oligopeptide having conservative substitutions with respect to a sequence of a full-length Mesd polypeptide set forth in Table I or an oligopeptide set forth as SEQ ID NO: 1 through SEQ ID NO: 32.

TABLE I

| Species Common Name | Sequence | SEQ ID NO: | Accession No. |
| --- | --- | --- | --- |
| Bos taurus (cow) | MAASGWARAAVIFLCACDLLLLLLLPPRA FATEGPAETPGEATPPPRKKKKDIRDYND ADMARLLEQWEKDDDIEEGDLPEHKRPSA PIDFSQIDPGKPESILKMTKKGKTLMMFV TVSGNPTEKETEEITSLWQGSLFNANYDV QRFIVGSDRAIFMLRDGGYAWEIKDFLVS QDRCADVTLEGQVYPGKGGGSKEKNQTKQ EKGKKKKERDLKPRASKEDNRAGSKKEEL | 30 | NM_001034469.1 |
| Canis familiaris (dog) | MGSHVLVTRVIGAESCWRLGLHLKKDDDI EEGDLPEHKRPSAPIDFSQIDPGRPESIL KMTKKGKTLMMFVTVSGSPTEKETEEITS LWQGSLFNANYDVQRFIVGSDRAIFMLRD GSYAWEIKDFLVSQDRCADVTLEGQVYPG KGGGSQEKNKTKQEKGKKKKEGVPKSRAA KVVQEDNRAGNKREEL | 31 | XM_545883.2 |
| Homo sapiens (human) | MAASRWARKAVVLLCASDLLLLLLLLPPP GSCAAEGSPGTPDESTPPPRKKKKDIRDY NDADMARLLEQWEKDDDIEEGDLPEHKRP SAPVDFSKIDPSKPESILKMTKKGKTLMM | 32 | NM_051514 |

TABLE I-continued

| Species Common Name | Sequence | SEQ ID NO: | Accession No. |
|---|---|---|---|
| | FVTVSGSPTEKETEEITSLWQGSLFNANY DVQRFIVGSDRAIFMLRDGSYAWEIKDFL VGQDRCADVTLEGQVYPGKGGGSKEKNKT KQDKGKKKKEGDLKSRSSKEENRAGNKRE DL | | |
| *Gallus gallus* (chicken) | MAAAARWAALGLALWLCAAAHAEEPEGKR RAGPAKKKDIRDYNDADMARLLEQWEKDD DIEEGDLPEHKRPPAPIDFSKIDPGKPES ILKLTKKGKTLMMFVTVSGNPTEKETEEI TSLWQGSLFNANYDVQRFIVGSNRAIFML RDGGYAWEIKDFLISQERCADVTLEGQVY PGKGADGSEKGRNKTKPEKAKKKKDAEKS KSSHEDNRANQTERGSMTDT | 33 | NM_001030551 |
| *Mus musculus* (house mouse) | MAASRWLRAVLLFLCASDLLLLPPPNAYA ADTPGEATPPPRKKKDIRDYNDADMARLL EQWEKDDDIEEGDLPEHKRPSAPIDFSKL DPGKPESILKMTKKGKTLMMFVTVSGNPT EKETEEITSLWQGSLFNANYDVQRFIVGS DRAIFMLRDGSYAWEIKDFLVSQDRCAEV TLEGQMYPGKGGGSKEKNKTKPEKAKKKE GDRKPRASKEDNRAGSRREDL | 34 | NM_023403 |
| *Pan troglodytes* (chimpanzee) | MAASRWARKAVVLLCASDLLLLLLLLPPP GSCAAEGSPGTPDESTPPPRKKKKDIRDY NDADMARLLEQWEKDDDIEEGDLPEHKRP SAPVDFSKIDPSKPESILKMTKKGKTLMM FVTVSGSPTEKETEEITSLWQGSLFNANY DVQRFIVGSDRAIFMLRDGSYAWEIKDFL VGQDRCADVTLEGQVYPGKGGGSKEKNKT KQDKGKKKKEGDLKSRSSKEENRAGNKRE DL | 35 | XM_510542.1 |
| *Pongo pygmaeus* (orangutan) | MAASSWARKAVVVLCASDLLLLLLLLPPP GSCAAEASPGTPDESTPPPRKKKKDIRDY NDADMARLLEQWEKDDDIEEGDLPEHKRP SAPVDFSKIDPSKPESILKMTKKGKTLMM FVTVSGSPTEKETEEITSLWQGSLFNANY DVQRFIVGSDRAIFMLRDGNYAWEIKDFL VGQDRCADVTLEGQVYPGKGGGSKEKNKT KQDKGKKKKEGDLKSRSSKEDNRARNKRE DL | 36 | CR860539 |
| *Rattus norvegicus* (Norway rat) | MAASSWLRAVLLFLCASDLLLLSPPEAYA TDTPGEAITPPRKKKDIRDYNDADMARLL EQWEKDDDIEEGDLPEHKRPSAPIDFSKL DPGKPESILKNTKKGKTLMMFVTISGNPT EKETEEITSLWQGSLFNANYDVQRFIVGS DRAIFMLRDGSYAWEIKDFLVNQDRCAEV TLEGQMYPGKGGGSKEKNKTKPEKGKKKE GDPKPRASKEDNRAGSRREDL | 37 | NM_001008345 |
| *Xenopus laevis* (African clawed frog) | MGRSRSRSPERRRERRRSRSASRERERRR RERSRSRERRRSRSRSPHRRRSRSPRRHR SSSISPSRLKDRRDDDKKEPKESKGGGSK ERQLAAEDLEGKTEEEIEMMKLMGFASFD SSKGKKTDGSVNAYAINVSQKRKYRQYMN RKGGFNRPLDFVA | 38 | BC074295 |

In various aspects, the sequence of a Mesd polypeptide or a portion thereof can be that of a polypeptide or a portion thereof comprising at least about 10 contiguous amino acids and encoded by a mesd gene from any animal, including, in non-limiting example, a vertebrate such as a fish, a reptile, an amphibian such as *Xenopus laevis*, a bird such as *Gallus gallus* or a mammal such as a human or rodent such as *Mus musculus*, provided the sequence shares at least about 70%, 71%, 72%, 73%, 74%, 75%, 76%, 77%, 78%, 79% sequence identity, at least about 80%, 81%, 82%, 83%, 84%, 85%, 86%, 87%, 88%, 89% sequence identity, or at least 90%, 91%, 92%, 93%, 94%, 95%, 96%, 97%, 98%, 99% sequence identity with a Mesd polypeptide or at least one sequence set forth as SEQ ID NO: 1 through SEQ ID NO: 38, and also inhibits Wnt binding to an LRP5 receptor and/or LRP6 receptor, such as an LRP5 receptor and/or LRP6 receptor expressed on a cancer cell. In various aspects, a Mesd polypeptide or oligopeptide can be at least about 20 contiguous amino acids, at least about 30 contiguous amino acids, or at least 37 contiguous amino acids in length, up to and including full length genes. In various aspects, a polypeptide or oligopeptide antagonizes binding of a Wnt ligand to an LRP5 receptor and/or LRP6 receptor.

In other aspects, the present teachings include methods of treatment of cancers in which Wnt signaling is modified. In one embodiment the method comprises administering to a subject in need of therapy, such as a human patient diagnosed with cancer, a Mesd polypeptide, a therapeutically effective amount of a Mesd polypeptide as set forth in table I or an oligopeptide which is at least about 10 contiguous amino acids in length up to about 70 contiguous amino acids in length, and comprises a sequence set forth in SEQ ID NO: 1 through SEQ ID NO: 32, or a sequence comprising at least 10 contiguous amino acids in length up to about 70 contiguous amino acids in length and sharing at least about 70%, 71%, 72%, 73%, 74%, 75%, 76%, 77%, 78%, 79% sequence identity, at least about 80%, 81%, 82%, 83%, 84%, 85%, 86%, 87%, 88%, 89% sequence identity, or at least 90%, 91%, 92%, 93%, 94%, 95%, 96%, 97%, 98%, 99% sequence identity with a Mesd polypeptide as set forth in Table I or at least one sequence set forth as SEQ ID NO: 1 through SEQ ID NO: 38. In related aspects, a cancer can be treated by administering to a subject a full length Mesd polypeptide, such as a polypeptide set forth in Table I, including a mammalian Mesd polypeptide such as a human or murine Mesd polypeptide.

In some configurations, a cancer can be treated by administering to a subject a polypeptide sharing at least about 70%, 71%, 72%, 73%, 74%, 75%, 76%, 77%, 78%, 79% sequence identity, at least about 80%, 81%, 82%, 83%, 84%, 85%, 86%, 87%, 88%, 89% sequence identity, or at least 90%, 91%, 92%, 93%, 94%, 95%, 96%, 97%, 98%, 99% sequence identity with full length Mesd polypeptide, such as a polypeptide set forth in Table I, including a mammalian Mesd polypeptide such as a human or murine Mesd polypeptide.

In various other aspects, the inventor have developed vectors comprising a promoter operably linked to a nucleic acid sequence encoding a Mesd polypeptide, or an oligopeptide which comprises a sequence from a polypeptide encoded by the mesd gene as described herein. In various aspects, a vector can be a plasmid or a virus, and a promoter can be a eukaryotic promoter or a prokaryotic promoter. These vectors can be used to produce an oligopeptide ex vivo, e.g., by expression in a host cell or host microorganism in vitro, or can be used therapeutically, such as by administering a vector described in the present teachings, or by administering, to a subject in need of treatment, cells comprising the vector and which produce a full-length Mesd polypeptide or a Mesd oligopeptide. In such configurations, a vector can comprise, in addition to a promoter and a nucleic acid encoding an Mesd polypeptide or oligopeptide, a sequence linked to those encoding the polypeptide or oligopeptide and encodes an amino acid sequence which promotes polypeptide or oligopeptide export or secretion from a cell, such as a leader peptide sequence known to those of skill in the art.

BRIEF DESCRIPTION OF THE DRAWINGS

FIG. 1 illustrates that Mesd binds to mature LRP6 at the cell surface with high affinity.

FIG. 8 illustrates that the 39 kDa specialized molecular chaperone receptor-associated protein RAP binds to LRP6 and partially competes for Mesd binding.

FIG. 15 illustrates that shRNA-resistant LRP6 and CA β-catenin can rescue Wnt signaling and cell growth in MDA-MB-231 cells.

FIG. 21 illustrates effects of LRP6 knockdown on apoptosis and soft agar colony formation in MDA-MB-231 breast cancer cells.

FIG. 22 illustrates rescue of Wnt signaling by shRNA-resistant LRP6 and CA β-catenin.

FIG. 23 illustrates examination of pharmacokinetics of Mesd peptide and Mesd.

DETAILED DESCRIPTION

Figure 2:
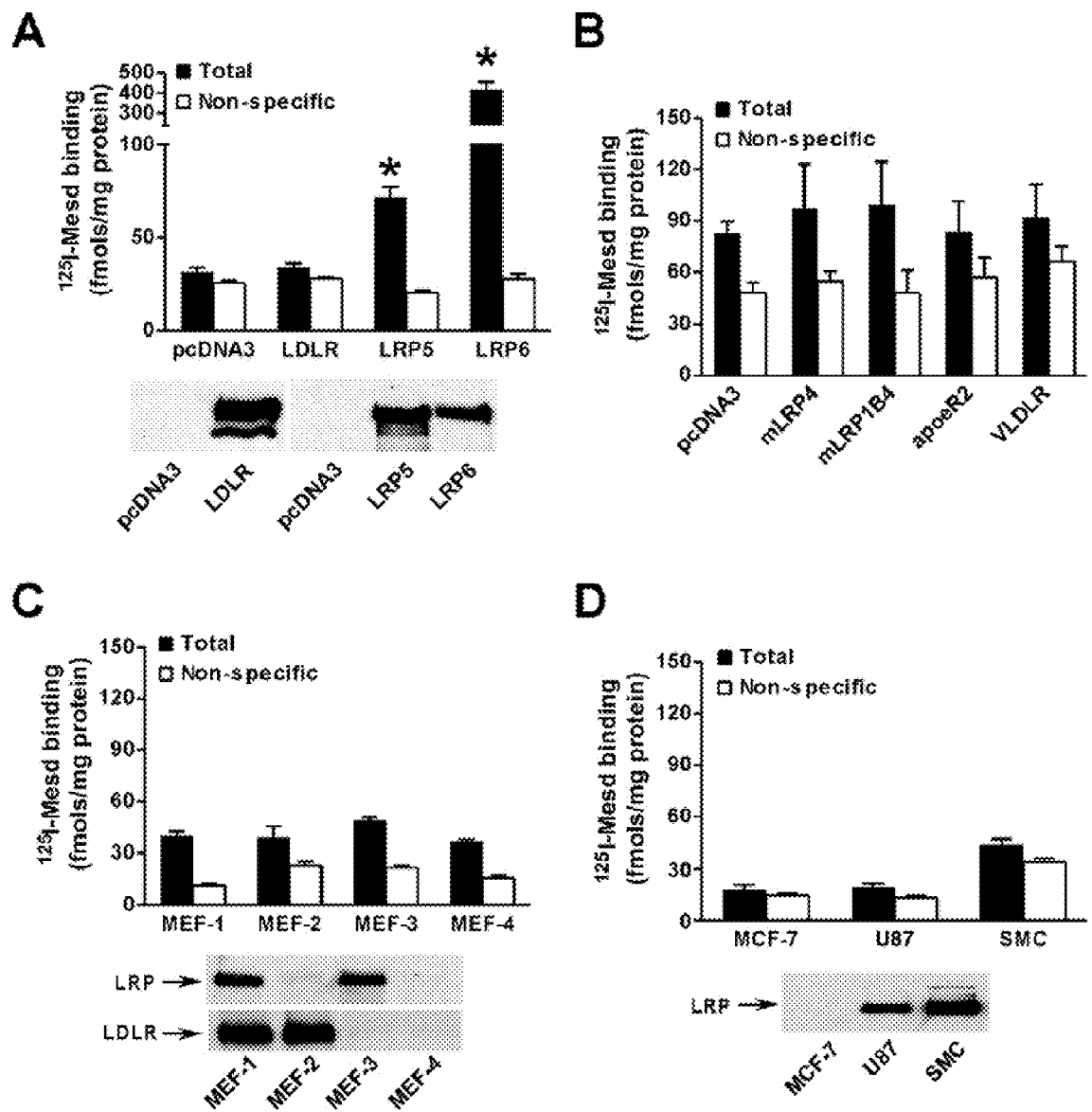
FIG. 2 illustrates that Mesd binds to mature LRP5 and LRP6 but not significantly to other members of the LDLR family.

Wnt receptors are candidate oncoproteins, and mutated forms of two members of the mammalian low-density lipoprotein receptor (LDLR)-related protein (LRP) family, LRP5 and LRP6, have recently been shown to be capable of constitutively activating Wnt/β-catenin signaling in cell culture. The present findings utilize LRP5 AND LRP6-specific inhibitors such as Mesd to inhibit Wnt signaling at the cell surface.

The methods and compositions described herein utilize laboratory techniques well known to skilled artisans and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Harlow, E., Using Antibodies: A Laboratory Manual, Cold Spring Harbor Laboratory Press, Cold Spring Harbor, N.Y., 1999, and Ausubel, F. M., et al., ed., Current Protocols in Molecular Biology. For pharmaceutical compositions and methods of treatment disclosed herein, dosage forms and administration regimes can be determined using standard methods known to skilled artisans, for example as set forth in standard references such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

The present inventor discloses substantially pure oligopeptides which can be used to treat cancers, including a cancer in which cancerous cells exhibit modified Wnt signaling, such as, without limitation, breast cancer, multiple myeloma (MM), prostate cancer and skin cancer. Without being limited by theory, the present inventor has found that an Mesd polypeptide can inhibit Wnt ligand binding to (LDLR)-related protein-5 (LRP5) and (LDLR)-related protein-6 (LRP6). Accordingly, Mesd polypeptide or a functional fragment thereof can be used for treating cancer and for increasing bone health, as described in U.S. patent application Ser. No. 11/557,292, filed Nov. 7, 2006. Without being limited by theory, the inventor presumes that signaling by the low-density lipoprotein receptor (LDLR)-related protein-5 (LRP5) and (LDLR)-related protein-6 (LRP6) which are both members of the LDLR family, is subject to inhibition by an extracellular Wnt ligand. Recently, a specialized chaperone for members of the LDLR family, termed Mesd (mesoderm development) in mouse and Boca in Drosophila has been identified (Culi, J., Cell 112: 343-354, 2003; Hsieh, J. C., Cell 112: 355-367, 2003). This new chaperone was discovered due to its requirement for the folding of LRP5/LRP6, co-receptors for the Wnt/Wg signaling pathway. However, the present inventor has found that Mesd not only mediates folding of LRP5 and LRP6, it also is capable of binding mature LRP5 or LRP6 at the cell surface, and antagonizes binding of ligand such as a Wnt ligand. In addition, the present inventor has determined that the ligand-binding antagonizing activity is found in oligopeptides comprising subsequences of Mesd from the carboxy-terminal region of the Mesd polypeptide.

Oligopeptides of the present teachings comprise from about 10 contiguous amino acids up to about 70 contiguous amino acids, wherein the peptide comprises an amino acid sequence selected from the group consisting of SEQ ID NO: 9, SEQ ID NO: 10, SEQ ID NO: 11 and SEQ ID NO: 12. The sequences represent subsequences from Mesd polypeptide encoded by a mesd gene comprised by the genome of a variety of species such as, without limitation, human, mouse, dog, cow, chimpanzee, orangutan and rat. As used herein, the term "oligopeptide" refers to a molecule comprising at least two amino acids joined by peptide bonds, and the term "polypeptide" refers to a molecule comprising a full-length amino acid sequence as encoded by a gene, an mRNA or a cDNA. In various configurations, a substantially pure oligopeptide of the present teachings can comprise at least 20 or at least 30 contiguous amino acids, up to about 67 amino acids. Sequences of the present teachings are set forth herein in Table II, which present oligopeptide sequences of from 54 to 67 contiguous amino acids, and Table III, which presents oligopeptide sequences of from 10 to 46 amino acids. An oligopeptide of the present teachings can be synthesized using standard techniques well known to skilled artisans, such as, in non-limiting example Merrifield solid phase synthesis, or molecular cloning methods, including, in non-limiting example, synthesizing an oligonucleotide encoding an oligopeptide and inserting the oligonucleotide into a vector, or subcloning a portion of a cDNA into a vector using restriction enzyme digestion, ligation with a ligase, and/or polymerase chain reaction techniques. A vector comprising an oligonucleotide encoding an oligopeptide can in inserted into a cell by transfection or transformation, and expressed in the cell using methods well known to skilled artisans. Oligopeptides can be isolated and/or purified by standard techniques well known to skilled artisans.

TABLE II

| Species Common Name | Sequence | Seq. ID No. |
|---|---|---|
| Bos taurus (cow) | CADVTLEGQVYPGKGGGSKEKNQTKQE KGKKKKERDLKPRASKEDNRAGSKKEE L | 1 |
| Canis familiaris (dog) | CADVTLEGQVYPGKGGGSQEKNKTKQ EKGKKKKEGVPKSRAKVVQEDNRAGNK REEL | 2 |
| Homo sapiens (human) | CADVTLEGQVYPGKGGGSKEKNKTKQD KGKKKKEGDLKSRSSKEENRAGNKRED L | 3 |
| Mus musculus (house mouse) | CAEVTLEGQMYPGKGGGSKEKNKTKPE KAKKKEGDPKPRASKEDNRAGSRREDL | 4 |
| Mus musculus (house mouse) | CAEVTLEGQMYPGKGGGSKEKNKTKPE KAKKKEGDRKPRASKLDNRAGSRREDL | 5 |
| Pan troglodytes (chimpanzee) | CADVTLEGQVYPGKGGGSKEKNKTKQD KGKKKKEGDLKSRSSKEENRAGNKRED L | 3 |
| Pongo pygmaeus (orangutan) | CADVTLEGQVYPGKGGGSKEKNKTKQD KGKKKKEGDLKSRSSKEDNRARNKRED L | 6 |
| Rattus norvegicus (Norway rat) | CAEVTLEGQMYPGKGGGSKEKNKTKPE KGKKKEGDPKPRASKEDNRAGSRREDL | 7 |
| Gallus gallus (chicken) | CADVTLEGQVYPGKGADGSEKGRNKTK PEKAKKKKDAEKSKSSHEDNRANQTER G | 8 |

TABLE III

| Source | Sequence | Seq. ID No. |
|---|---|---|
| Homo sapiens (human) | KGGGSKEKNKTKQDKGKKKKEGDLKSR SSKEENR | 13 |
| Canis familians (dog) | KGGGSKEKNKTKQDKGKKKKEGDLKSR SSKEENR | 13 |
| Bos taurus (cow) | KGGGSKEKNKTKQDKGKKKKEGDLKSR SSKEENR | 13 |
| Xenopus laevis (African Clawed Frog) | KGGGSKEKNKTKQDKGKKKKEGDLKSR SSKEENR | 13 |
| Homo sapiens (human) | KGGGSKEKNKTKQDKGKKKKEGDLKSR SSKEENRAGNK | 14 |
| Homo sapiens (human) | QVYPGKGGGSKEKNKTKQDKGKKKKEG DLKSRSSKEENRAGNKREDL | 15 |
| Mus musculus (house mouse) | KGGGSKEKNKTKQDKGKKKKEGDLKSR SSKEENR | 13 |
| Mus musculus (house mouse) | SKEKNKTKPEKAKKKEGDPKPRASKEDN RAGSRREDL | 18 |
| Mus musculus (house mouse) | SKEKNKTKPEKAKKKEGDRKPRASKEDN RAGSRREDL | 19 |
| Mus musculus (house mouse) | KGGGSKEKNKTKPEKAKKKEGDPKPRAS KEDNRAGSR | 20 |

TABLE III-continued

| Source | Sequence | Seq. ID No. |
|---|---|---|
| Mus musculus (house mouse) | KGGGSKEKNKTKPEKAKKKEGDRKPRASKEDNRAGSR | 21 |
| Mus musculus (house mouse) | QMYPGKGGGSKEKNKTKPEKAKKKEGDPKPRASKEDNRAGSRREDL | 22 |
| Mus musculus (house mouse) | EGDPKPRASKEDNRAGSR | 23 |
| Mus musculus (house mouse) | EGDRKPRASKEDNRAGSR | 24 |
| Mus musculus (house mouse) | TKPEKAKKKEGDPKPRAS | 25 |
| Mus musculus (house mouse) | KGGGSKEKNKTKPEKAKKK | 26 |
| Mus musculus (house mouse) | TKPEKAKKKEGDRKPRAS | 27 |
| Mus musculus (house mouse) | KGGGSKEKNK | 9 |
| Mus musculus (house mouse) | KEDNRAGSR | 28 |
| Mus musculus (house mouse) | KEKNKTKPEK | 29 |

In oligopeptides of the present teachings comprising conservative substitutions, such substitutions can be from families of amino acid residues having similar side chains as have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Conserved substitutes for an amino acid within a native amino acid sequence can be selected from other members of the family to which the naturally occurring amino acid belongs.

A further aspect of the invention comprises polypeptides and oligopeptides which differ in one or more amino acids from those of a polypeptide or oligopeptide sequence described herein by deletion or insertion of one or more amino acids.

Accordingly, in some configurations of the present teachings, an oligopeptide can be from about 10 amino acids in length up to 67 amino acids in length. The sequence can comprise any sequence set forth in Table II or Table III, and/or can include any sequence selected from SEQ ID NO: 1 through SEQ ID NO: 38. Furthermore, a sequence of an oligopeptide can be a sequence sharing at least 70% sequence identity, at least 80% sequence identity, or at least 90% sequence identity with at least one sequence of SEQ ID NO: 1 through SEQ ID NO: 38 and has the biochemical property of antagonizing, inhibiting or blocking binding of a mature cell surface proteins LRP5 and/or LRP6 with an extracellular ligand such as a Wnt ligand, when the oligopeptide is contacted with an LRP5 and/or LRP6, such as an LRP5 and/or LRP6 comprised by a cell membrane. Furthermore, a sequence of an oligopeptide can be a sequence sharing at least 70% sequence identity, at least 80% sequence identity, or at least 90% sequence identity with at least one sequence of SEQ ID NO: 1 through SEQ ID NO: 38 and furthermore can have the biochemical property of antagonizing Wnt signaling. In various configurations, conservative substitutions can be made in oligopeptide sequences, for example substitution of a hydrophobic amino acid such as valine with a different hydrophobic amino acid such as isoleucine. Methods for identifying and selecting conservative substitutions for amino acids are well known to skilled artisans (see, e.g., Pearson, W. R., Methods Enzymol. 266: 227-258, 1996).

In other configurations of the present teachings, the inventor disclose nucleic acid vectors comprising a promoter operably linked to a nucleic acid sequence encoding an oligopeptide comprise a sequence selected from SEQ ID NO: 1 through SEQ ID NO: 38. In some aspects, the oligopeptide or polypeptide sequence can be a sequence sharing at least about 70%, 71%, 72%, 73%, 74%, 75%, 76%, 77%, 78%, 79% sequence identity, at least about 80%, 81%, 82%, 83%, 84%, 85%, 86%, 87%, 88%, 89% sequence identity, or at least 90%, 91%, 92%, 93%, 94%, 95%, 96%, 97%, 98%, 99% sequence identity with at least one of SEQ ID NO: 1 through SEQ ID NO: 38. A promoter of these configurations can be a eukaryotic promoter (i.e., a promoter which can support transcription in the environment of a eukaryotic cell such as a mammalian cell or a microbial eukaryotic cell such as a yeast cell) or a prokaryotic promoter (i.e., a promoter which can support transcription in the environment of a prokaryotic cell such as a bacterium). Non-limiting examples of a promoter which can be used in a vector of the present teachings include an actin promoter, a CUP1 promoter from a yeast metallothionein gene, and promoter-enhancer elements from the simian virus 40 (SV40) early-region or a mouse alpha 2(I)-collagen gene, and an *E. coli* lac operon operator/promoter. A vector can be, for example, a plasmid or a virus, such as, for example, a baculovirus or a bacteriophage. In addition, in some configurations, the present teachings encompass a cell comprising a vector as described herein. A cell comprising a vector can be a cell in which the promoter of the vector is operable, for example an *E. coli* cell harboring a plasmid comprising a lac operon/promoter, or an insect cell harboring a baculovirus vector.

In various configurations, the present teachings include methods of treating cancer in a subject in need of treatment. Methods of these configurations include administering to a subject a therapeutically effective amount of a Mesd polypeptide, a polypeptide sharing at least 70% sequence identity, at least 80% sequence identity, or at least 90% sequence identity with an Mesd polypeptide, or an oligopeptide comprising between 10 contiguous amino acids and about 70 contiguous amino acids, wherein the oligopeptide comprises an amino acid sequence selected from SEQ ID NO: 1 through SEQ ID NO: 38 and a sequence sharing at least 70% sequence identity, at least 80% sequence identity, or at least 90% sequence identity with at least one sequence set forth as SEQ ID NO: 1 through SEQ ID NO: 38, wherein an polypeptide or oligopeptide antagonizes binding of a Wnt ligand to an LRP5 receptor and/or LRP6 receptor. when in contact with LRP5. In some aspects, the cancer can be breast cancer and multiple myeloma (MM), prostate cancer and skin cancer, or any cancer with these characteristics. These methods can also be applied to cells or tissues in vitro or ex vivo. In addition, in some aspects, the present methods also include administering to a subject in need of treatment a vector such as described above, or cells comprising a vector, such as human cells comprising a vector comprising a eukaryotic promoter operably linked to a nucleic acid encoding an oligopeptide as described herein. In non-limiting example, the human cells can be cells from a subject which are transformed with a vector, grown in vitro using standard cell culture techniques, and returned to the donor.

A therapeutically effective amount of a polypeptide, oligopeptide or vector of the present teachings can be determined using methods well known in the art, such as found in standard pharmaceutical texts such as Herfindal, Gourley and Hart, Williams and Wilkins, ed. Clinical Pharmacy and Therapeutics, Williams & Wilkins, 1988; Goodman, L. S. and Gilman, A., ed. The Pharmacological Basis of Therapeutics, McGraw-Hall; 2005; Kalant, H., and Roschlau, W. H. E., ed., Principles of Medical Pharmacology, Mosby, Incorporated. 1989; J. T. DiPiro, R. L. et al., ed. Pharmacotherapy: A Pathophysiologic Approach, McGraw-Hill Medical Publishing, 2005; Ascione, Principles of Scientific Literature Evaluation Critiquing Clinical Drug Trials, American Pharmacists Association, 2001; and Remington, The Science and Practice of Pharmacy, Lippincott Williams & Wilkins, 2005.

EXAMPLES

The following examples provide non-limiting illustrations of the present teachings. While some of examples may include conclusions about the way the invention may function, the inventor does not intend to be bound by those conclusions, but put them forth only as possible explanations. Unless indicated by use of past tense, presentation of an example does not imply that an experiment or procedure was, or was not, conducted, or that results were, or were not, actually obtained.

Example 1

This example illustrates that Mesd binds to mature LRP6 at the cell surface.

To examine whether Mesd binds with high affinity to most members of the LDLR family at the cell surface, we performed cell surface ligand binding experiments with cells stably transduced with LRP6 cDNA. Human HT1080 cells, which express undetectable levels of LRP6, were transduced with a viral vector alone (pLNCX2) or with vector containing LRP6 cDNA (Li, Y., Oncogene 23: 9129-9135, 2004) and used for $^{125}$I-Mesd binding (FIG. 1A). $^{125}$I-Mesd (5 nM) reached maximal binding after 2 hours incubation at 4° C. with LRP6-expressing HT1080 cells (FIG. 1A). Inclusion of excess unlabeled Mesd (500 nM) completely eliminated this binding. No significant $^{125}$I-Mesd binding was seen with the control cells (pLNCX2). Saturation of Mesd specific binding was seen at concentrations of >6.4 nM (FIG. 1B). Scatchard analysis of the binding data revealed that Mesd binds LRP6 with a Kd of ~3.3 nM (FIG. 1C). This affinity of Mesd to LRP6 is comparable to that of RAP to LRP (Iadonato, S. P., Biochem. J. 296: 867-875, 1993).

As illustrated in FIG. 1, Mesd binds to mature LRP6 at the cell surface with high affinity. (A) Time course of $^{125}$I-Mesd (5 nM) binding to LRP6-transduced HT1080 cells and the control cells. Assay was carried out for the indicated periods at 4° C. in the absence (total) or presence of 500 nM Mesd (non-specific). (B) Saturation binding of $^{125}$I-Mesd to LRP6-transduced HT1080 cells and the control cells. Assay was carried out at indicated concentrations for 3 hours at 4° C. in the absence (total) or presence (non-specific) of 500 nM Mesd. (C) Scatchard plots of data in B. All values are the average of triple determinations with the s.d. indicated by error bars.

In these examples, the following materials and methods were used:

Materials

Human recombinant DKK1 protein and mouse recombinant Wnt3a protein were from R&D Systems. Human recombinant RAP protein was expressed in a glutathione S-transferase (GST) expression vector and isolated as described previously (Bu et al., 1993). Monoclonal anti-Myc antibody 9E10 was from Roche. Monoclonal antibody 8G1 against human LRP was from Research Diagnostics. Monoclonal anti-HA antibody has been described before (Li, Y., J. Biol. Chem. 275: 17187-17194, 2000). Polyclonal rabbit anti-LDLR was produced by immunizing rabbits with recombinant human LDLR1-294 fragment. Peroxidase-labeled anti-mouse antibody and ECL system were from Amersham Life Science. Plasmid pcDNA3.1C-Myc-hLRP5 containing the full-length human LRP5 cDNA and plasmid pCS-Myc-hLRP6 containing the full-length human LRP6 cDNA were from Cindy Bartels and Christof Niehrs, respectively. Carrier-free Na$^{125}$I was purchased from NEN Life Science Products. IODO-GEN was from Pierce. Proteins were iodinated by using the IODO-GEN method as described previously (Li, Y., J. Biol. Chem. 275: 17187-17194, 2000).

Cell Lines and Cell Culture

LRP6-transduced HT1080 cells and the control cells have been described before (Li et al., 2004), and were cultured in DMEM medium containing 10% fetal bovine serum and 350 µg/ml G418. The LRP-null CHO cells stably transfected with human LDLR-related protein (LRP) minireceptor mLRP4, mLRP4 tail mutant mLRP4tailess (mLRP4 without the cytoplasmic tail), human LDLR-related protein 1B (LRP1B) minireceptor mLRP1B4, human VLDLR, or human apoER2 have been described before (Li, Y., J. Biol. Chem. 275: 17187-17194, 2000; Li et al., 2001; Liu et al., 2001), and were cultured in Ham's F-12 medium containing 10% fetal bovine serum and 350 µg/ml G418. A set of genetically derived murine embryonic fibroblasts (MEF) from mouse embryos deficient for LRP and/or LDLR were obtained from Joachim Herz, University of Texas Southwestern Medical Center at Dallas (Willnow, J. Cell Sci. 107: 719-726, 1994; Narita, M., J. Biochem. 132: 743-749, 2002). These are MEF-1 (WT), MEF-2 (LRP-deficient), MEF-3 (LDLR-deficient), and MEF-4 (LRP and LDLR-double-deficient), and are cultured in DMEM containing 10% fetal bovine serum. Culture conditions of U87, MCF-7, and human aortic smooth muscle cells have been described before (Li, Y., FEBS Lett. 555: 346-350, 2003). HEK293 cells were from ATCC, and cultured in DMEM containing 10% fetal bovine serum.

Preparation of Recombinant Mesd Protein

Full-length mouse Mesd cDNA was used. The wild-type and mutant forms of mouse Mesd were generated by polymerase chain reactions, and subcloned into the expression vector pET-30a(+) (Novagen) at the EcoRI and HindIII restriction sites. The integrity of the subcloned DNA sequence was confirmed by DNA sequencing. Recombinant proteins were overexpressed from pET-30(+)Mesd in E. coli. BL21(DE3) producing a recombinant fusion protein with a polyhistidine metal-binding tail at the N-terminus, and purified with His-Bind Kits from Novagen according to the manufacturer's protocol. All the recombinant Mesd proteins lack the Mesd signal peptide.

Western Blotting

To examine the expression of the LDLR family members, cells cultured in six-well plates were lysed with 0.5 ml lysis buffer (phosphate-buffered saline containing 1% Triton X-100 and 1 mM PMSF) at 4° C. for 30 minutes. Equal quantities of protein were subjected to SDS-PAGE under non-reducing conditions. Following transfer to Immobilon-P membrane, successive incubations with primary antibody and horseradish peroxidase-conjugated secondary antibody were carried out for 60 minutes at room temperature. The immunoreactive proteins were then detected using the ECL™ system (Amersham).

To examine the cytosolic β-catenin level, cells in six-well plates were treated with Mesd at various concentrations for 90 minutes at 37° C. After washing in ice-cold PBS, cells were collected and homogenized in a glass Dounce homogenizer in buffer consisting of 100 mM Tris-HCl pH 7.4, 140 mM NaCl, 2 mM DTT, 2 mM PMSF, and 1× Complete™ protease inhibitors (500 μl/well). The homogenate was centrifuged for 10 minutes at 500 g, and the supernatant was further centrifuged at 100,000 g at 4° C. for 90 minutes. The resulting supernatant was designated the cytosolic fraction. The β-catenin levels were then examined by western blotting using β-catenin-specific antibody from Cell Signaling Technology. The immunoreactive proteins were detected using the ECL™ system (Amersham). Films showing immunoreactive bands were scanned with a Kodak Digital Science DC 120 Zoom Digital Camera and band intensities were analyzed with Kodak Digital Science1D Image Analysis Software.

Western Blotting and Immunohistochemistry

In some experiments, Western blot analysis was performed as described (Li, Y, et al. J. Cell Sci. 118: 5305-5314, 2005). In these experiments, cells were lysed in PBS containing 0.5% Triton, protease inhibitor cocktail (Roche), and 1 mM PMSF at 4° C. for 30 minutes. Equal quantities of protein were subjected to SDS-PAGE under reducing conditions. Following transfer to Immobilon-P membranes, successive incubations with primary and horseradish peroxidase-conjugated secondary antibodies (Amersham Life Science) were performed according to the manufacturer's specifications. Immunoreactive proteins were detected using the ECL system. For immunohistochemical staining, tumors were fixed in 10% buffered formalin for 48 h, transferred to 70% ethanol/PBS, and embedded in paraffin. Sections were cleared in a graded xylene/ethanol series and treated with 3% hydrogen peroxide/$H_2O$ for 20 minutes. Antigens were retrieved by steaming in citrate buffer (pH 6.0) for 20 minutes and sections were blocked and incubated with the primary antibody at 4° C. overnight. After successive incubations with the corresponding biotin-conjugated secondary antibody and ABC Elite reagent (Vector Laboratories), antigens were detected using diaminobenzidine (DAB) (Vector Laboratories) as the chromogenic substrate. Slides were counterstained with hematoxylin, dehydrated, and mounted. Hemotoxylin and eosin (H&E) staining was performed on tumor xenograft tissue, skin and intestine harvested at the end of Mesd treatment.

Luciferase Reporter Assay

HEK293 cells were plated into six-well plates. For each well, 0.1 μg of the TOP-FLASHTCF luciferase construct (Upstate Biotechnology) was cotransfected with 0.8 μg Mesd-expressing vector, 0.8 μg Mesd mutant-expressing vector, or empty vector. A β-galactosidase-expressing vector (Promega, Madison, Wis.) was included as an internal control for transfection efficiency. After 48 hours, cells were lysed and both luciferase and β-galactosidase activities were determined with enzyme assay kits (Promega). The luciferase activity was determined with a luminometer using the Dual Luciferase Assay system (Promega). Luciferase activity was normalized to the activity of the β-galactosidase.

In some experiments, to examine reporter activities in response to Wnt3a stimulation and/or β-catenin expression, cells expressing control or LRP6 shRNA were transfected with Topflash/Fopflash plasmids (Upstate) and treated with conditioned media from parental L cell or Wnt3a-expressing cultures (3) for 24 h. A β-gal reporter cDNA was cotransfected to normalize data for transfection efficiency. The luciferase and β-gal activities were measured by the Luciferase and β-gal Assay Systems, respectively, following the manufacturer's instructions (Promega).

Ligand Binding and Degradation

Cells ($2 \times 10^5$) were seeded into 12-well dishes 1 day prior to assay. Ligand-binding buffer (minimal Eagle's medium containing 0.6% BSA with a different concentration of radioligand, 0.6 ml/well) was added to cell monolayers, in the absence or the presence of 500 nM unlabeled RAP or 500 nM unlabeled Mesd, followed with incubation for 0-4 hours at 4° C. Thereafter, overlying buffer containing unbound ligand was removed, and cell monolayers were washed and lysed in low-SDS lysis buffer (62.5 mM Tris-HCl pH 6.8, 0.2% SDS, 10% v/glycerol) and counted. The protein concentration of each cell lysate was measured in parallel dishes that did not contain the ligands.

Ligand degradation was performed using the methods as described in Li, Y., et al., J. Biol. Chem. 275: 17187-17194, 2000. Briefly, $2 \times 10^5$ cells were seeded into 12-well dishes 1 day prior to assay. Pre-warmed assay buffer (minimal Eagle's medium containing 0.6% BSA with radioligand, 0.6 ml/well) was added to cell monolayers in the absence or the presence of unlabeled 500 nM RAP or 500 nM Mesd, followed by incubation for 4 hours at 37° C. Thereafter, the medium overlying the cell monolayers was removed and proteins were precipitated by addition of BSA to 10 mg/ml and trichloroacetic acid to 20%. Degradation of radioligand was defined as the appearance of radioactive fragments in the overlying medium that were soluble in 20% trichloroacetic acid. Kinetic analysis of endocytosis LRP6-transduced HT1080 cells were plated in 12-well plates at a density of $2 \times 10^5$ cells/well and used after overnight culture. Cells were rinsed twice in ice-cold assay buffer (minimal Eagle's medium containing 0.6% BSA), and $^{125}$I-anti-HA IgG was added at 1 nM final concentration in cold assay buffer (0.5 ml/well). The binding of $^{125}$I-anti-HA IgG was carried out at 4° C. for 90 minutes with gentle rocking Unbound $^{125}$I-anti-HA IgG was removed by washing cell monolayers three times with cold assay buffer. Ice-cold stop/strip solution (0.2 M acetic acid, pH 2.6, 0.1 M NaCl) was added to one set of plates without warming up and kept on ice. The remaining plates were then placed in a 37° C. water bath and 0.5 ml assay buffer pre-warmed to 37° C. was quickly added to cell monolayers to initiate internalization. After each time point, the plates were quickly placed on ice and the assay buffer was replaced with cold stop/strip solution. $^{125}$I-anti-HA IgG that remained on the cell surface was stripped by incubation of cell monolayers with cold stop/strip solution for a total of 20 minutes (0.75 ml for 10 minutes, twice) and counted. Cell monolayers were then solubilized with low-SDS lysis buffer and counted. The sum of $^{125}$I-anti-HA IgG that was internalized plus that remaining on the cell surface after each assay was used as the maximum potential internalization. The fraction of internalized $^{125}$I-anti-HA IgG after each time point was calculated and plotted.

Cell Surface DKK1 Binding and Immunodetection

Human DKK1 cDNA (clone MGC:868, IMAGE: 3508222) was obtained from Invitrogen and subcloned into pcDNA3 (EcoRI/XbaI). To facilitate immunodetection, a c-Myc epitope was included at the C-terminus. The integrity of the subcloned DNA sequence was confirmed by DNA sequencing. Human DKK1-conditioned media were produced by transient transfection of HEK293 cells with pcDNADKK1-Myc in serum-free medium, and allowed to bind to LRP6-transduced HT1080 cells and control cells at room temperature for 60 minutes in the absence or presence of 1 μM Mesd. Cells were then fixed in 4% paraformaldehyde, labeled with anti-Myc monoclonal antibody and detected with Alexa-488 goat anti-mouse IgG. The immunofluorescence was detected by a laser-scanning confocal microscope (Olympus Fluoview 500).

Cell Culture, Human Breast Cancer Tissue, Transfection, and Lentiviral Infections MDA-MB-231, MDA-MB-157, SKBR3, MCF-7, MDA-MB-435s, MDA-MB-361, HCC1187, HCC1143, HCC1806, HCC38, HCC1937, HCC1395, T-47D and CAMA1 breast cancer cell lines and MCF-10A non-transformed cells were all from the American Type Culture Collection (ATCC) and grown according to ATCC recommendations. MDA-MB-231-Luc cells were a kind gift from Dr. Katherine Weilbaecher (Washington University). Real-time PCR-based TissueScan™ Breast Cancer Disease Panels (OriGene) were used to screen for LRP6 expression. A breast cancer and normal tissue microarray containing 96 independent cores (Biomax) was used for LRP6 immunohistochemical staining (IHC). Human LRP6 was knocked down using LRP6-specific lentiviral shRNA (MISSION, Sigma-Aldrich). Virus was produced at the Viral Core Facility at Washington University and virus infection was performed as described (Stewart S A, et al. (2003) *RNA* 9: 493-501). Stably-transfected cells for in vivo studies were generated from heterogeneous pools of puromycin-resistant clones.

Construct and Nucleofection

In some experiments, LRP6 was subcloned into the mLRP4T100 backbone whose construction has been described previously (1). For rescue experiments, a codon-modified LRP6-Res construct was generated using the QuikChange Site-Directed Mutagenesis kit (Stratagene). The shRNA-targeted sequence was replaced with CTGAGGTG-TAAC (SEQ ID NO: 39), which does not change the amino acid composition of LRP6 but renders the construct insensitive to LRP6-specific shRNA. The modified LRP6 cDNA was confirmed by sequencing. LRP6-res construct was transfected into MDA-MB-231 cells using nucleofactor (Amaxa Biosystems, Cologne, Germany) according to the manufacturer's instructions.

Antibodies

The following antibodies were used in this study: LRP6 antibodies (Cell signaling; Abgent), β-catenin (BD Pharmingen), c-Myc and cyclin D1 (Santa Cruz), and actin antibodies (Sigma). They were used according to manufacturers' instructions. Polyclonal rabbit anti-Mesd antibody was produced by immunizing rabbits with purified Mesd protein. Horseradish peroxidase (HRP)-conjugated anti-rabbit and anti-mouse secondary antibodies were used (Amersham Pharmacia).

Quantitative Real-Time PCR

Real-time PCR-based TissueScan™ Breast Cancer Panel containing 48 tissues covering four disease stages and normal tissues (SA Biosciences) was used to evaluate LRP6 expression levels in human breast cancers. In these experiments, total RNAs isolated from breast cancer and control cells using Trizol (Invitrogen) and RNeasy Mini Kit (Qiagen) were reverse-transcribed with Superscript First-Strand Synthesis System (Invitrogen). The reaction mix was subjected to quantitative real-time PCR (qRT-PCR) to detect expression levels of LRP6 and other Wnt-related genes utilizing human qPCR primers specific for corresponding genes and RT$^2$ Profiler™ PCR Arrays (SABiosciences). Triplicate reactions were prepared using a 25-μl mixture containing Platinum SYBR Green qPCR Super Mix UDG (Invitrogen). Real-time quantification was performed on a Bio-Rad iCycle iQ system. Serial 10-fold dilutions of cDNA were used as references for the standard curve. Raw data were normalized to the endogenous actin expression.

Lentiviral Production

In some experiments, 293T cells were cotransfected with pLKO.1 or pLKO.1-LRP6 shRNA and packaging plasmids pHR'CVM8.2ΔR and pCMV-VSV-G using FuGENE 6 (Roche Diagnostics). The virus-containing supernatant was collected for infection of breast cancer cells. For stable cell line generation, cells were selected in growth medium containing 2 μg/ml puromycin.

Cell Growth, Cell Proliferation, and Soft Agar Tumorigenicity Assays

Cell growth and cell proliferation were measured by MTT assay (Promega) and BrdU incorporation using the BrdU ELISA kit (Roche Molecular Systems) according to the manufacturers' instructions. The colony formation ability of cancer cells was analyzed by soft agar assay, as follows. Breast cancer cells expressing control or LRP6 shRNA were seeded into 48-well plates. MTT-labeling reagent was added to each well 24 h later, and plates were incubated at 37° C. for 4 h. After the incubation period, the formazan crystals were dissolved in an MTT solubilization reagent and the resulting color was quantified spectrophotometrically. In some experiments, cell proliferation was measured by BrdU incorporation using the BrdU ELISA kit (Roche Molecular Systems) according to the manufacturer's instructions. Briefly, cancer cells expressing control or LRP6 shRNA were plated on 96-well plate. Cells were incubated with BrdU for 24 h, and the newly synthesized BrdU-DNA was then determined by colorimetry using an ELISA reader. All experiments were performed three times in triplicate.

Soft-Agar Tumorigenicity Assays

In some experiments, 1 mL bottom layer consisting of 1% agar medium was added to 6-well plates. MDA-MB-231 cells expressing control or LRP6 shRNA were trypsinized, centrifuged, resuspended in 0.5% agar medium (equal volumes of 1% agar and 2× culture medium), and plated at 1,000 cells/well as a top layer. Cells were incubated for 3 weeks at 37° C. until colony formation and colonies were stained with 0.5% crystal violet for counting.

Apoptosis Analysis

Apoptosis of cancer cells expressing control shRNA or LRP6 shRNA was detected using a TUNEL kit (Upstate) according to the manufacturer's protocol. Cells were counterstained with DAPI and examined by fluorescent microscopy. Dox-induced apoptosis was measured by Annexin V staining according to the manufacturer's protocol. In brief, cancer cells expressing LRP6 or control shRNA were treated with various concentration of Dox for 48 h. At the end of the treatment, cells were labeled with Annexin V conjugate (Annexin V, Molecular Probes) and propidium iodide (1 μg/ml, Sigma) for 30 minutes in 10 mmol/L HEPES, 140 mmol/L NaCl, 2.5 mmol/L CaCl$_2$. After washes, the apoptotic cells were assessed by fluorescence microscopy.

GST-E-Cadherin Pull-Down Assay

The GST-E-cadherin pulldown assay was performed as previously described (2). Cells expressing control or LRP6 shRNA were treated with L cells or Wnt3a-conditioned media (CM) for 4 h. Free β-catenin was determined using a GST-E-cadherin pull-down assay. Cells were lysed for 30 minutes at 4° C. Protein concentrations in lysates were quantified, and equal quantities of total proteins from different samples were incubated with GST-E-cadherin Sepharose beads for 4 h at 4° C. After incubation, the beads were washed three times and the bound proteins were eluted and separated via SDS-PAGE. Western blotting was performed using antibody to β-catenin.

Xenograft Tumor Model and Bioluminescent Imaging of Mice

Animal protocols were approved by the Animal Studies Committee of Washington University School of Medicine. Stable pool clones expressing control or LRP6 shRNA were generated in MDA-MB-231-Luc cells. Tumor xenografts were established by s.c. injection of $5 \times 10^5$ or $2 \times 10^6$ cancer cells into 6-week-old female BNX mice (Taconic). Bioluminescence imaging of tumors was performed as previously described using IVIS 100 (Caliper Life Sciences; exposure time, 1-60 sec; binning 8; fov 15 cm; f/stop 1; open filter) (Gross S, Piwnica-Worm D (2005) *Methods Enzymol* 399: 512-530). The first mouse images were obtained 24 h after s.c. inoculation of tumor cells. Total photon flux (photons per second) was determined from tumor region-of-interest (ROI) using LivingImage (Xenogen) and IgorPro (Wave metrics) image analysis software. Data were normalized by plotting as fold-enhancement on a given imaging day over bioluminescence on the first day. Tumor sizes were also measured with calipers.

Mesd Therapeutic Studies

Recombinant Mesd protein was prepared as described (Li Y, et al. (2005) *J Cell Sci* 118(22): 5305-5314). Mesd peptide, KGGGSKEKNKTKQDKGKKKKEGDLK-SKSSKEENRAGNK (SEQ ID NO: 14), was manufactured by Abgent (San Diego). Female athymic nude mice (Taconic) (6-8 weeks old) were used for passaging tumors from MMTV-Wnt1 mice (Taconic). MMTV-Wnt1 tumors were serially passaged in mice by implantation in the mammary fat pad as described (DeAlmeida V, et al. (2007) *Cancer Res* 67, 5371-5379). Therapeutic agents (200 μL Mesd protein, Mesd peptide or PBS) were administrated i.p. with a first dose of 15 mg/kg, followed by 10 mg/kg (9 more doses). Three groups of mice were treated every other day for three weeks and tumor volumes were measured thrice weekly.

Statistical Analysis

All quantified data represent an average of at least three independent experiments. Error bars represent mean±SD (or mean±SEM) as indicated in the figure legend. Statistical significance was determined by Student's t test, and $p < 0.05$ was considered significant.

Example 2

This example illustrates that Mesd binds to mature LRP5 AND LRP6 but not significantly to other members of the LDLR family.

To determine whether Mesd binds to other members of the LDLR family, $^{125}$I-Mesd binding analysis was performed with four groups of cells expressing different members of the LDLR family (FIG. 2). In the first experiment, HEK293 cells were transiently transfected with cDNAs for the LDLR, LRP5, LRP6 or empty pcDNA3 vector. In the second experiment, LRP-null Chinese hamster ovary (CHO) cells were stably transfected with LRP minireceptor mLRP4, LRP1B minireceptor mLRP1B4, apoER2, VLDLR, or empty pcDNA3 vector (Li, Y., et al., J. Biol. Chem. 275: 17187-17194, 2000; Li, Y., et al., J. Biol. Chem. 276: 18000-18006, 2001; Liu, C. X., et al., J. Biol. Chem. 276:28889-28896, 2001). mLRP4 is composed of residues 3274-4525 of the full-length LRP, which includes the fourth cluster of ligand-binding repeats and the entire C-terminus of the receptor. mLRP1B4 is composed of residues 3276-4599 of the full length LRP1B, which includes the fourth cluster of ligand binding repeats and the entire C-terminus of the receptor. mLRP4 and mLRP1B4 mimic the function and trafficking of LRP and LRP1B, respectively. In the third experiment, wild-type murine embryonic fibroblasts and murine embryonic fibroblasts with genetic deficiency of LDLR, LRP, or both (Willnow, T. E., et al., J. Cell Sci. 107: 719-726, 1994; Narita, M., et al., J. Biochem. 132: 743-749, 2002) were used. In the fourth experiment, the human breast cancer cell line MCF-7, human glioblastoma cell line U87, and human aortic smooth muscle cells (SMC) were used. MCF-7 cells express LRP at an undetectable level, whereas U87 cells and SMC express abundant LRP (Li, Y., et al., FEBS Lett. 555: 346-350, 2003). Interestingly, among the members of the LDLR family examined, only LRP5 specifically binds to Mesd, albeit at lower levels compared to LRP6 when these receptors were expressed at comparable levels (FIG. 2A). Although there is a suggestion of Mesd binding to LRP when examined in CHO and MEF cells (FIG. 2B,C), specific Mesd binding to U87 or SMC, both of which express abundant LRP, was minimal (FIG. 2D). Therefore, specific binding of Mesd to CHO and MEF cells may reflect endogenous LRP5/LRP6 in these cells.

As illustrated in FIG. 2, Mesd binds to mature LRP5 AND LRP6 but not significantly to other members of the LDLR family. (A) Binding of $^{125}$I-Mesd (5 nM) to HEK293 cells transient transfected with human HA-tagged LDLR, Myc-tagged LRP5, Myc-tagged LRP6 or control vector. Lower panel, western blot analysis for the expression of the LDLR, LRP5 and LRP6. Equal amounts of cell lysate were applied for each lane. (B) Binding of $^{125}$I-Mesd (5 nM) to LRP-null CHO cells stably transfected with LRP minireceptor mLRP4, LRP1B minireceptor mLRP1B4, VLDLR, apoER2 or empty pcDNA3 vector only. (C) Binding of $^{125}$I-Mesd (5 nM) to wild-type murine embryonic fibroblasts (MEF-1) or MEF cell lines genetically deficient in LRP (MEF-2), LDLR (MEF-3) or both (MEF-4). Lower panel, western blot analysis of LRP and the LDLR expression in MEF cell lines. (D) Binding of $^{125}$I-Mesd (5 nM) to human breast cancer and multiple myeloma (MM) cell line MCF-7, human glioblastoma cell line U87 and human aortic smooth muscle cells (SMC). Lower panel, western blot analysis of LRP expression in these cell lines. Assays were carried out for 4 hours at 4° C. in the absence (total) or presence of 500 nM Mesd. Values are the means of triple determinations with the s.d. indicated by error bars.

Example 3

This example illustrates that the carboxy-terminal region of Mesd is required for LRP6 folding.

Figure 3:
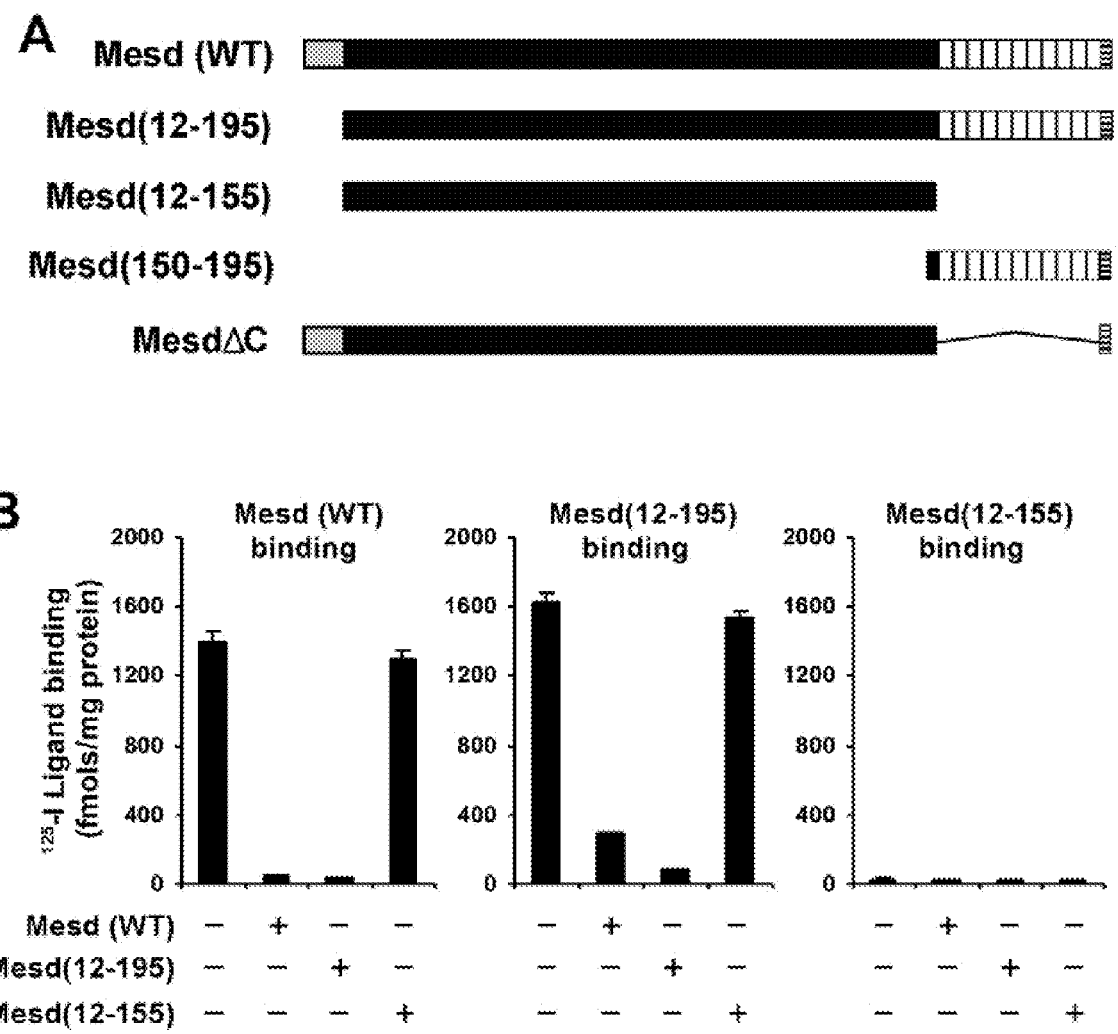
FIG. 3 illustrates that the C-terminal region of Mesd is required for interaction with LRP6.

To analyze the Mesd sequences that are required for Mesd to bind to mature LRP6 at the cell surface with high affinity, sequences were compared between mouse Mesd and its homologs from different species. It was found that the first 12 amino acids of mouse Mesd are absent in the nematode worms *Caenorhabditis elegans* and *Caenorhabditis briggsae*, and that mouse Mesd, as well as human Mesd, has an extra ~30 amino acid fragment prior to the conserved endoplasmic reticulum retention signal in its C-terminus (Culi, J., et al., Cell 112: 343-354, 2003; Hsieh, J. C., et al., Cell 112: 355-367, 2003). We thus generated two truncated Mesd mutants lacking either the N-terminal region, MESD (12-195), or both the N-terminal and C-terminal regions, Mesd (12-155) (FIG. 3A). The ability of these mutants to bind to cell surface LRP6 was then assessed. It was found that although truncation of the N-terminal 11 amino acids of mouse Mesd had no effect on LRP6 binding, further truncation of the last 40 amino acids completely abolished LRP6 binding (FIG. 3B).

Example 4

This example illustrates that 45 amino acids of Mesd are necessary and sufficient for binding to mature LRP6.

Figure 4:
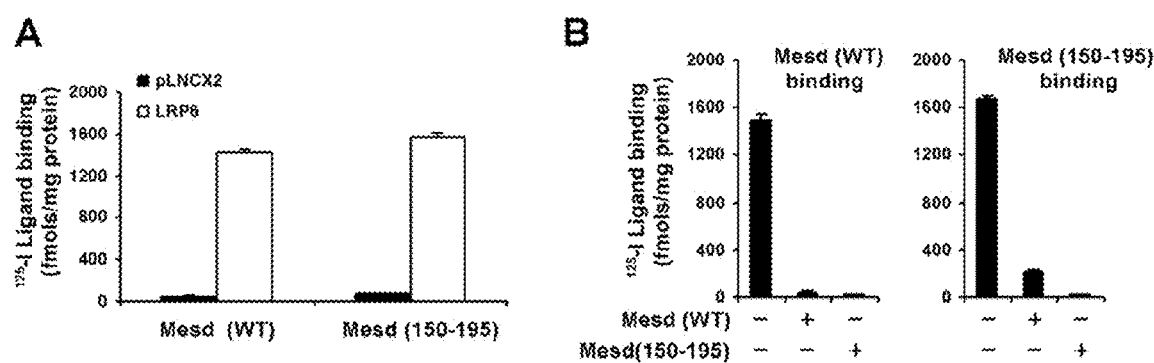
FIG. 4 illustrates that the C-terminal region of Mesd is necessary and sufficient for LRP6 binding.

In this example, a truncated Mesd mutant containing the last 45 amino acids of C-terminal region was generated (FIG. 3A) and its binding affinity for LRP6 was then analyzed. As shown in FIG. 4, The C-terminal region of Mesd is necessary and sufficient for LRP6 binding. (A) Binding analyses of $^{125}$I-Mesd and its mutant Mesd (150-195) (5 nM) to LRP6-transduced HT1080 cells and control cells. (B) Binding analyses of $^{125}$I-Mesd and its mutant Mesd (150-195) (5 nM) to LRP6-transduced HT1080 cells. Assays were carried out for 3 hours at 4° C. in the absence or presence of 500 nM Mesd or its mutant. Values are the means of triple determinations with the s.d. indicated by error bars.

Example 5

This example illustrates that the carboxy-terminal region of Mesd is required for LRP6 folding.

Figure 5:
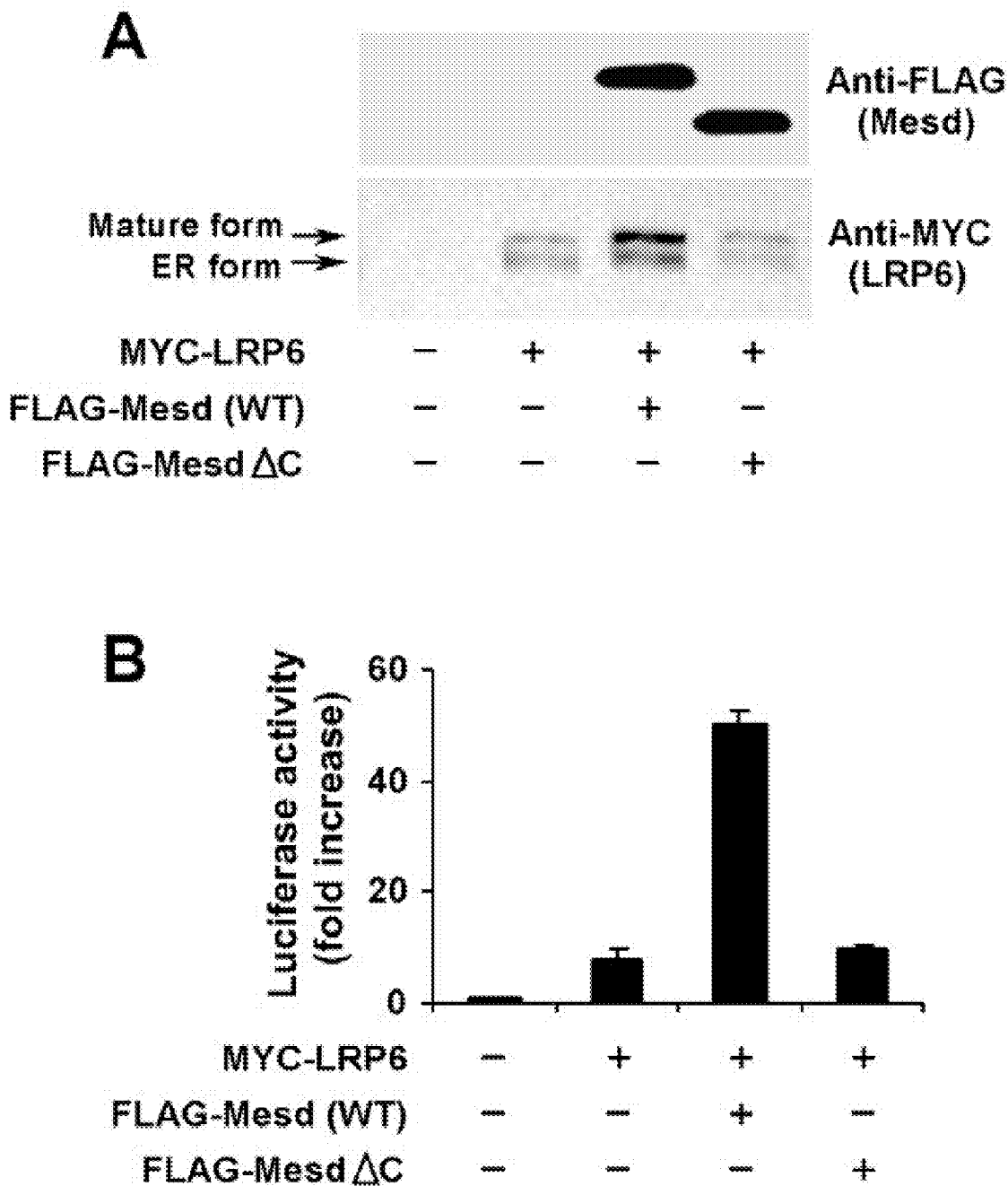
FIG. 5 illustrates that the carboxy-terminal region of Mesd is required for LRP6 folding.

To examine the role of this C-terminal region of Mesd on receptor folding, we generated a Mesd mutant (MesdΔC), which lacks the C-terminal region (amino acids 156-191) but retains the endoplasmic reticulum retention signal (REDL) (FIG. 3A). We next evaluated a potential role for MesdΔC on LRP6 folding. HEK293 cells were transiently transfected with cDNA for the LRP6 with cotransfection of control vector, or cDNAs for Mesd or MesdΔC. The steady-state levels of LRP6 were analyzed by western blotting with the anti-MYC antibody (FIG. 5A). As seen in the figure, two forms of the receptor, i.e. the ER form and mature form (containing complex sugar modifications), were seen for LRP6. In the presence of Mesd coexpression, but not of MesdΔC coexpression, the amount of the mature form of LRP6 was significantly increased (FIG. 5A). In FIG. 5A, HEK293 cells were transiently transfected with the indicated cDNAs. Cell lysates were analyzed by SDS-PAGE under reducing conditions and western blotted with anti-FLAG or anti-HA antibodies as indicated.

Activation of canonical Wnt signaling leads to the stabilization of β-catenin and regulation of gene transcription through transcription regulators including lymphoid-enhancing factor (LEF)-1 and T-cell factors (TCF). The TOP-FLASH luciferase reporter contains TCF-binding sites and can be directly activated by the β-catenin/TCF complex (Korinek, V., et al., Science 275:1784-1787, 1997). LRP6 is cell surface receptor, and only the mature receptor can reach the cell surface and modulate Wnt signaling (Cong, F., et al., Development 20: 5103-5115, 2004). We next examined the effect of MesdΔC on Wnt signaling using the TOP-FLASH luciferase reporter assay in HEK293 cells. As expected, Mesd coexpression, but not MesdΔC coexpression, significantly enhanced TCF/LEF transcriptional activity (FIG. 5B). In FIG. 5B, HEK293 cells were cotransfected with LRP6, MESD, MesdΔC or empty pcDNA3 vector and a TCF/LEF transcriptional activity reporter plasmid (TOP-FLASH). The luciferase activity was measured 48 hours after transfection. Values are the means of triple determinations with the s.d. indicated by error bars. Together, these results suggest that the C-terminal region of Mesd is required for LRP6 folding and its signaling function at the cell surface.

Example 6

This example illustrates that LRP6 is not a constitutively active endocytosis receptor and mediates a limited level of Mesd degradation.

Cell surface receptors that traffic between the plasma membrane and endocytic compartments contain signals within their cytoplasmic tails that allow for efficient recruitment into endocytic vesicles. In many cases (e.g. LRP and the LDLR), these signals are constitutively active and mediate continuous receptor endocytosis independently of ligand binding. To examine whether LRP6 is a constitutively active endocytosis receptor, kinetic analyses of receptor endocytosis with HT1080 cells transduced with HA-tagged LRP6 were performed. To eliminate potential effects of LRP6 ligands on its internalization, we utilized $^{125}$I-anti-HA IgG for LRP6 endocytosis assays. Binding of $^{125}$I-anti-HA IgG to HA-tagged LRP6 was specific, i.e. the binding of $^{125}$I-anti-HA IgG to the HT1080 control cells was minimal when compared to HT1080-LRP6 cells (FIG. 6A). We used HA-tagged LRP minireceptor mLRP4 as a positive control and mLRP4tailess (mLRP4 lacking the cytoplasmic tail) as a negative control for $^{125}$I-anti-HA IgG endocytosis (Li, Y., et al., J. Biol. Chem. 275: 17187-17194, 2000).

Figure 6:
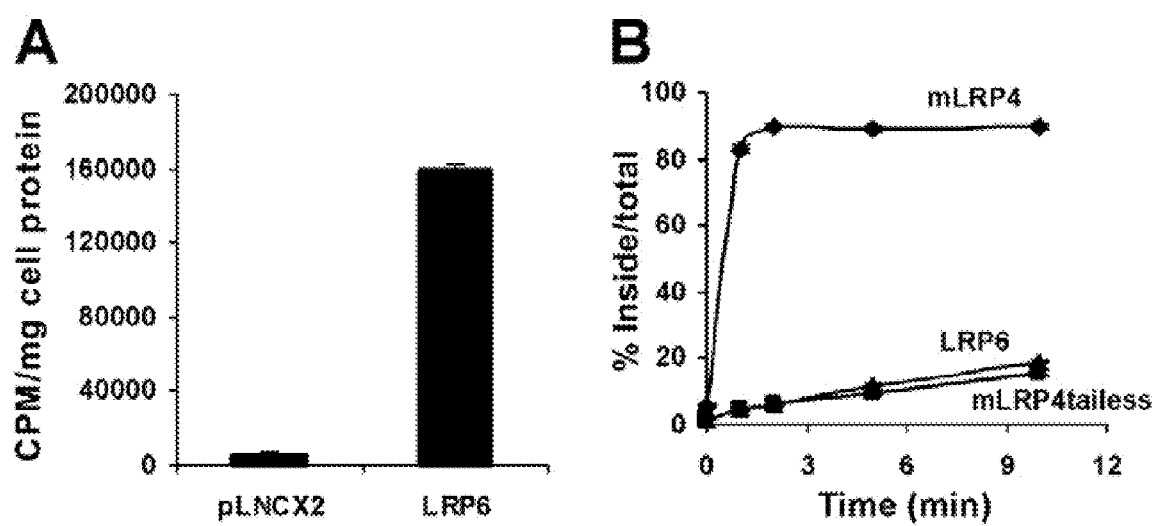
FIG. 6 illustrates that LRP6 is not a constitutively active endocytosis receptor.

FIG. 6 illustrates that LRP6 is not a constitutively active endocytosis receptor. (A) Anti-HA IgG binding to cell surface HA-tagged LRP6. Binding of $^{125}$I-anti-HA IgG (1 nM) to LRP6-transduced HT1080 cells and the control cells was carried out for 90 minutes at 4° C. (B) LRP6 endocytosis. LRP6-transduced HT1080 cells, mLRP4-transfected CHO cells and mLRP4tailess-transfected CHO cells were incubated with 1 nM $^{125}$I-anti-HA IgG at 4° C. for 90 minutes, and then incubated at 37° C. for the indicated times. The amount of internalized anti-HA IgG was determined. Values are the means of triple determinations with the s.d. indicated by error bars. Interestingly, we found that the endocytosis rate of LRP6 was extremely slow, and was indistinguishable from that of mLRP4tailess (FIG. 6B), indicating that LRP6 itself is unable to initiate endocytosis. From these data, it was concluded that LRP6 is not a constitutively active endocytosis receptor and mediates a limited level of Mesd degradation.

Example 7

This example illustrates that LRP6 mediates little Mesd uptake and degradation.

Figure 7:
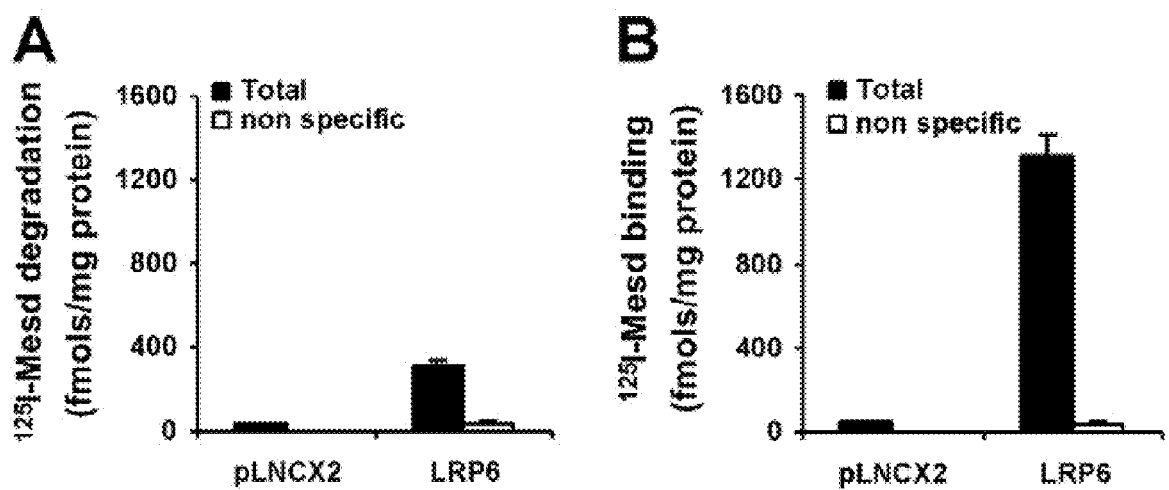
FIG. 7 illustrates that LRP6 exhibits a limited level of Mesd degradation.

LRP6-mediated Mesd uptake and degradation was investigated in the experiments illustrated in FIG. 7. (A) LRP6-mediated $^{125}$I-Mesd (5 nM) degradation in LRP6-transduced HT1080 cells and control cells was carried out for 4 hours at 37° C. in the absence or presence of 500 nM Mesd. (B) $^{125}$I-Mesd (5 nM) binding to LRP6-transduced HT1080 cells and the control cells was carried out for 4 hours at 4° C. in the absence or presence of 500 nM Mesd. Values are the means of triple determinations with the s.d. indicated by error bars. As shown in FIG. 7, HT1080 cells transduced with LRP6 exhibited $^{125}$I-Mesd degradation at a level of 320 fmoles/mg cell protein after 4 hours of incubation at 37° C., whereas $^{125}$I-Mesd binding following 4 hours of incubation at 4° C. was detected at a level as high as 1320 fmoles/mg cell protein. These results indicate that Mesd binding to LRP6 at the cell surface does not trigger significant endocytosis, and consequently little Mesd uptake and degradation can be detected.

Example 8

This example illustrates that Mesd binding to the cell surface LRP6 does not significantly change the cytosolic β-catenin level.

β-catenin is a key molecule in the Wnt/β-catenin signaling pathway. A cytosolic pool of β-catenin interacts with DNA-binding proteins and participates in Wnt signal transduction (Hinck, L., J. Cell Biol. 125: 1327-1340, 1994; Gottardi, C. J., J. Cell Biol. 153: 1049-1060, 2001; Klingelhofer, J., et al., Oncogene 22: 1181-1188, 2003). To determine whether Mesd binding to cell surface LRP6 directly regulates Wnt signaling, we studied the effects of Mesd binding on cytosolic β-catenin levels in HT1080-LRP6 cells. In these experiments, LRP6-transduced HT1080 cells were treated with 0.5 to 5 nM Mesd for 2 hours at 37° C., and cytosolic β-catenin levels were examined by western blotting using an anti-β-catenin antibody. We found that there was no significant change in the cytosolic β-catenin levels upon Mesd treatment (data not shown). The results indicate that Mesd binding to cell surface LRP6 does not directly modify Wnt signaling.

Example 9

This example illustrates that RAP binds to LRP6 and partially competes for Mesd binding.

Receptor-associated protein (RAP) binds with high affinity to LRP, megalin, VLDLR and apoER2, and with a lower affinity to the LDLR (Bu, G., Int. Rev. Cytol. 209, 79-116. 2001). To determine whether RAP and Mesd bind to identical, overlapping, or different sites on the receptors, we performed binding and competition analysis of these two chaperones with HT1080 cells stably expressing LRP6. As shown in FIG. 8, to determine whether RAP also binds LRP6, we performed RAP-binding analysis with HT1080 cells stably expressing LRP6 at 4° C. Control cells, expressing vector alone, exhibited a moderate level of cell surface $^{125}$I-RAP binding, probably mediated by cell surface heparan sulfate proteoglycan and endogenous receptors of the LDLR family. The presence of excess unlabeled RAP (500 nM), but not Mesd (500 nm), completely eliminated this binding (FIG. 8A). Compared to the control cells, LRP6 expressing HT1080 cells displayed ~20% increase of RAP binding, and this increase was abolished by excess unlabeled Mesd (FIG. 8A). These results suggest that RAP binds to cell surface LRP6 with a relatively low affinity.

We performed binding of 5 nM $^{125}$I-Mesd (5 nM) to cell surface LRP6 in the presence of various concentrations of excess unlabeled RAP or 500 nM unlabeled Mesd (FIG. 8B). RAP inhibited $^{125}$I-Mesd binding in a dose-dependent manner with ~60% inhibition achieved with 500 nM RAP, whereas the same concentration of unlabeled Mesd inhibited >90% of $^{125}$I-Mesd binding (FIG. 8B). When $^{125}$I-Mesd (5 nM) uptake and degradation were performed, 500 nM unlabeled Mesd completely, whereas 500 nM unlabeled RAP only partially, inhibited $^{125}$I-Mesd degradation (FIG. 8C). Together, these results suggest that Mesd and RAP probably bind to different, but perhaps adjacent sites on LRP6. The lower affinity of RAP to cell surface LRP6 may also contribute to its lower efficiency in inhibition of Mesd binding.

In FIG. 8A, binding of $^{125}$I-RAP (5 nM) to LRP6-transduced HT1080 cells and the control cells was carried out for 4 hours at 4° C. in the absence (total) or presence of 500 nM RAP, or 500 nM Mesd. In FIG. 8B, binding of $^{125}$I-Mesd (5 nM) to LRP6-transduced HT1080 cells was carried out for 2 hours at 4° C. in the absence (total) or presence of various concentrations of RAP or 500 nM Mesd. (C) LRP6-mediated $^{125}$I-Mesd (5 nM) degradation was carried out for 4 hours at 37° C. in the absence or presence of 500 nM Mesd or 500 nM RAP. Values are the means of triple determinations with the s.d. indicated by error bars.

These experiments illustrate that RAP binds to LRP6 and partially competes for Mesd binding.

Example 10

This example illustrates that Mesd antagonizes ligand binding to LRP6 at the cell surface.

Figure 9:
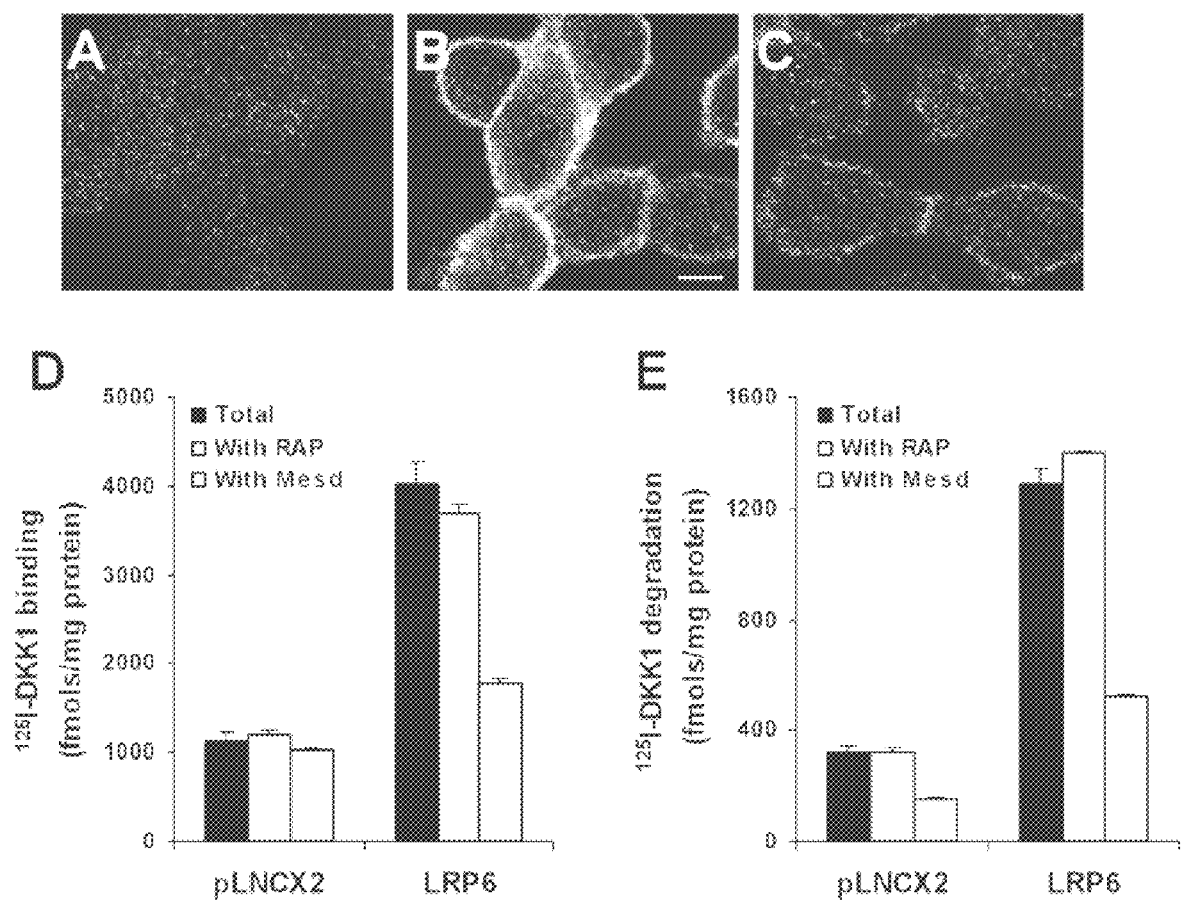
FIG. 9 illustrates that Mesd inhibits DKK1 binding to LRP6.

RAP is a receptor antagonist for members of the LDLR family, and is able to inhibit the binding of most known ligands of the LDLR family members. DKK1 is an LRP6-specific ligand and antagonist. To determine whether Mesd is also able to block LRP6 ligand binding, we examined cell surface DKK1 binding by immunostaining As illustrated in FIG. 9, Myc-tagged DKK1 binds to LRP6 cells (FIG. 9B) but not to the control cells (FIG. 9A). The presence of Mesd completely blocked the binding of Myc-DKK1 to LRP6 at the cell surface (FIG. 9C). In these experiments, Serum-free conditioned medium was harvested from HEK293 cells transiently transfected with cDNA for human Myc-DKK1 and allowed to bind to LRP6-transduced HT1080 cells (B,C) and control cells (A) in the absence (A,B) or presence (C) of 1 µM Mesd. Cell-surface-bound Myc-tagged DKK proteins were fixed and detected by immunofluorescence staining with anti-Myc antibody. (D) DKK1 binding to cell surface LRP6 is inhibited by Mesd. Binding of 125I-DKK1 (5 nM) to LRP6-transduced HT1080 cells or the control cells was carried out for 3 hours at 4° C. in the absence (total) or presence of 500 nM RAP or 500 nM Mesd. (E) LRP6-mediated DKK1 degradation is inhibited by Mesd. LRP6-mediated $^{125}$I-Mesd (5 nM) degradation was carried out for 4 hours at 37° C. in the absence or presence of 500 nM RAP or 500 nM Mesd. Values are the means of triple determinations with the s.d. indicated by error bars. Bar, 10 µm. As expected, Myc-tagged DKK1 binds to LRP6 cells (FIG. 9B) but not to the control cells (FIG. 9A). Importantly, the presence of Mesd completely blocked the binding of Myc-DKK1 to LRP6 at the cell surface (FIG. 9C).

To confirm the above results, we examined the binding and degradation of $^{125}$I-DKK1. LRP6-expressing HT1080 cells exhibited significantly higher levels of $^{125}$I-DKK1 binding and degradation than the control cells. The increased DKK1 binding and degradation were abolished by excess unlabeled Mesd, but not by excess unlabeled RAP (FIG. 9D,E). Together, these results indicate that Mesd can specifically block DKK1 binding to LRP6 at the cell surface.

To confirm the above results, we examined the binding and degradation of $^{125}$I-DKK1. LRP6-expressing HT1080 cells exhibited significantly higher levels of $^{125}$I-DKK1 binding and degradation than the control cells. The increased DKK1 binding and degradation were abolished by excess unlabeled Mesd, but not by excess unlabeled RAP (FIG. 9D,E). Together, these results indicate that Mesd can specifically block DKK1 binding to LRP6 at the cell surface.

Example 11

This example illustrates binding of Mesd polypeptide or an Mesd oligopeptide to LRP5 and LRP6.

Figure 10:
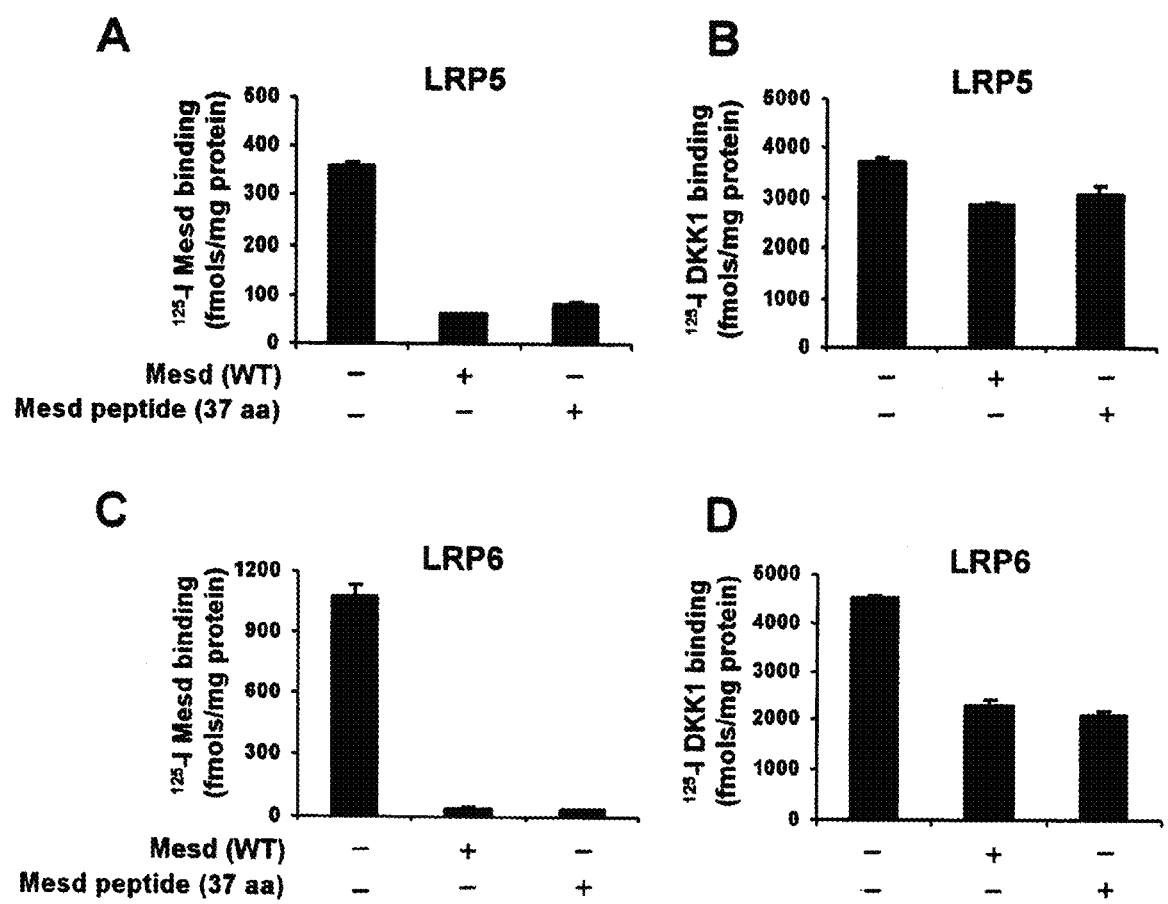
FIG. 10 illustrates that Mesd polypeptide or a Mesd oligopeptide can both bind LRP5 and inhibit binding of DKK1 to either LRP5 or LRP6.

In order to investigate the binding of Mesd polypeptide and an Mesd oligopeptide to either LRP5 or LRP6, binding assays were performed using $^{125}$I-Mesd or $^{125}$I-DKK1 (FIG. 10). FIG. 10A shows that both wild type Mesd and Mesd oligopeptide KGGGSKEKNKTKPEKAKKKEGDPK-PRASKEDNRAGSR (SEQ ID NO: 20) can reduce binding of $^{125}$I-Mesd to LRP5 up to about 10-fold, while FIG. 10C shows that both Mesd and the oligopeptide show even greater reduction of binding of $^{125}$I-Mesd to LRP6. In addition, in binding assays using $^{125}$I-DKK1, a small but significant reduction in binding of $^{125}$I-DKK1 to LRP5 was observed when the LRP5 was contacted with either Mesd or the oligopeptide (FIG. 10B), while binding of $^{125}$I-DKK1 greater than 2-fold was observed when LRP6 was the target (FIG. 10D).

These data demonstrate that both Mesd polypeptide, and the oligopeptide of sequence SEQ ID NO: 19 can both bind LRP5 and inhibit binding of DKK1 to either LRP5 or LRP6.

Example 12

This example illustrates inhibition of WNT signalling in HEK293 cells.

Figure 11:
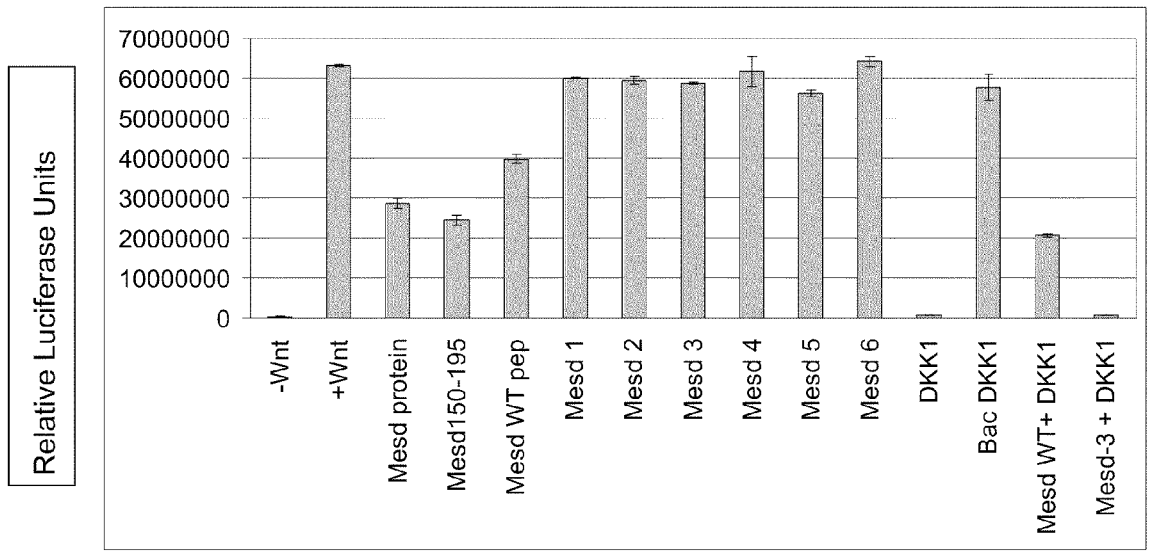
FIG. 11 shows results from HEK293 cells stably transfected with TCF/LEF-luc reporter.

In this example, Wnt signaling was measured in HEK293 cells comprising TCF/LEF-Luc assays in cells were prepared as described above, and subjected to the treatments as shown in Table IV, with the results (i.e., luciferase activity) presented in FIG. 11. In these experiments, transfected cells were treated without Wnt-3A or with Wnt-3A plus the indicated inhibitors (Mesd and/or Dkk1) for 16 hours at 37° C. Wnt signaling was measured by quantifying the luciferase activity using a live cell imaging system.

TABLE IV

| Column | Treatment |
|---|---|
| 1 | L cell control medium |
| 2 | Wnt3A conditioned medium |
| 3 | Wnt3A conditioned medium plus 500 nM Mesd protein |
| 4 | Wnt3A conditioned medium plus 500 nM Mesd (150-195) peptide QMYPGKGGGSKEKNKTKPEKAKKKEGDPKPRASKEDNRAGSRREDL (SEQ ID NO: 22) |
| 5 | Wnt3A conditioned medium plus 500 nM Mesd WT peptide KGGGSKEKNKTKPEKAKKKEGDRKPRASKEDNRAGSR (SEQ ID NO: 21) |
| 6 | Wnt3A conditioned medium plus 500 nM Mesd peptide KGGGSKEKNKTKPEKAKKK (SEQ ID NO: 26) (mouse Mesd-13) |
| 7 | Wnt3A conditioned medium plus 500 nM Mesd peptide EGDRKPRASKEDNRAGSR (SEQ ID NO: 24) (mouse Mesd-1 1) |
| 8 | Wnt3A conditioned medium plus 500 nM Mesd peptide TKPEKAKKKEGDRKPRAS (SEQ ID NO: 27) (mouse Mesd-14) |
| 9 | Wnt3A conditioned medium plus 500 nM Mesd peptide KGGGSKEKNK (SEQ ID NO: 9) (Mesd-4) |
| 10 | Wnt3A conditioned medium plus 500 nM Mesd peptide KEDNRAGSR (SEQ ID NO: 28) (mouse Mesd-15) |
| 11 | Wnt3A conditioned medium plus 500 nM Mesd peptide KEKNKTKPEK (SEQ ID NO: 29) (mouse Mesd-16) |
| 12 | Wnt3A conditioned medium plus Dkk1 protein at 10 nM |
| 13 | Wnt3A conditioned medium plus bacterially expressed Dkk1 at 10 nM |
| 14 | Wnt3A conditioned medium plus Dkk1 protein at 10 nM plus Mesd WT |
| 15 | Wnt3A conditioned medium plus Dkk1 protein at 10 nM plus Mesd-3 |

The data indicate that Mesd protein, Mesd (150-195) peptide, and Mesd WT peptide moderately inhibit Wnt signaling and can be used for Wnt-related cancer therapy, although Dkk1 is a more potent inhibitor. Because Mesd is also an inhibitor of Dkk1, it will have dual benefits, i.e. reducing cancer and increasing bone health.

Example 13

Figure 12:
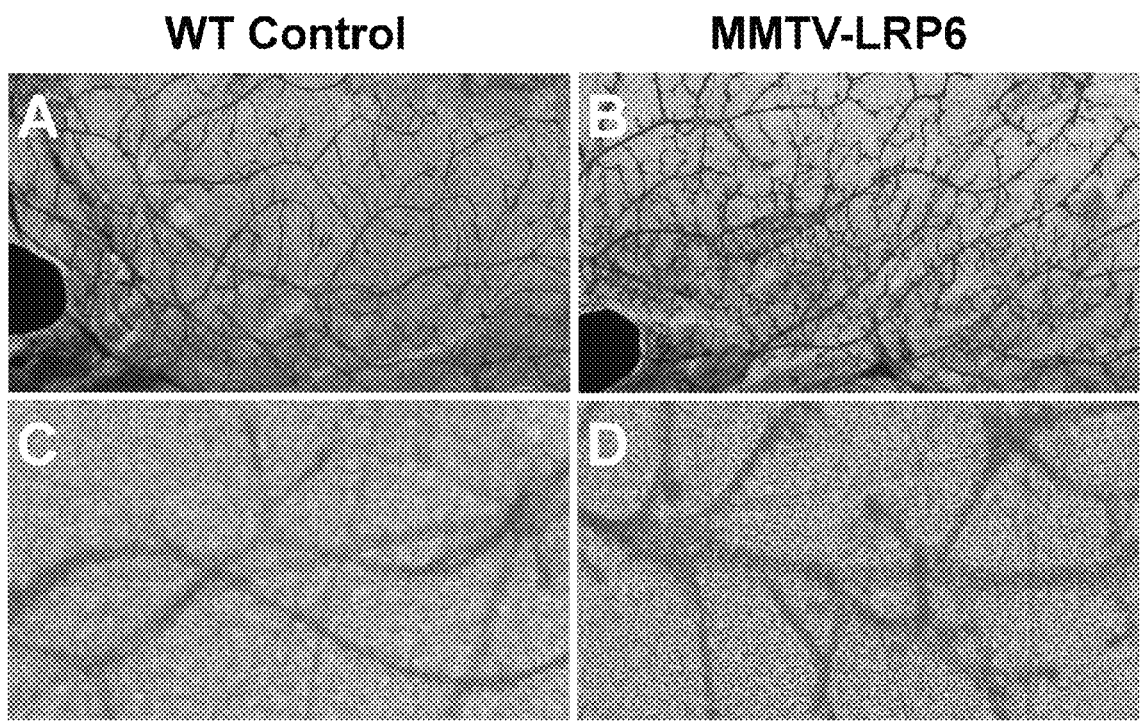
FIG. 12 shows mammary gland hyperplasia in an MMTV-LRP6 transgenic mouse.

To generate the MMTV-LRP6 construct, human LRP6 cDNA was cloned into the MMTV-SV40-Bssk vector, between the murine mammary tumor virus long terminal repeat (MMTV-LTR) and an SV40 large T antigen intron and polyadenylation signal. Prior to injection, the construct was linearized and purified. Transgenic mice were generated in the FVB/N inbred background and transgenic founders were identified by PCR testing for the presence of the transgene. Four founders were obtained and their offspring were characterized for the expression of LRP6, extent of Wnt signaling, and mammary gland morphology by whole mount staining MMTV-LRP6 transgenic mice were generated for overexpression of LRP6 cDNA in the mammary epithelial cells, as driven by the MMTV promoter. As shown in FIG. 12, mammary glands from littermates of either WT (panels A, C) or MMTV-LRP6 virgin mice (panels B, D) at 14 weeks of age were analyzed by whole mount staining Note mammary hyperplasia in MMTV-LRP6 mice (panel B at low power field and D at high power field).

Example 14

This example illustrates that LRP6 expression is frequently up-regulated in human breast cancer. To explore the role of LRP6 in breast cancer, the expression of LRP6 in human breast cancer tissues was analyzed using a real-time PCR-based tissue array.

In these experiments, a breast cancer TissueScan Real-Time qPCR array, containing 7 normal/Stage 0 cDNAs and 41 human breast cancer cDNAs, was analyzed for LRP6 expression by real-time PCR. Averages of relative LRP6 expression from 3 independent plates were plotted with clinical status indicated. As shown in FIG. 13A, LRP6 mRNA levels are markedly up-regulated in a subset of human breast cancer tissues. "#" designates samples with elevated HER2 transcripts. In some experiments, a breast cancer tissue microarray was used for IHC staining of LRP6. FIG. 13B presents representative LRP6 staining in normal and malignant breast tissue. LRP6 antibody (C-term T1546, Abgent), which specifically recognizes human LRP6, was used for IHC staining FIG. 13C presents quantification of LRP6 IHC staining as determined from three independent experiments. Staining intensity was scored as absent (0), weak (1), moderate (2) or strong (3). Four observations were made on each slide by independent investigators, and a mean score was recorded. Expression of LRP6 in human mammary epithelial cell (MCF-10A) was analyzed in indicated breast cancer cell lines by Western blot (FIG. 13D). *p<0.05; **p<0.01.

Figure 18:
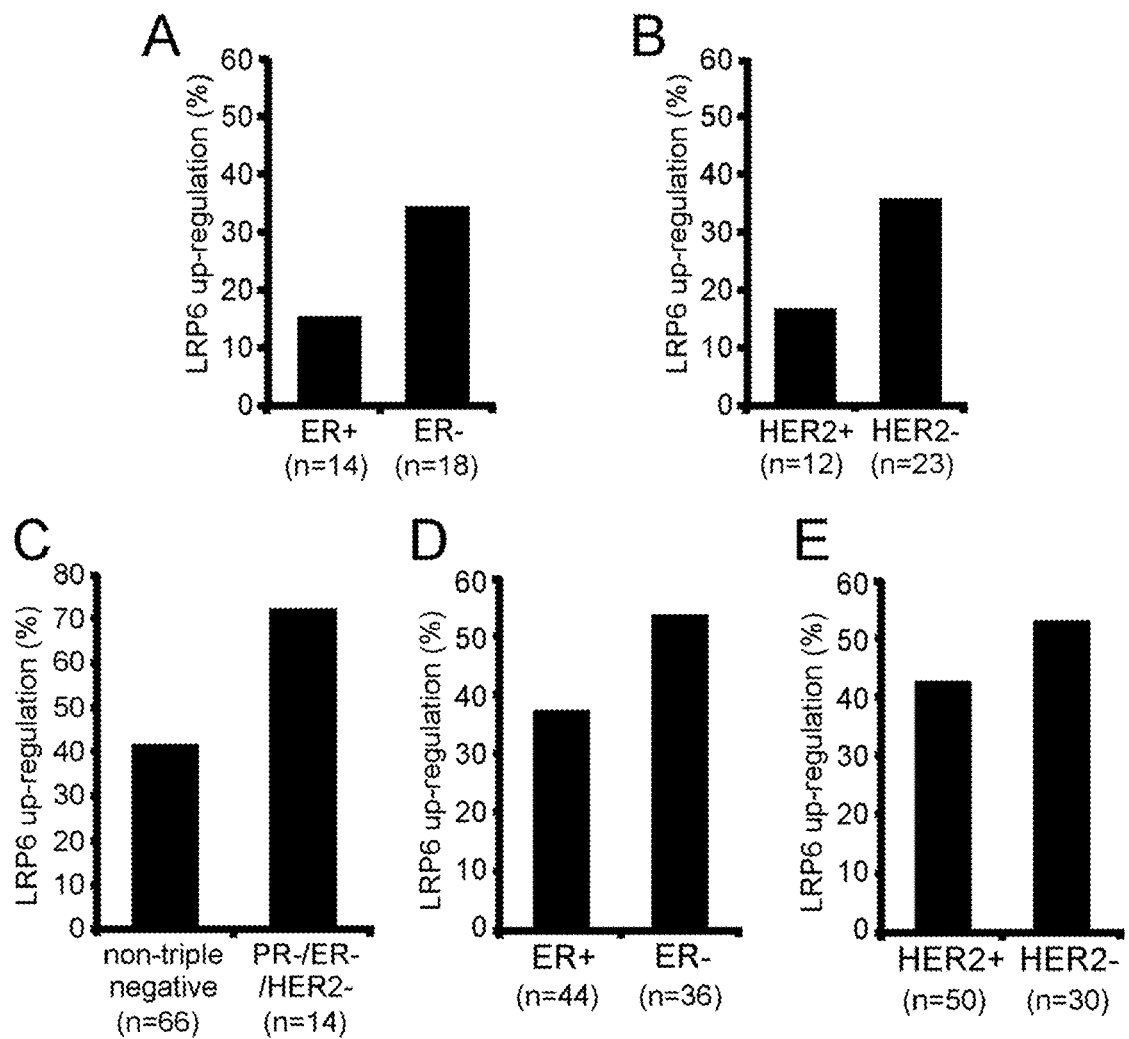
FIG. 18 illustrates that LRP6 expression is up-regulated more frequently in ER-, HER2-, or triple-negative human breast tumors.

Of 41 breast cancer cases with disease stages ranging from Stage I to IIIC, 10 exhibited significant increases in LRP6 transcripts compared to normal mammary tissues (FIG. 13A). LRP6 was up-regulated more frequently in ER- or HER2-negative tissues (FIG. 18 A-B). In these experiments, TissueScan Real-Time Breast Cancer Disease Panels (OriGene) was used for real-time PCR to quantify LRP6 transcripts. Breast tumors with up-regulated LRP6 expression were analyzed against ER and HER2 status. Note that LRP6 is up-regulated more frequently in ER- or HER2-negative breast tumors.

Figure 19:
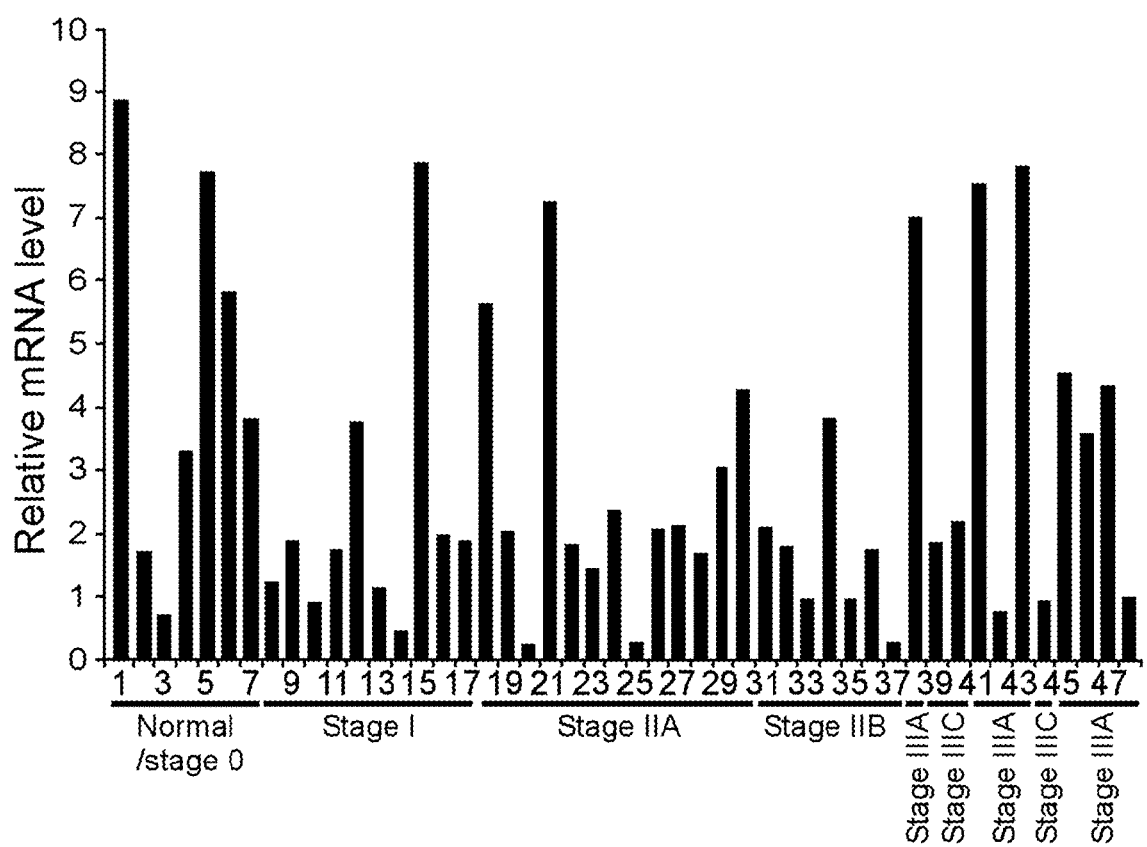
FIG. 19 illustrates expression of LRP5 in human breast cancer tissues.

Further studies investigated only the role of LRP6 in breast cancer tumorigenesis in human breast cancer tissues, primarily because no significant up-regulation of LRP5 was observed (FIG. 19). In these experiments, a breast cancer TissueScan Real-Time qPCR array, containing 7 normal/Stage 0 cDNAs and 41 human breast cancer cDNAs, was analyzed for LRP5 expression by real-time PCR. There is no significant change in LRP5 expression between normal mammary tissues and breast cancer tissues.

Figure 13:
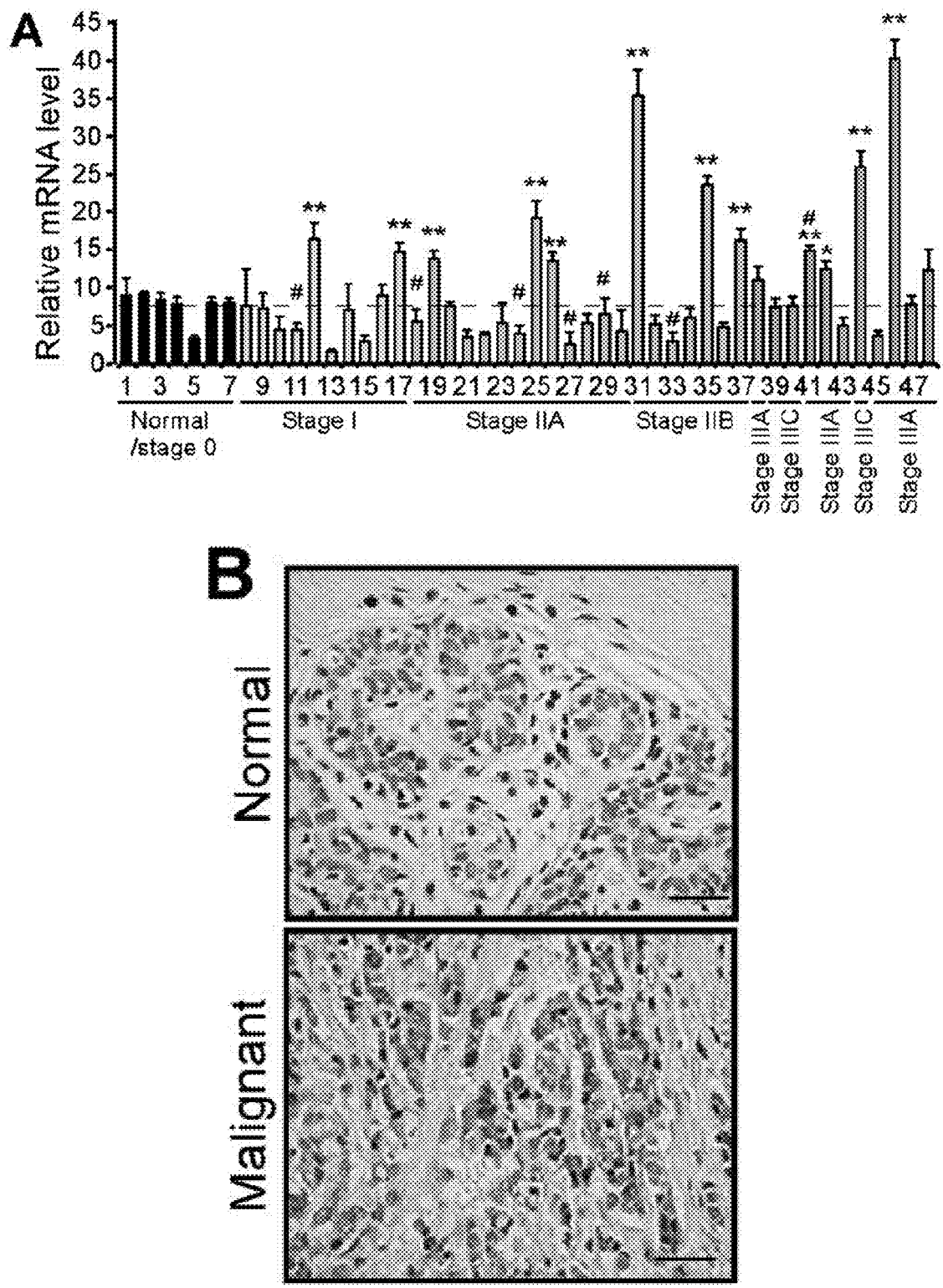
FIG. 13 illustrates up-regulation of LRP6 expression in a subset of human breast cancer tissues and cell lines.

Immunostaining was used to analyze LRP6 expression levels in a tissue array containing common types of breast carcinoma and non-malignant mammary tissues. The specificity of LRP6 immunostaining was first confirmed in control and LRP6 knocked down (1(D) tumor tissues derived from MDA-MB-231 cells (See FIG. 16H). Moderate to strong staining for LRP6 was observed in subsets of breast carcinomas, resulting in higher mean scores compared to normal/benign tumor tissues (FIG. 13 B-C).

FIG. 18 C-E further illustrate that LRP6 is up-regulated more frequently in triple-negative, ER- or HER2-negative tumors. In these experiments, a breast cancer tissue microarray (Biomax) was used for immunohistochemistry staining of LRP6, and the quantification of staining was evaluated as described in FIG. 13C. Breast tumors with up-regulated LRP6 expression were analyzed against ER and HER2 status. Note that LRP6 expression is up-regulated more frequently in ER, HER2-negative, or ER/PR/HER2-triple-negative breast tumors.

To further investigate LRP6 expression in breast cancer, 14 human breast cancer cell lines (9 ER-negative and 5 ER-positive) were examined using SuperArray to profile the expression of 84-Wnt-related genes, including LRP5, LRP6 and several Wnt target genes. LRP6 expression is >6-fold higher in 7 of 14 breast cancer cell lines compared to non-transformed MCF-10A cells (Table V). Furthermore, LRP6 was overexpressed at the protein level in 6 of 12 breast cancer cell lines (FIG. 13D).

Together, these results demonstrate that up-regulation of LRP6 expression is a common event among defined subsets of human breast cancers.

TABLE V

Wnt-related Gene Expression in Human Breast Cancer Cell Lines by Real-Time PCR-Based SuperArray Analysis

| Cell line | LRP6 | LRP5 | Dkk1 | MYC | CCND1 | ER status |
|---|---|---|---|---|---|---|
| MDA-MB-157 | 0.35 | 1.15 | 9.85 | 4.92 | 0.29 | − |
| MDA-MB-231 | 9.22 | 5.85 | 78.64 | 43.35 | 12.66 | − |
| HCC1143 | 7.46 | 2.46 | 0.20 | 34.30 | 17.15 | − |
| HCC1806 | 6.06 | 7.46 | 11.31 | 18.38 | 4.59 | − |
| HCC38 | 6.06 | 2.83 | 2.46 | 13.00 | 0.41 | − |

TABLE V-continued

Wnt-related Gene Expression in Human Breast Cancer Cell Lines by Real-Time PCR-Based SuperArray Analysis

| Cell line | LRP6 | LRP5 | Dkk1 | MYC | CCND1 | ER status |
|---|---|---|---|---|---|---|
| HCC1187 | 25.99 | 6.06 | 0.27 | 36.76 | 8.57 | − |
| SKBR3 | 0.10 | 6.96 | 2.46 | 42.22 | 0.71 | − |
| HCC1937 | 4.57 | 6.00 | 16.53 | 12.31 | 2.83 | − |
| MDA-MB-435s | 1.23 | 0.57 | 4.29 | 4.29 | 0.44 | − |
| MDA-MB-361 | 9.20 | 6.34 | 0.64 | 5.30 | 4.37 | + |
| HCC1395 | 6.62 | 12.03 | 0.72 | 11.19 | 0.45 | + |
| T-47D | 1.71 | 6.28 | 0.63 | 5.93 | 1.84 | + |
| CAMA1 | 1.74 | 9.85 | 0.13 | 19.70 | 2.83 | + |
| MCF-7 | 3.03 | 4.92 | 22.63 | 21.11 | 6.06 | + |

Numbers represent fold changes compared to the gene expression levels in non-transformed MCF-10A cells.

Example 15

This example illustrates that down-regulation of LRP6 in breast cancer cells attenuates Wnt/β-catenin signaling and inhibits cell proliferation.

Figure 14:
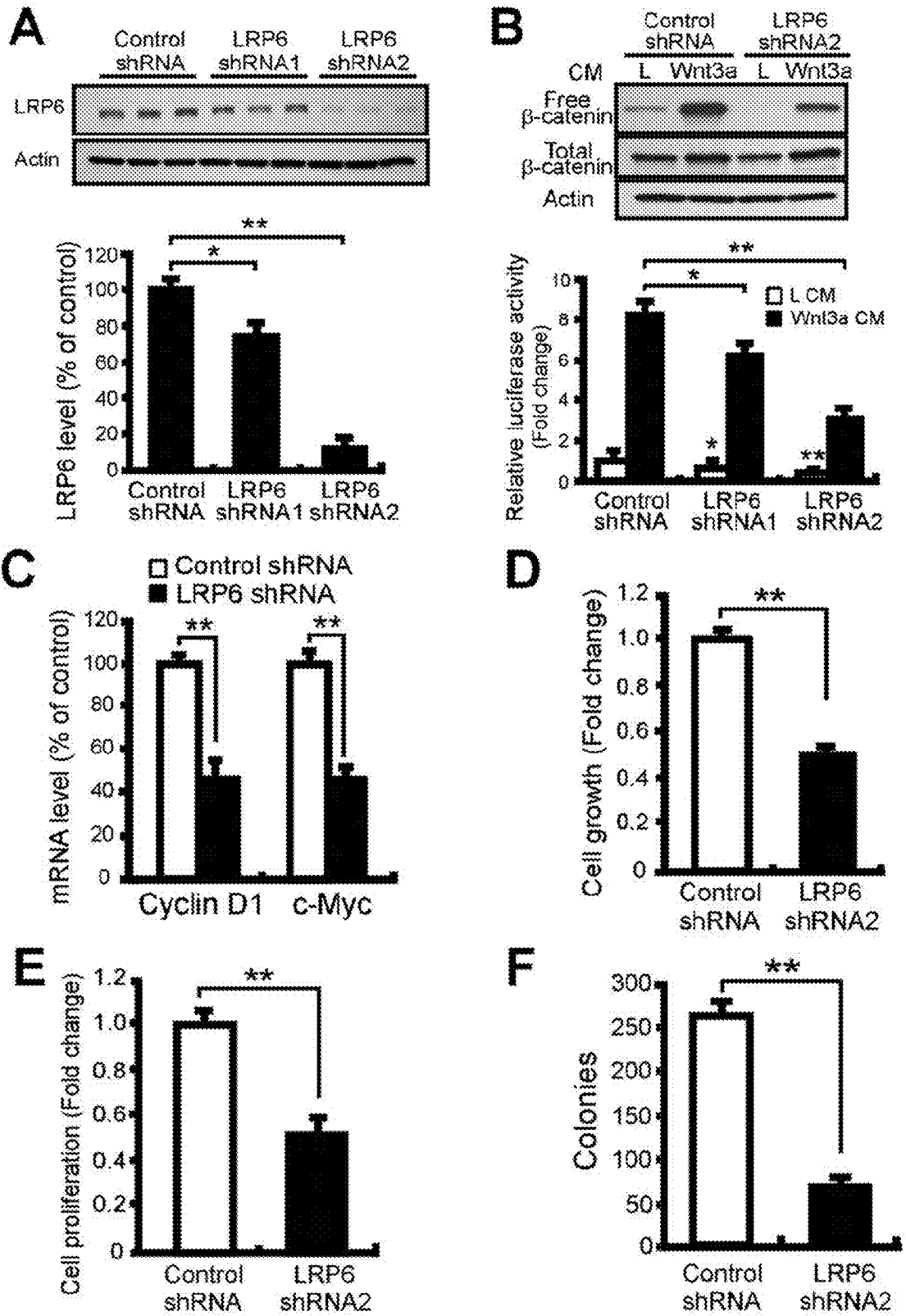
FIG. 14 illustrates decreased Wnt signaling, breast cancer cell viability, proliferation and colony formation in knockdown of LRP6 in MDA-MB-231 breast cancer cells.

In these experiments, MDA-MB-231 cells were transduced with lentivirus expressing control or LRP6 shRNA. Cells were then subjected to the indicated analysis 48 h post infection, as shown in FIG. 14.

FIG. 14A: Western blot and densitometric analysis show that both LRP6 shRNAs reduce LRP6 expression in MDA-MB-231 cells compared to the control shRNA. FIG. 14B: LRP6 down-regulation inhibited Wnt3a-induced accumulation of free β-catenin and Topflash reporter activity. Data are expressed as fold changes normalized to that from cells expressing control shRNA in the presence of L CM. FIG. 14C: Quantitative real-time PCR shows that expression of Wnt target genes (Cyclin D1 and c-Myc) was down-regulated in cancer cells expressing LRP6 shRNA2. FIG. 14D: Cell viability in LRP6-KD cells was assessed by MTT assay. FIG. 14E: Proliferation of breast cancer cells expressing LRP6 shRNA2 was suppressed by ~50% as measured by BrdU incorporation. FIG. 14F: Soft agar colony formation assay demonstrating reduced colony formation when LRP6 expression was knocked down. Data are mean±SD from 3 independent experiments. *p<0.05; ** p<0.01.

Figure 20:
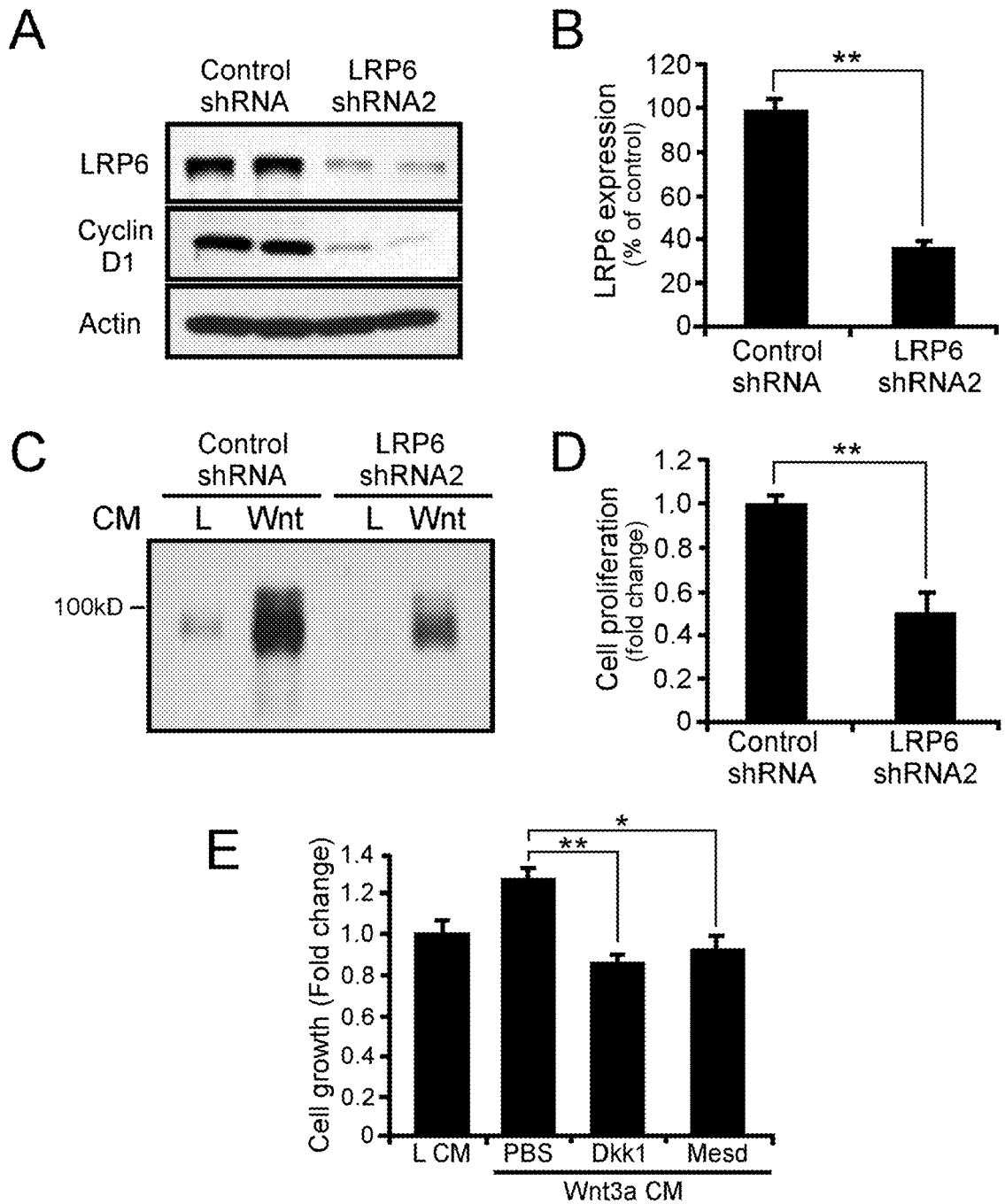
FIG. 20 illustrates decreased Wnt signaling and cell proliferation in knockdown of LRP6 in HCC1187 breast cancer cells.

In some experiments, the effects of modulating LRP6 expression on Wnt signaling and tumorigenesis in breast cancer cells were examined. Using two independent lentiviral shRNAs targeting distinct regions of LRP6, LRP6 expression in MDA-MB-231 (FIG. 14A and FIG. 21A) and HCC1187 cells (FIG. 20 A-B) was knocked down. These two cell lines display relatively high levels of endogenous LRP6. In these experiments, we show that knockdown of LRP6 in HCC1187 breast cancer cells decreases Wnt signaling and cell proliferation. FIG. 20A: Western blot analysis of LRP6 knockdown by lentiviral shRNA. FIG. 20B: Densitometric analysis of Western blots from triplicate samples in FIG. 20A.

FIG. 21 illustrates effects of LRP6 knockdown on apoptosis and soft agar colony formation in MDA-MB-231 breast cancer cells. In some experiments, effects of LRP6 knockdown on apoptosis and soft agar colony formation in MDA-MB-231 breast cancer cells were studied using quantitative real-time PCR (FIG. 21A). The results show a reduction of LRP6 transcript after LRP6 shRNA lentiviral infection after LRP6 shRNA lentiviral infection.

FIG. 21B illustrates effect of LRP6 silencing on cell apoptosis evaluated by TUNEL staining Right panel: quantification of TUNEL-positive cells from three randomly chosen fields. Note that LRP6 knockdown does not affect apoptosis.

In FIG. 21A-B, data are mean±SD from 3 independent experiments. *p<0.05; **p<0.01. FIG. 21C presents representative images showing that LRP6 knockdown leads to a decrease in colony formation in soft agar assay.

Free β-catenin pool and TCF-dependent Topflash reporter activity, measures of Wnt/β-catenin signaling strength, were significantly reduced when LRP6 was knocked down in MDA-MB-231 and HCC 1187 cells (FIG. 14B and FIG. 20C). FIG. 20C illustrates that knockdown of LRP6 decreases Wnt signaling, as shown by a GST-E-cadherin binding assay. Expression of two Wnt target genes, cyclin D1 and c-Myc, critical for cell cycle regulation, was significantly decreased in LRP6-KD cells (FIG. 14C). These results demonstrate that decreased LRP6 expression is sufficient to down-regulate Wnt signaling in breast cancer cells.

The tumorigenic properties of breast cancer cells in LRP6-KD breast cancer was examined. Cell growth slowed when LRP6 expression was knocked down in MDA-MB-231 cells (FIG. 14D). MDA-MB-231 and HCC1187 cells expressing LRP6 shRNA exhibited significantly decreased proliferation (FIG. 14E and FIG. 20D), whereas apoptosis was not affected (FIG. 21B). FIG. 20D illustrates that proliferation of LRP6 knockdown cells was decreased by 50%, as measured by a BrdU assay.

Treatment of HCC1187 cells with Wnt3a conditioned medium (CM) significantly increased cell growth when compared to treatment with L cell CM and this effect was abolished by LRP5/6 inhibitors, Dkk1 (Dickkopf1) or Mesd. FIG. 20E shows results from HCC1187 cells treated with L cell CM, Wnt3a CM, or Wnt3a CM together with Dkk1 (10 nM) or Mesd (1 μM) for 24 h; viable cells were measured by the MTT assay. In FIG. 20, * indicates p<0.05 compared to L cell CM; ** indicates p<0.01 compared to L cell CM. Furthermore, LRP6-KD cells displayed markedly lower frequencies of colony formation and smaller colony size (FIG. 14F and FIG. 21C), indicating that LRP6 down-regulation has a strong inhibitory effect on anchorage-independent growth of MDA-MB-231 cells.

Example 16

This example illustrates that overexpression of shRNA-resistant LRP6 or constitutively-active β-catenin rescues Wnt signaling and breast cancer cell growth.

To confirm that the observed effects on breast cancer cell growth are attributable specifically to LRP6 knockdown, a shRNA-resistant LRP6 (LRP6-Res) construct was generated. In these experiments, MDA-MB-231 cells expressing control or LRP6 shRNA were transfected with vector control or shRNA-resistant LRP6. The levels of LRP6 expression were examined by Western blot analysis (FIG. 15A). The data indicate that transfection of LRP6-Res construct into LRP6-KD cells markedly increased LRP6 expression in MDA-MB-231 cells (FIG. 15A).

We demonstrate that overexpression of LRP6-Res can also restore Wnt/β-catenin activation. In these experiments, cells were treated with L or Wnt3a CM. As shown in FIG. 15B and FIG. 22 A-B, overexpression of LRP6-Res restored Wnt/β-catenin activation.

Overexpression of LRP6-Res also restored cell growth (FIG. 15C). In results illustrated in FIG. 15B, expression of LRP6-Res in MDA-MB-231 cells restored Wnt signaling, including Wnt/β-catenin activation, as detected by a Topflash reporter assay. In experiments investigating effects of expression of LRP6-Res in MDA-MB-231 cells, we measured cell growth using an MTT assay. Our data demonstrate that overexpression of LRP6-Res can also restore cell growth (FIG. 15C).

FIG. 22 illustrates that shRNA-resistant LRP6 and CA β-catenin can rescue Wnt signaling. FIG. 22A: MDA-MB-231 cells expressing control or LRP6 shRNA were further transfected with GFP along with vector control or shRNA-resistant LRP6 (LRP6-Res). The transfection efficiencies were similar under different conditions (85-90%). FIG. 22B: Cells were then treated with L or Wnt3a CM. Expression of LRP6-Res in MDA-MB-231 cells restored Wnt signaling, detected by GST-E-cadherin pull-down. FIG. 22C: MDA-MB-231 cells expressing control or LRP6 shRNA were transduced with retrovirus expressing IRES-GFP vector control or CA β-catenin. The levels of LRP6, β-catenin, and CA β-catenin were determined by Western blot analysis.

To determine if the phenotypes resulting from LRP6 knockdown depend on β-catenin, MDA-MB-231 control and LRP6-KD cells were transfected with a constitutively active form of β-catenin (CA β-catenin) or its corresponding vector-control retrovirus (FIG. 22C). We found that CA β-catenin expression can significantly increase Wnt signaling and can rescue MDA-MB-231 cell growth (FIG. 15 D-F). In these experiments, MDA-MB-231 cells expressing control or LRP6 shRNA were transduced with retrovirus expressing IRES-GFP vector control or CA β-catenin. Free β-catenin levels were analyzed by GST-E-cadherin pull-down (FIG. 15D). As shown in FIG. 15E, these data indicate that CA β-catenin can promote Wnt activation independent of Wnt3a ligand. In addition, we also observed that CA β-catenin expression can restore breast cancer cell growth, as determined by an MTT assay (FIG. 15F). All results are the mean±SD of 3 independent experiments. *p<0.05; **p<0.01.

Example 17

This example illustrates that down-regulation of LRP6 in breast cancer cells suppresses tumor growth.

Figure 16:
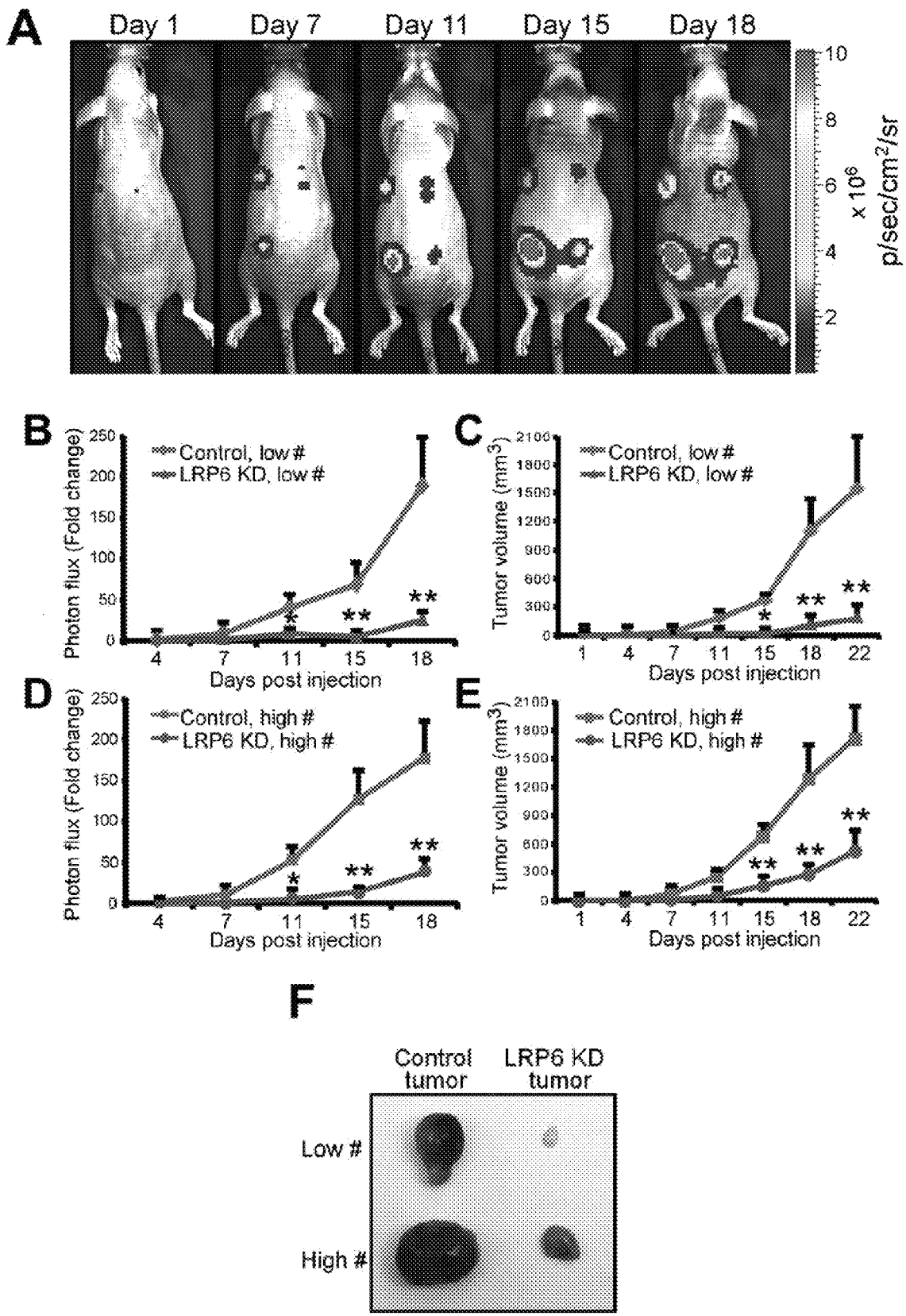
FIG. 16 illustrates that down-regulation of LRP6 significantly inhibits breast tumor growth in vivo.

To investigate if down-regulation of LRP6 affects breast cancer tumorigenesis in vivo, a tumor xenograft model was established by generating stable pools of either control or LRP6-KD MDA-MB-231 cells expressing the firefly luciferase reporter (MDA-MB-231-Luc). In these experiments, MDA-MB-231 cells (pooled clones) stably expressing LRP6 shRNA or MDA-MB-231-Luc (control) were injected s.c. into female BNX immunodeficient/immunocompromised mice. Each mouse received LRP6-KD cells in one flank of the back, and control cells in the other, providing intra-animal comparisons. Results are illustrated in FIG. 16. Tumors initiated from $5 \times 10^5$ or $2 \times 10^6$ cancer cells are indicated as Low # or High #, respectively. Low #, thoracic pair; High #, caudal pair; control tumors, left; LRP6-KD tumors, right. Tumor growth was monitored over time for 3 weeks by in vivo bioluminescent imaging and caliper measurements. Mice bearing xenograft tumors were subjected to in vivo imaging twice weekly. FIG. 16A presents representative bioluminescence images over time from the same mouse bearing MDA-MB-231 xenografts.

Tumors derived from MDA-MB-231-Luc cells stably expressing LRP6 shRNA grew substantially more slowly than those derived from control cells, as evaluated by both live-animal imaging and standard external calipers (FIG. 16B-16E). In FIG. 16B and FIG. 16D, the growth of tumors over time for control and LRP6-KD xenografts is shown as fold changes of bioluminescence photon flux values over initial value (1 day post injection). Data are mean±SEM (6 animals; four tumors each) from 2 independent experiments.

FIG. 16C and FIG. 16E: tumor volume was monitored for 3 weeks by caliper measurement. (L×W×D). *p<0.05; **p<0.01.

In xenograft experiments, gross examination of control and LRP6-KD tumors at necropsy (FIG. 16F) demonstrated that LRP6-KD tumors were significantly smaller than control tumors (490±195 mm$^3$ versus 1785±418 mm$^3$, respectively).

LRP6-KD tumors also showed decreased levels of Wnt signaling and target gene expression as a direct result of LRP6 knockdown (FIG. 16G-I). FIG. 16G presents levels of LRP6 and c-Myc in control and LRP6-KD xenograft tumors detected by Western blot analysis. FIG. 16H presents an immunohistochemical analysis of LRP6 level in control and LRP6-KD xenograft tumors with anti-LRP6 antibody (Abgent). Scale bars=50 μm. FIG. 16I illustrates a Western blot analysis showing that total and free β-catenin in LRP6-KD tumors were decreased.

Taken together, these results demonstrate that LRP6 plays a crucial role in breast cancer tumorigenesis of MDA-MB-231 cells and that down-regulation of LRP6 is sufficient to inhibit tumor growth in vivo.

Example 18

This example illustrates that the LRP6 antagonist Mesd suppresses tumor growth in vivo.

Figure 17:
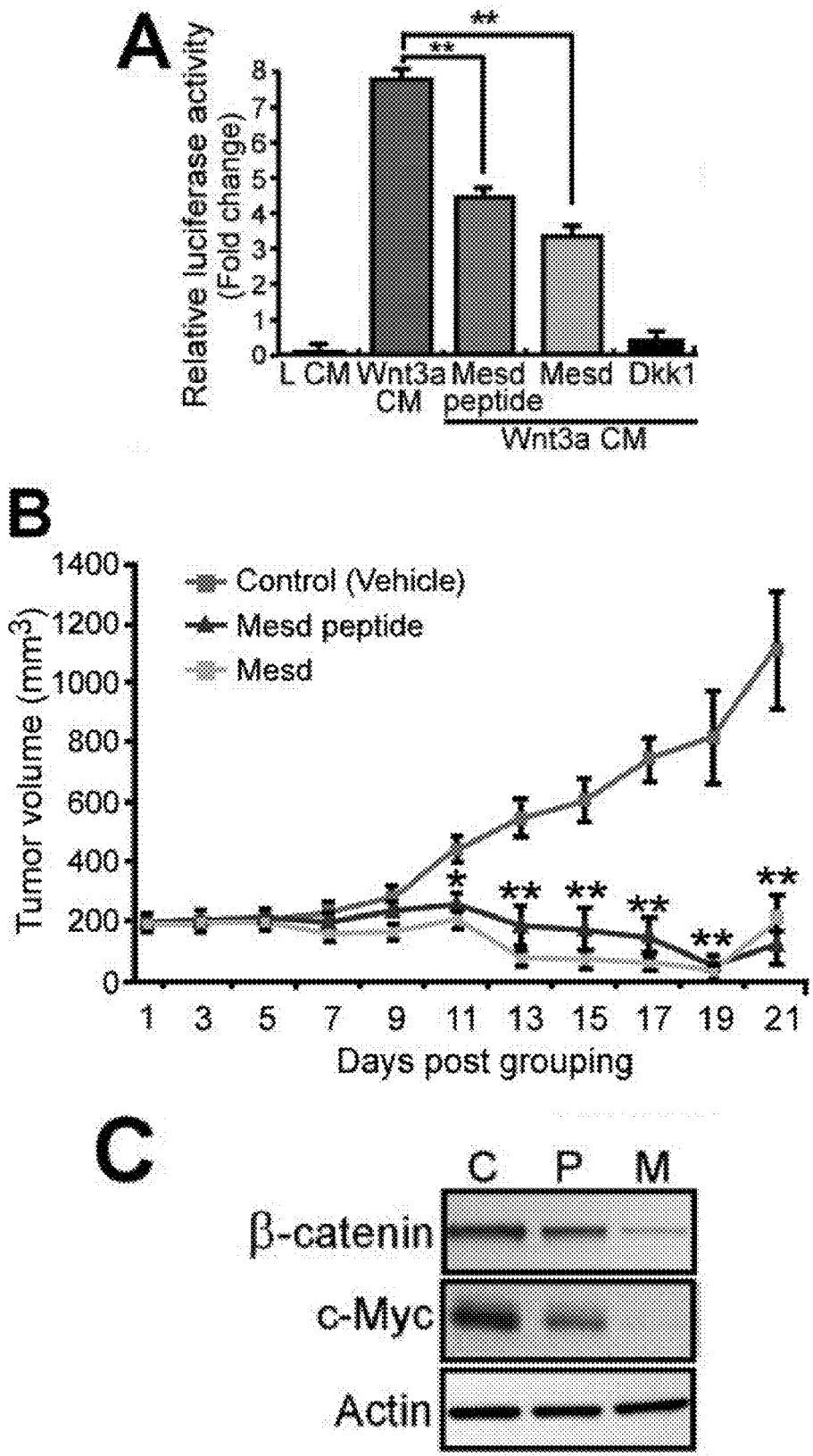
FIG. 17 illustrates therapeutic effects of Mesd treatment on MMTV-Wnt1 tumor xenografts.
Figure 17:
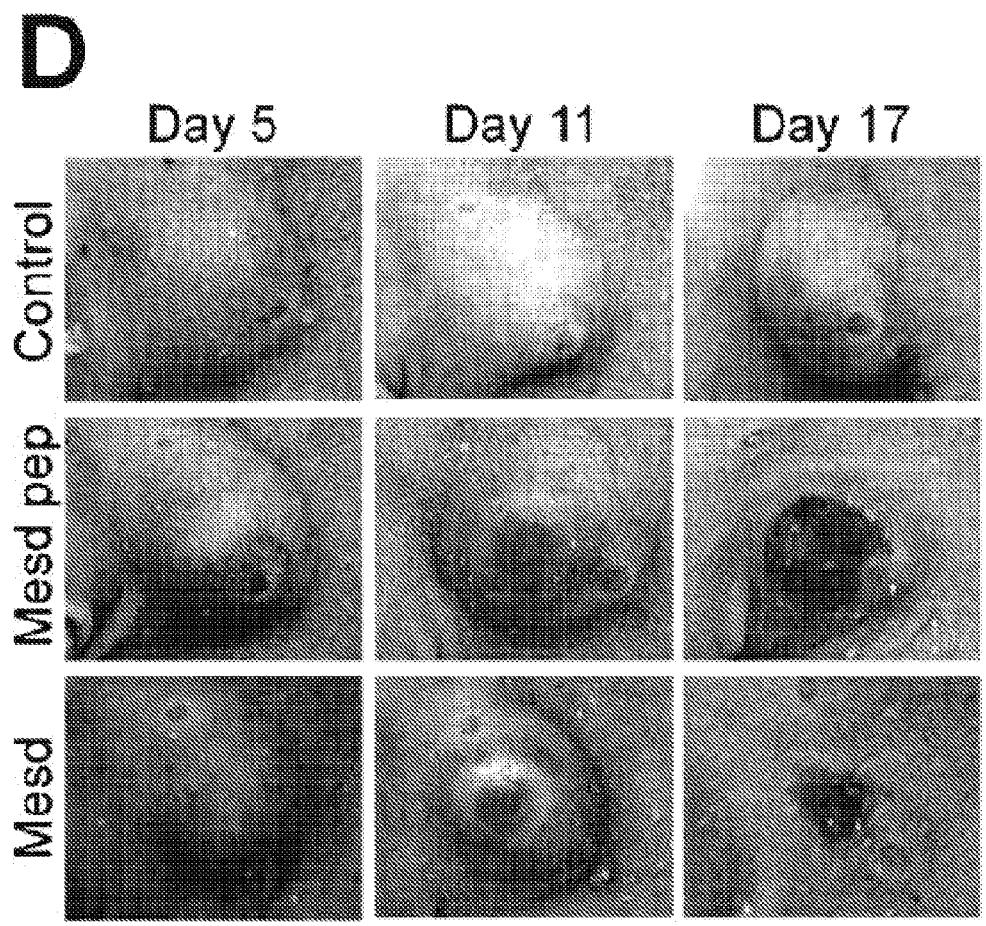
Figure 17:
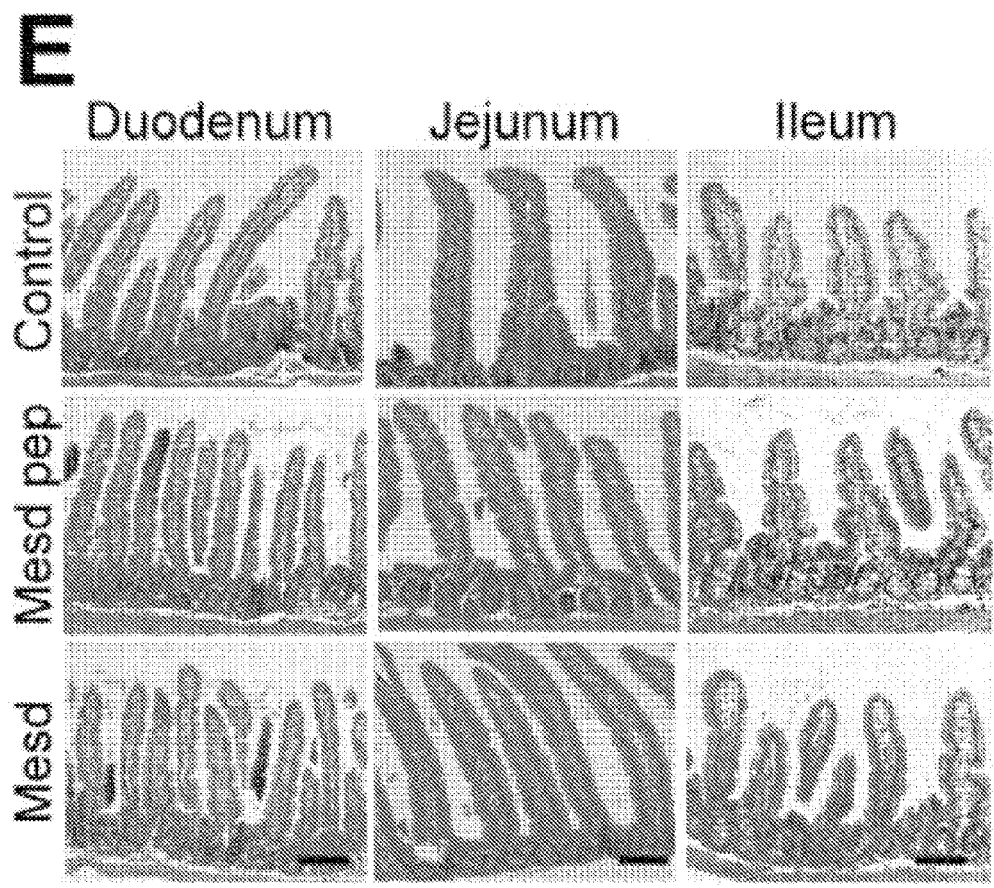

The pharmacokinetics and bioavailability of Mesd and Mesd peptide (KGGGSKEKNKTKQDKGKKKKEGDLK-SRSSKEENRAGNK (SEQ ID NO: 14)) were first investigated (FIG. 23). Cells from MMTV-Wnt1 tumors were injected into the mammary fat pads of female nude mice, and the resultant mice were subsequently randomly grouped when the mean tumor volume reached ca. 200 mm$^3$. Mice were then treated with recombinant Mesd (10 mg/kg), Mesd peptide (10 mg/kg), or vehicle control (PBS) for three weeks. As shown in FIG. 17A, Wnt inhibitory effect was analyzed by measuring luciferase activity in Wnt3a-stimulated HEK293 cells stably expressing Topflash reporter treated with indicated reagents. Cells were incubated with L CM, Wnt3a CM, or Wnt3a CM together with Mesd protein (1 μM), Mesd peptides (1 μM) or Dkk1 (10 nM) for 16 h at 37° C.

In experiments shown in FIG. 23, pharmacokinetics of Mesd peptide and Mesd were examined. FIG. 23A: Amount of Mesd in serum following a single dose of protein administration. Mice were dosed at 5, 10, 20 mg/kg of Mesd via i.p. and the serum samples were collected from individual mice at the indicated time points. The levels of Mesd in serum were quantified by comparison to Mesd pure protein with known concentrations in Western blot analysis. Values are the average of triple determinations with S.D. indicated by error bars. After dosing, the protein was rapidly absorbed, with the highest concentration at ~2 hours (Tmax). FIG. 23B: To achieve a better sensitivity for detecting the pharmacokinetics of Mesd, each mouse was injected with $^{125}$I-labeled Mesd or Mesd peptide via intravenous (tail vein) or subcutaneous routes. Samples were obtained by terminal bleed under anesthesia at each of the indicated time points (N=3 animals per time point). Radioactivity was measured using a gamma counter and DPM converted to mass units/mL blood using the specific activity (DPM/mass) of each test substance. Data are plotted as mass U/mL of test substance with standard deviation indicated by error bars. The distribution of Mesd and peptide into tissues (i.e. thyroid/parathyroid, liver, kidney, stomach, gastrointestinal tract, etc) was rapid and widespread with bioavailability averaging 60%.

We demonstrate that administration of Mesd or Mesd peptide can not only inhibit Wnt signaling and can also result in significant suppression of tumor growth (FIG. 17B-D), demonstrating that Mesd shows anti-tumorigneic effects on breast cancer.

FIG. 17B: Mesd and its peptide can significantly inhibit tumor growth. Representative pictures of tumors upon treatment are shown in FIG. 17D. In these experiments, mice bearing established MMTV-Wnt1 tumor transplants were divided into three groups (five animals per group) and were i.p. injected with PBS (vehicle), Mesd, or Mesd peptide every other day. Tumor volume was analyzed using caliper measurement. Data represent at least three independent experiments and each time point represents the mean tumor volume±SEM. *p<0.05; **p<0.01. FIG. 17C: Mesd peptide (P) and Mesd (M) treatment decreased Wnt signaling compared to control (C) treatment as confirmed by GST-E-cadherin pull-down and c-Myc target gene expression in MMTV-Wnt1 tumors. FIG. 17E illustrates that no significant adverse effect on small intestine with Mesd and Mesd peptide administration is apparent upon gross examination. Scale bar=50 μm.

Figure 24:
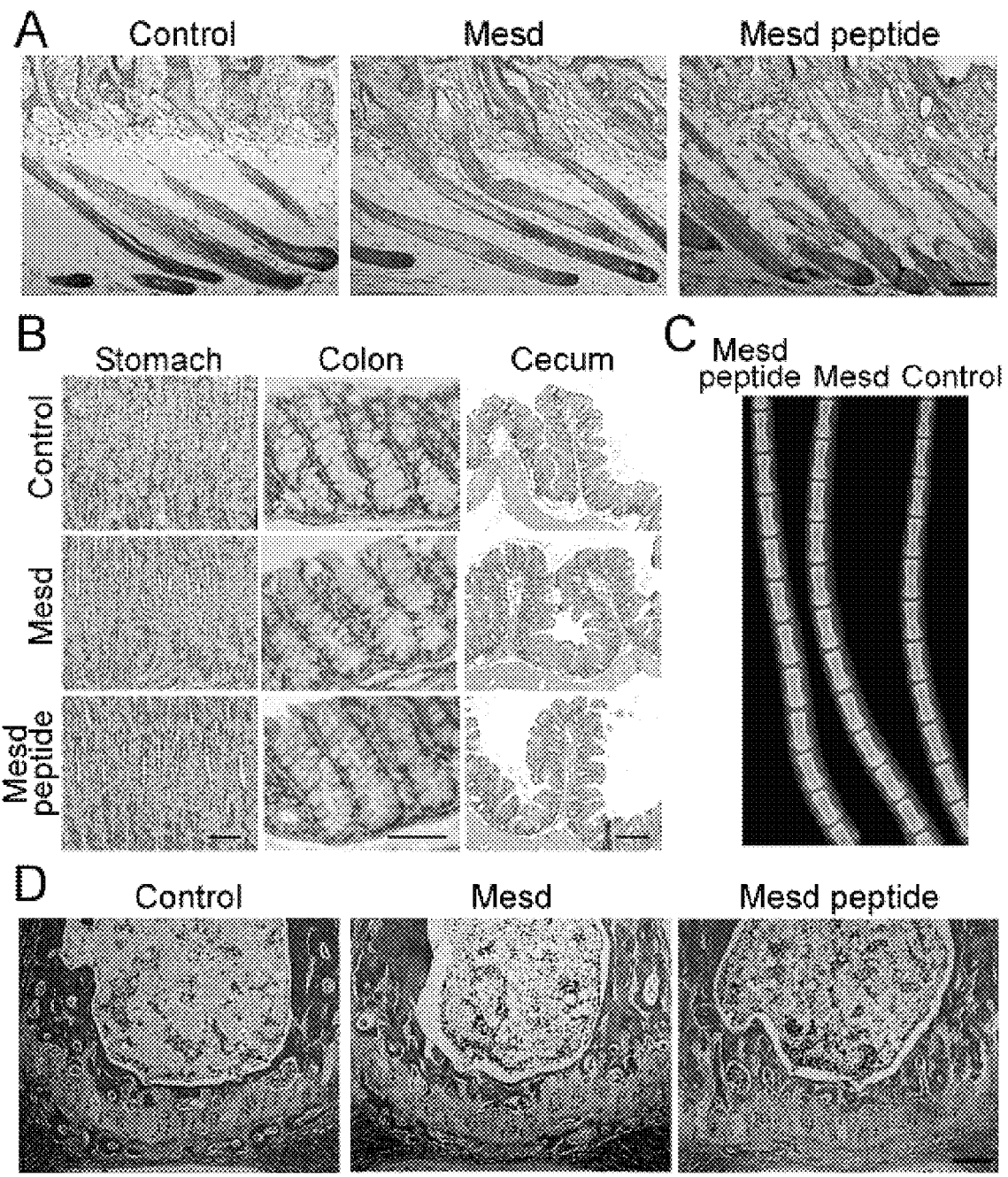
FIG. 24 illustrates effect of Mesd and Mesd peptide administration on skin hair follicle and bone.

To determine whether there are significant side effects from Mesd and Mesd peptide treatment, the architectural integrity of murine regenerating tissues, including intestinal system and skin, was examined. Mice treated with Mesd or Mesd peptide were grossly healthy and maintain their weights. Gross examination of tissues by H&E staining revealed that the architecture of various gastrointestinal compartments and skin were morphologically normal after 10 treatments with Mesd or Mesd peptide (FIG. 17E and FIG. 24 A-B). Moreover, there were no significant bone lesions or outgrowths observed in tail vertebrae of mice under the conditions in which antitumor efficacy was achieved (FIG. 24 C-D), a concern prompted because loss of LRP5 and LRP6 function diminishes bone density. Overall, these results demonstrate that systemic administration of Mesd and Mesd peptide allows for inhibition of breast tumor growth without generating apparent adverse effects on non-tumor tissues.

FIG. 24 shows Effect of Mesd and Mesd peptide administration on skin hair follicle and bone. FIG. 24A: In mice treated with Mesd and Mesd peptide, skin hair follicles and sebaceous glands exhibit no apparent gross defects when examined by H&E staining FIG. 24B: No significant adverse effect on stomach and large intestine with Mesd and Mesd peptide administration is apparent upon gross examination. Scale bars=50 μm. FIG. 24C: A representative x-ray image of tail vertebrae. No osteolytic bone lesion or outgrowth was observed upon Mesd and Mesd peptide administration. FIG. 24D: H&E staining of tail vertebrae treated with PBS, Mesd or Mesd peptide.

All publications, patents, patent applications and other references cited in this application are herein incorporated by reference in their entirety.

What is claimed is:

1. A method of treating cancer in a subject in need of treatment, the method comprising administering to the subject a therapeutically effective amount of an oligopeptide consisting of between 10 contiguous amino acids and about 70 contiguous amino acids, wherein the oligopeptide comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, a sequence sharing at least 70% sequence identity with SEQ ID NO: 1, a sequence sharing at least 70% sequence identity with SEQ ID NO: 2, a sequence sharing at least 70% sequence identity with SEQ ID NO: 3, a sequence sharing at least 70% sequence identity with SEQ ID NO: 4, a sequence sharing at least 70% sequence identity with SEQ ID NO: 5, a sequence sharing at least 70% sequence identity with SEQ ID NO: 6, a sequence sharing at least 70% sequence identity with SEQ ID NO: 7, a sequence sharing at least 70% sequence identity with SEQ ID NO: 8, a sequence sharing at least 70% sequence identity with SEQ ID NO: 9, a sequence sharing at least 70% sequence identity with SEQ ID NO: 10, a sequence sharing at least 70% sequence identity with SEQ ID NO: 11, a sequence sharing at least 70% sequence identity with SEQ ID NO: 12, a sequence sharing at least 70% sequence identity with SEQ ID NO: 13, a sequence sharing at least 70% sequence identity with SEQ ID NO: 14, a sequence sharing at least 70% sequence identity with SEQ ID NO: 15, a sequence sharing at least 70% sequence identity with SEQ ID NO: 16, a sequence sharing at least 70% sequence identity with SEQ ID NO: 17, a sequence sharing at least 70% sequence identity with SEQ ID NO: 18, a sequence sharing at least 70% sequence identity with SEQ ID NO: 19, a sequence sharing at least 70% sequence identity with SEQ ID NO: 20, a sequence sharing at least 70% sequence identity with SEQ ID NO: 21, a sequence sharing at least 70% sequence identity with SEQ ID NO: 22, a sequence sharing at least 70% sequence identity with SEQ ID NO: 23, a sequence sharing at least 70% sequence identity with SEQ ID NO: 24, a sequence sharing at least 70% sequence identity with SEQ ID NO: 25, a sequence sharing at least 70% sequence identity with SEQ ID NO: 26, a sequence sharing at least 70% sequence identity with SEQ ID NO: 27, a sequence sharing at least 70% sequence identity with SEQ ID NO: 28, a sequence sharing at least 70% sequence identity with SEQ ID NO: 29, a sequence sharing at least 70% sequence identity with SEQ ID NO: 30, a sequence sharing at least 70% sequence identity with SEQ ID NO: 31, a sequence sharing at least 70% sequence identity with SEQ ID NO: 32, a sequence sharing at least 70% sequence identity with SEQ ID NO: 33, a sequence sharing at least 70% sequence identity with SEQ ID NO: 34, a sequence sharing at least 70% sequence identity with SEQ ID NO: 35, a sequence sharing at least 70% sequence identity with SEQ ID NO: 36, a sequence sharing at least 70% sequence identity with SEQ ID NO: 37 and a sequence sharing at least 70% sequence identity with SEQ ID NO: 38, wherein the oligopeptide antagonizes binding of a Wnt ligand to at least one of LRP5 and LRP6.

2. A method in accordance with claim 1, wherein the sequence sharing at least 70% sequence identity with at least one sequence set forth as SEQ ID NO: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37 or SEQ ID NO: 38 shares at least 85% sequence identity with at least one sequence set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37 or SEQ ID NO: 38.

3. A method in accordance with claim 1, wherein the oligopeptide comprises a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23.

4. A method in accordance with claim 1, wherein the oligopeptide comprises a sequence selected from the group consisting of SEQ ID NO: 15 and SEQ ID NO: 21.

5. A method in accordance with claim 1, wherein the oligopeptide comprises SEQ ID NO: 14.

6. A method in accordance with claim 1, wherein the oligopeptide has an amino acid sequence selected from the group consisting of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 and SEQ ID NO: 32.

7. A method in accordance with claim 1, wherein the cancer is selected from the group consisting of breast cancer, multiple myeloma (MM), prostate cancer and skin cancer.

* * * * *

SEQUENCE LISTING

<160> NUMBER OF SEQ ID NOS: 39

<210> SEQ ID NO 1
<211> LENGTH: 55
<212> TYPE: PRT
<213> ORGANISM: Bos taurus

<400> SEQUENCE: 1

Cys Ala Asp Val Thr Leu Glu Gly Gln Val Tyr Pro Gly Lys Gly Gly
1               5                   10                  15

Gly Ser Lys Glu Lys Asn Gln Thr Lys Gln Lys Gly Lys Lys Lys
            20                  25                  30

Lys Glu Arg Asp Leu Lys Pro Arg Ala Ser Lys Glu Asp Asn Arg Ala
        35                  40                  45

Gly Ser Lys Lys Glu Glu Leu
        50                  55

<210> SEQ ID NO 2
<211> LENGTH: 57
<212> TYPE: PRT
<213> ORGANISM: Canis familiaris

<400> SEQUENCE: 2

Cys Ala Asp Val Thr Leu Glu Gly Gln Val Tyr Pro Gly Lys Gly Gly
1               5                   10                  15

Gly Ser Gln Glu Lys Asn Lys Thr Lys Gln Lys Gly Lys Lys Lys Lys
            20                  25                  30

Lys Glu Gly Val Pro Lys Ser Arg Ala Lys Val Val Gln Glu Asp Asn
        35                  40                  45

Arg Ala Gly Asn Lys Arg Glu Glu Leu
        50                  55

<210> SEQ ID NO 3
<211> LENGTH: 55
<212> TYPE: PRT
<213> ORGANISM: Homo sapiens

<400> SEQUENCE: 3

Cys Ala Asp Val Thr Leu Glu Gly Gln Val Tyr Pro Gly Lys Gly Gly
1               5                   10                  15

Gly Ser Lys Glu Lys Asn Lys Thr Lys Gln Asp Lys Gly Lys Lys Lys
            20                  25                  30

Lys Glu Gly Asp Leu Lys Ser Arg Ser Ser Lys Glu Glu Asn Arg Ala
        35                  40                  45

Gly Asn Lys Arg Glu Asp Leu
        50                  55

<210> SEQ ID NO 4
<211> LENGTH: 54
<212> TYPE: PRT
<213> ORGANISM: Mus musculus

<400> SEQUENCE: 4

Cys Ala Glu Val Thr Leu Glu Gly Gln Met Tyr Pro Gly Lys Gly Gly
1               5                   10                  15

Gly Ser Lys Glu Lys Asn Lys Thr Lys Pro Gly Lys Ala Lys Lys Lys
            20                  25                  30

Glu Gly Asp Pro Lys Pro Arg Ala Ser Lys Glu Asp Asn Arg Ala Gly
        35                  40                  45

```
Ser Arg Arg Glu Asp Leu
    50

<210> SEQ ID NO 5
<211> LENGTH: 54
<212> TYPE: PRT
<213> ORGANISM: Mus musculus

<400> SEQUENCE: 5

Cys Ala Glu Val Thr Leu Glu Gly Gln Met Tyr Pro Gly Lys Gly Gly
1               5                   10                  15

Gly Ser Lys Glu Lys Asn Lys Thr Lys Pro Glu Lys Ala Lys Lys Lys
            20                  25                  30

Glu Gly Asp Arg Lys Pro Arg Ala Ser Lys Glu Asp Asn Arg Ala Gly
        35                  40                  45

Ser Arg Arg Glu Asp Leu
    50

<210> SEQ ID NO 6
<211> LENGTH: 55
<212> TYPE: PRT
<213> ORGANISM: Pongo pygmaeus

<400> SEQUENCE: 6

Cys Ala Asp Val Thr Leu Glu Gly Gln Val Tyr Pro Gly Lys Gly Gly
1               5                   10                  15

Gly Ser Lys Glu Lys Asn Lys Thr Gln Asp Lys Gly Lys Lys Lys
            20                  25                  30

Lys Glu Gly Asp Leu Lys Ser Arg Ser Ser Lys Glu Asp Asn Arg Ala
        35                  40                  45

Arg Asn Lys Arg Glu Asp Leu
    50                  55

<210> SEQ ID NO 7
<211> LENGTH: 54
<212> TYPE: PRT
<213> ORGANISM: Rattus norvegicus

<400> SEQUENCE: 7

Cys Ala Glu Val Thr Leu Glu Gly Gln Met Tyr Pro Gly Lys Gly Gly
1               5                   10                  15

Gly Ser Lys Glu Lys Asn Lys Thr Lys Pro Glu Lys Gly Lys Lys Lys
            20                  25                  30

Glu Gly Asp Pro Lys Pro Arg Ala Ser Lys Glu Asp Asn Arg Ala Gly
        35                  40                  45

Ser Arg Arg Glu Asp Leu
    50

<210> SEQ ID NO 8
<211> LENGTH: 55
<212> TYPE: PRT
<213> ORGANISM: Gallus gallus

<400> SEQUENCE: 8

Cys Ala Asp Val Thr Leu Glu Gly Gln Val Tyr Pro Gly Lys Gly Ala
1               5                   10                  15

Asp Gly Ser Glu Lys Gly Arg Asn Lys Thr Lys Pro Glu Lys Ala Lys
            20                  25                  30

Lys Lys Lys Asp Ala Glu Lys Ser Lys Ser Ser His Glu Asp Asn Arg
        35                  40                  45
```

```
Ala Asn Gln Thr Glu Arg Gly
    50              55

<210> SEQ ID NO 9
<211> LENGTH: 10
<212> TYPE: PRT
<213> ORGANISM: Artificial
<220> FEATURE:
<223> OTHER INFORMATION: Synthetic

<400> SEQUENCE: 9

Lys Gly Gly Gly Ser Lys Glu Lys Asn Lys
1               5                   10

<210> SEQ ID NO 10
<211> LENGTH: 10
<212> TYPE: PRT
<213> ORGANISM: Artificial
<220> FEATURE:
<223> OTHER INFORMATION: Synthetic

<400> SEQUENCE: 10

Lys Gly Gly Gly Ser Gln Glu Lys Asn Lys
1               5                   10

<210> SEQ ID NO 11
<211> LENGTH: 10
<212> TYPE: PRT
<213> ORGANISM: Artificial
<220> FEATURE:
<223> OTHER INFORMATION: Synthetic

<400> SEQUENCE: 11

Lys Gly Gly Gly Ser Lys Glu Lys Asn Gln
1               5                   10

<210> SEQ ID NO 12
<211> LENGTH: 10
<212> TYPE: PRT
<213> ORGANISM: Artificial
<220> FEATURE:
<223> OTHER INFORMATION: Synthetic

<400> SEQUENCE: 12

Lys Gly Gly Gly Ser Lys Glu Arg Gln Leu
1               5                   10

<210> SEQ ID NO 13
<211> LENGTH: 34
<212> TYPE: PRT
<213> ORGANISM: Artificial
<220> FEATURE:
<223> OTHER INFORMATION: Synthetic

<400> SEQUENCE: 13

Lys Gly Gly Gly Ser Lys Glu Asn Lys Thr Lys Gln Asp Lys Gly
1               5                   10                  15

Lys Lys Lys Lys Glu Gly Asp Leu Lys Ser Arg Ser Lys Glu Glu
            20                  25                  30

Asn Arg

<210> SEQ ID NO 14
<211> LENGTH: 38
<212> TYPE: PRT
<213> ORGANISM: Artificial
<220> FEATURE:
```

<223> OTHER INFORMATION: Synthetic

<400> SEQUENCE: 14

Lys Gly Gly Gly Ser Lys Glu Lys Asn Lys Thr Lys Gln Asp Lys Gly
1               5                   10                  15

Lys Lys Lys Lys Glu Gly Asp Leu Lys Ser Arg Ser Lys Glu Glu
            20                  25                  30

Asn Arg Ala Gly Asn Lys
        35

<210> SEQ ID NO 15
<211> LENGTH: 47
<212> TYPE: PRT
<213> ORGANISM: Artificial
<220> FEATURE:
<223> OTHER INFORMATION: Synthetic

<400> SEQUENCE: 15

Gln Val Tyr Pro Gly Lys Gly Gly Ser Lys Glu Lys Asn Lys Thr
1               5                   10                  15

Lys Gln Asp Lys Gly Lys Lys Lys Glu Gly Asp Leu Lys Ser Arg
            20                  25                  30

Ser Ser Lys Glu Glu Asn Arg Ala Gly Asn Lys Arg Glu Asp Leu
        35                  40                  45

<210> SEQ ID NO 16
<211> LENGTH: 33
<212> TYPE: PRT
<213> ORGANISM: Artificial
<220> FEATURE:
<223> OTHER INFORMATION: Synthetic

<400> SEQUENCE: 16

Lys Gly Gly Gly Ser Lys Glu Lys Asn Lys Thr Lys Pro Glu Lys Ala
1               5                   10                  15

Lys Lys Lys Glu Gly Asp Pro Lys Pro Arg Ala Ser Lys Glu Asp Asn
            20                  25                  30

Arg

<210> SEQ ID NO 17
<211> LENGTH: 33
<212> TYPE: PRT
<213> ORGANISM: Artificial
<220> FEATURE:
<223> OTHER INFORMATION: Synthetic

<400> SEQUENCE: 17

Lys Gly Gly Gly Ser Lys Glu Lys Asn Lys Thr Lys Pro Glu Lys Ala
1               5                   10                  15

Lys Lys Lys Glu Gly Asp Arg Lys Pro Arg Ala Ser Lys Glu Asp Asn
            20                  25                  30

Arg

<210> SEQ ID NO 18
<211> LENGTH: 37
<212> TYPE: PRT
<213> ORGANISM: Artificial
<220> FEATURE:
<223> OTHER INFORMATION: Synthetic

<400> SEQUENCE: 18

Ser Lys Glu Lys Asn Lys Thr Lys Pro Glu Lys Ala Lys Lys Lys Glu
1               5                   10                  15

```
Gly Asp Pro Lys Pro Arg Ala Ser Lys Glu Asp Asn Arg Ala Gly Ser
            20                  25                  30

Arg Arg Glu Asp Leu
        35

<210> SEQ ID NO 19
<211> LENGTH: 37
<212> TYPE: PRT
<213> ORGANISM: Artificial
<220> FEATURE:
<223> OTHER INFORMATION: Synthetic

<400> SEQUENCE: 19

Ser Lys Glu Lys Asn Lys Thr Lys Pro Glu Lys Ala Lys Lys Lys Glu
1               5                   10                  15

Gly Asp Arg Lys Pro Arg Ala Ser Lys Glu Asp Asn Arg Ala Gly Ser
            20                  25                  30

Arg Arg Glu Asp Leu
        35

<210> SEQ ID NO 20
<211> LENGTH: 37
<212> TYPE: PRT
<213> ORGANISM: Artificial
<220> FEATURE:
<223> OTHER INFORMATION: Synthetic

<400> SEQUENCE: 20

Lys Gly Gly Gly Ser Lys Glu Lys Asn Lys Thr Lys Pro Glu Lys Ala
1               5                   10                  15

Lys Lys Lys Glu Gly Asp Pro Lys Pro Arg Ala Ser Lys Glu Asp Asn
            20                  25                  30

Arg Ala Gly Ser Arg
        35

<210> SEQ ID NO 21
<211> LENGTH: 37
<212> TYPE: PRT
<213> ORGANISM: Artificial
<220> FEATURE:
<223> OTHER INFORMATION: Synthetic

<400> SEQUENCE: 21

Lys Gly Gly Gly Ser Lys Glu Lys Asn Lys Thr Lys Pro Glu Lys Ala
1               5                   10                  15

Lys Lys Lys Glu Gly Asp Arg Lys Pro Arg Ala Ser Lys Glu Asp Asn
            20                  25                  30

Arg Ala Gly Ser Arg
        35

<210> SEQ ID NO 22
<211> LENGTH: 46
<212> TYPE: PRT
<213> ORGANISM: Artificial
<220> FEATURE:
<223> OTHER INFORMATION: Synthetic

<400> SEQUENCE: 22

Gln Met Tyr Pro Gly Lys Gly Gly Ser Lys Glu Lys Asn Lys Thr
1               5                   10                  15

Lys Pro Glu Lys Ala Lys Lys Lys Glu Gly Asp Pro Lys Pro Arg Ala
            20                  25                  30
```

Ser Lys Glu Asp Asn Arg Ala Gly Ser Arg Arg Glu Asp Leu
        35                  40                  45

<210> SEQ ID NO 23
<211> LENGTH: 18
<212> TYPE: PRT
<213> ORGANISM: Artificial
<220> FEATURE:
<223> OTHER INFORMATION: Synthetic

<400> SEQUENCE: 23

Glu Gly Asp Pro Lys Pro Arg Ala Ser Lys Glu Asp Asn Arg Ala Gly
1               5                   10                  15

Ser Arg

<210> SEQ ID NO 24
<211> LENGTH: 18
<212> TYPE: PRT
<213> ORGANISM: Artificial
<220> FEATURE:
<223> OTHER INFORMATION: Synthetic

<400> SEQUENCE: 24

Glu Gly Asp Arg Lys Pro Arg Ala Ser Lys Glu Asp Asn Arg Ala Gly
1               5                   10                  15

Ser Arg

<210> SEQ ID NO 25
<211> LENGTH: 18
<212> TYPE: PRT
<213> ORGANISM: Artificial
<220> FEATURE:
<223> OTHER INFORMATION: Synthetic

<400> SEQUENCE: 25

Thr Lys Pro Glu Lys Ala Lys Lys Lys Glu Gly Asp Pro Lys Pro Arg
1               5                   10                  15

Ala Ser

<210> SEQ ID NO 26
<211> LENGTH: 19
<212> TYPE: PRT
<213> ORGANISM: Artificial
<220> FEATURE:
<223> OTHER INFORMATION: Synthetic

<400> SEQUENCE: 26

Lys Gly Gly Gly Ser Lys Glu Lys Asn Lys Thr Lys Pro Glu Lys Ala
1               5                   10                  15

Lys Lys Lys

<210> SEQ ID NO 27
<211> LENGTH: 18
<212> TYPE: PRT
<213> ORGANISM: Artificial
<220> FEATURE:
<223> OTHER INFORMATION: Synthetic

<400> SEQUENCE: 27

Thr Lys Pro Glu Lys Ala Lys Lys Lys Glu Gly Asp Arg Lys Pro Arg
1               5                   10                  15

Ala Ser

<210> SEQ ID NO 28

```
<211> LENGTH: 9
<212> TYPE: PRT
<213> ORGANISM: Artificial
<220> FEATURE:
<223> OTHER INFORMATION: Synthetic

<400> SEQUENCE: 28

Lys Glu Asp Asn Arg Ala Gly Ser Arg
1               5

<210> SEQ ID NO 29
<211> LENGTH: 10
<212> TYPE: PRT
<213> ORGANISM: Artificial
<220> FEATURE:
<223> OTHER INFORMATION: Synthetic

<400> SEQUENCE: 29

Lys Glu Lys Asn Lys Thr Lys Pro Glu Lys
1               5                   10

<210> SEQ ID NO 30
<211> LENGTH: 232
<212> TYPE: PRT
<213> ORGANISM: Bos taurus

<400> SEQUENCE: 30

Met Ala Ala Ser Gly Trp Ala Arg Ala Ala Val Ile Phe Leu Cys Ala
1               5                   10                  15

Cys Asp Leu Leu Leu Leu Leu Leu Pro Pro Arg Ala Phe Ala Thr
            20                  25                  30

Glu Gly Pro Ala Glu Thr Pro Gly Glu Ala Thr Pro Pro Arg Lys
        35                  40                  45

Lys Lys Lys Asp Ile Arg Asp Tyr Asn Asp Ala Asp Met Ala Arg Leu
    50                  55                  60

Leu Glu Gln Trp Glu Lys Asp Asp Ile Glu Glu Gly Asp Leu Pro
65                  70                  75                  80

Glu His Lys Arg Pro Ser Ala Pro Ile Asp Phe Ser Gln Ile Asp Pro
                85                  90                  95

Gly Lys Pro Glu Ser Ile Leu Lys Met Thr Lys Lys Gly Lys Thr Leu
            100                 105                 110

Met Met Phe Val Thr Val Ser Gly Asn Pro Thr Glu Lys Glu Thr Glu
                115                 120                 125

Glu Ile Thr Ser Leu Trp Gln Gly Ser Leu Phe Asn Ala Asn Tyr Asp
            130                 135                 140

Val Gln Arg Phe Ile Val Gly Ser Asp Arg Ala Ile Phe Met Leu Arg
145                 150                 155                 160

Asp Gly Gly Tyr Ala Trp Glu Ile Lys Asp Phe Leu Val Ser Gln Asp
                165                 170                 175

Arg Cys Ala Asp Val Thr Leu Glu Gly Gln Val Tyr Pro Gly Lys Gly
                180                 185                 190

Gly Gly Ser Lys Glu Lys Asn Gln Thr Lys Gln Glu Lys Gly Lys Lys
            195                 200                 205

Lys Lys Glu Arg Asp Leu Lys Pro Arg Ala Ser Lys Glu Asp Asn Arg
    210                 215                 220

Ala Gly Ser Lys Lys Glu Glu Leu
225                 230

<210> SEQ ID NO 31
<211> LENGTH: 190
```

```
<212> TYPE: PRT
<213> ORGANISM: Canis familiaris

<400> SEQUENCE: 31

Met Gly Ser His Val Leu Val Thr Arg Val Ile Gly Ala Glu Ser Cys
1               5                   10                  15

Trp Arg Leu Gly Leu His Leu Lys Lys Asp Asp Ile Glu Glu Gly
            20                  25                  30

Asp Leu Pro Glu His Lys Arg Pro Ser Ala Pro Ile Asp Phe Ser Gln
            35                  40                  45

Ile Asp Pro Gly Arg Pro Glu Ser Ile Leu Lys Met Thr Lys Lys Gly
50                  55                  60

Lys Thr Leu Met Met Phe Val Thr Val Ser Gly Ser Pro Thr Glu Lys
65                  70                  75                  80

Glu Thr Glu Glu Ile Thr Ser Leu Trp Gln Gly Ser Leu Phe Asn Ala
                85                  90                  95

Asn Tyr Asp Val Gln Arg Phe Ile Val Gly Ser Asp Arg Ala Ile Phe
            100                 105                 110

Met Leu Arg Asp Gly Ser Tyr Ala Trp Glu Ile Lys Asp Phe Leu Val
            115                 120                 125

Ser Gln Asp Arg Cys Ala Asp Val Thr Leu Glu Gly Gln Val Tyr Pro
130                 135                 140

Gly Lys Gly Gly Gly Ser Gln Glu Lys Asn Lys Thr Lys Gln Glu Lys
145                 150                 155                 160

Gly Lys Lys Lys Lys Glu Gly Val Pro Lys Ser Arg Ala Ala Lys Val
                165                 170                 175

Val Gln Glu Asp Asn Arg Ala Gly Asn Lys Arg Glu Glu Leu
            180                 185                 190

<210> SEQ ID NO 32
<211> LENGTH: 234
<212> TYPE: PRT
<213> ORGANISM: Homo sapiens

<400> SEQUENCE: 32

Met Ala Ala Ser Arg Trp Ala Arg Lys Ala Val Val Leu Leu Cys Ala
1               5                   10                  15

Ser Asp Leu Leu Leu Leu Leu Leu Leu Pro Pro Gly Ser Cys
            20                  25                  30

Ala Ala Glu Gly Ser Pro Gly Thr Pro Asp Glu Ser Thr Pro Pro Pro
            35                  40                  45

Arg Lys Lys Lys Lys Asp Ile Arg Asp Tyr Asn Asp Ala Asp Met Ala
50                  55                  60

Arg Leu Leu Glu Gln Trp Glu Lys Asp Asp Ile Glu Glu Gly Asp
65                  70                  75                  80

Leu Pro Glu His Lys Arg Pro Ser Ala Pro Val Asp Phe Ser Lys Ile
                85                  90                  95

Asp Pro Ser Lys Pro Glu Ser Ile Leu Lys Met Thr Lys Lys Gly Lys
            100                 105                 110

Thr Leu Met Met Phe Val Thr Val Ser Gly Ser Pro Thr Glu Lys Glu
            115                 120                 125

Thr Glu Glu Ile Thr Ser Leu Trp Gln Gly Ser Leu Phe Asn Ala Asn
            130                 135                 140

Tyr Asp Val Gln Arg Phe Ile Val Gly Ser Asp Arg Ala Ile Phe Met
145                 150                 155                 160

Leu Arg Asp Gly Ser Tyr Ala Trp Glu Ile Lys Asp Phe Leu Val Gly
```

```
                    165                 170                 175
Gln Asp Arg Cys Ala Asp Val Thr Leu Glu Gly Gln Val Tyr Pro Gly
            180                 185                 190

Lys Gly Gly Gly Ser Lys Glu Lys Asn Lys Thr Lys Gln Asp Lys Gly
            195                 200                 205

Lys Lys Lys Lys Glu Gly Asp Leu Lys Ser Arg Ser Ser Lys Glu Glu
        210                 215                 220

Asn Arg Ala Gly Asn Lys Arg Glu Asp Leu
225                 230

<210> SEQ ID NO 33
<211> LENGTH: 223
<212> TYPE: PRT
<213> ORGANISM: Gallus gallus

<400> SEQUENCE: 33

Met Ala Ala Ala Ala Arg Trp Ala Ala Leu Gly Leu Ala Leu Trp Leu
1               5                   10                  15

Cys Ala Ala Ala His Ala Glu Glu Pro Glu Gly Lys Arg Arg Ala Gly
            20                  25                  30

Pro Ala Lys Lys Lys Asp Ile Arg Asp Tyr Asn Asp Ala Asp Met Ala
        35                  40                  45

Arg Leu Leu Glu Gln Trp Glu Lys Asp Asp Ile Glu Glu Gly Asp
    50                  55                  60

Leu Pro Glu His Lys Arg Pro Ala Pro Ile Asp Phe Ser Lys Ile
65                  70                  75                  80

Asp Pro Gly Lys Pro Glu Ser Ile Leu Lys Leu Thr Lys Lys Gly Lys
                85                  90                  95

Thr Leu Met Met Phe Val Thr Val Ser Gly Asn Pro Thr Glu Lys Glu
            100                 105                 110

Thr Glu Glu Ile Thr Ser Leu Trp Gln Gly Ser Leu Phe Asn Ala Asn
        115                 120                 125

Tyr Asp Val Gln Arg Phe Ile Val Gly Ser Asn Arg Ala Ile Phe Met
    130                 135                 140

Leu Arg Asp Gly Gly Tyr Ala Trp Glu Ile Lys Asp Phe Leu Ile Ser
145                 150                 155                 160

Gln Glu Arg Cys Ala Asp Val Thr Leu Glu Gly Gln Val Tyr Pro Gly
                165                 170                 175

Lys Gly Ala Asp Gly Ser Glu Lys Gly Arg Asn Lys Thr Lys Pro Glu
            180                 185                 190

Lys Ala Lys Lys Lys Asp Ala Glu Lys Ser Lys Ser Ser His Glu
        195                 200                 205

Asp Asn Arg Ala Asn Gln Thr Glu Arg Gly Ser Met Thr Asp Thr
    210                 215                 220

<210> SEQ ID NO 34
<211> LENGTH: 224
<212> TYPE: PRT
<213> ORGANISM: Mus musculus

<400> SEQUENCE: 34

Met Ala Ala Ser Arg Trp Leu Arg Ala Val Leu Leu Phe Leu Cys Ala
1               5                   10                  15

Ser Asp Leu Leu Leu Pro Pro Asn Ala Tyr Ala Ala Asp Thr
            20                  25                  30

Pro Gly Glu Ala Thr Pro Pro Arg Lys Lys Lys Asp Ile Arg Asp
        35                  40                  45
```

Tyr Asn Asp Ala Asp Met Ala Arg Leu Leu Glu Gln Trp Glu Lys Asp
 50                  55                  60
Asp Asp Ile Glu Glu Gly Asp Leu Pro Glu His Lys Arg Pro Ser Ala
65                  70                  75                  80
Pro Ile Asp Phe Ser Lys Leu Asp Pro Gly Lys Pro Glu Ser Ile Leu
                85                  90                  95
Lys Met Thr Lys Lys Gly Lys Thr Leu Met Met Phe Val Thr Val Ser
            100                 105                 110
Gly Asn Pro Thr Glu Lys Glu Thr Glu Ile Thr Ser Leu Trp Gln
        115                 120                 125
Gly Ser Leu Phe Asn Ala Asn Tyr Asp Val Gln Arg Phe Ile Val Gly
    130                 135                 140
Ser Asp Arg Ala Ile Phe Met Leu Arg Asp Gly Ser Tyr Ala Trp Glu
145                 150                 155                 160
Ile Lys Asp Phe Leu Val Ser Gln Asp Arg Cys Ala Glu Val Thr Leu
                165                 170                 175
Glu Gly Gln Met Tyr Pro Gly Lys Gly Gly Ser Lys Glu Lys Asn
            180                 185                 190
Lys Thr Lys Pro Glu Lys Ala Lys Lys Glu Gly Asp Arg Lys Pro
        195                 200                 205
Arg Ala Ser Lys Glu Asp Asn Arg Ala Gly Ser Arg Arg Glu Asp Leu
    210                 215                 220

<210> SEQ ID NO 35
<211> LENGTH: 235
<212> TYPE: PRT
<213> ORGANISM: Pan troglodytes

<400> SEQUENCE: 35

Lys Met Ala Ala Ser Arg Trp Ala Arg Lys Ala Val Val Leu Leu Cys
1               5                   10                  15
Ala Ser Asp Leu Leu Leu Leu Leu Leu Pro Pro Gly Ser
            20                  25                  30
Cys Ala Ala Glu Gly Ser Pro Gly Thr Pro Asp Glu Ser Thr Pro Pro
            35                  40                  45
Pro Arg Lys Lys Lys Lys Asp Ile Arg Asp Tyr Asn Asp Ala Asp Met
 50                  55                  60
Ala Arg Leu Leu Glu Gln Trp Glu Lys Asp Asp Ile Glu Glu Gly
65                  70                  75                  80
Asp Leu Pro Glu His Lys Arg Pro Ser Ala Pro Val Asp Phe Ser Lys
                85                  90                  95
Ile Asp Pro Ser Lys Pro Glu Ser Ile Leu Lys Met Thr Lys Lys Gly
            100                 105                 110
Lys Thr Leu Met Met Phe Val Thr Val Ser Gly Ser Pro Thr Glu Lys
        115                 120                 125
Glu Thr Glu Ile Thr Ser Leu Trp Gln Gly Ser Leu Phe Asn Ala
    130                 135                 140
Asn Tyr Asp Val Gln Arg Phe Ile Val Gly Ser Asp Arg Ala Ile Phe
145                 150                 155                 160
Met Leu Arg Asp Gly Ser Tyr Ala Trp Glu Ile Lys Asp Phe Leu Val
                165                 170                 175
Gly Gln Asp Arg Cys Ala Asp Val Thr Leu Glu Gly Gln Val Tyr Pro
            180                 185                 190
Gly Lys Gly Gly Ser Lys Glu Lys Asn Lys Thr Lys Gln Asp Lys
        195                 200                 205

Gly Lys Lys Lys Lys Glu Gly Asp Leu Lys Ser Arg Ser Ser Lys Glu
    210                 215                 220

Glu Asn Arg Ala Gly Asn Lys Arg Glu Asp Leu
225                 230                 235

<210> SEQ ID NO 36
<211> LENGTH: 234
<212> TYPE: PRT
<213> ORGANISM: Pongo pygmaeus

<400> SEQUENCE: 36

Met Ala Ala Ser Ser Trp Ala Arg Lys Ala Val Val Leu Cys Ala
1               5                   10                  15

Ser Asp Leu Leu Leu Leu Leu Leu Leu Pro Pro Gly Ser Cys
        20                  25                  30

Ala Ala Glu Ala Ser Pro Gly Thr Pro Asp Glu Ser Thr Pro Pro
        35                  40                  45

Arg Lys Lys Lys Lys Asp Ile Arg Asp Tyr Asn Asp Ala Asp Met Ala
    50                  55                  60

Arg Leu Leu Glu Gln Trp Glu Lys Asp Asp Ile Glu Glu Gly Asp
65              70                  75                  80

Leu Pro Glu His Lys Arg Pro Ser Ala Pro Val Asp Phe Ser Lys Ile
                85                  90                  95

Asp Pro Ser Lys Pro Glu Ser Ile Leu Lys Met Thr Lys Lys Gly Lys
                100                 105                 110

Thr Leu Met Met Phe Val Thr Val Ser Gly Ser Pro Thr Glu Lys Glu
                115                 120                 125

Thr Glu Glu Ile Thr Ser Leu Trp Gln Gly Ser Leu Phe Asn Ala Asn
130                 135                 140

Tyr Asp Val Gln Arg Phe Ile Val Gly Ser Arg Ala Ile Phe Met
145                 150                 155                 160

Leu Arg Asp Gly Asn Tyr Ala Trp Glu Ile Lys Asp Phe Leu Val Gly
                165                 170                 175

Gln Asp Arg Cys Ala Asp Val Thr Leu Glu Gly Gln Val Tyr Pro Gly
                180                 185                 190

Lys Gly Gly Ser Lys Glu Lys Asn Lys Thr Lys Gln Asp Lys Gly
                195                 200                 205

Lys Lys Lys Lys Glu Gly Asp Leu Lys Ser Arg Ser Ser Lys Glu Asp
    210                 215                 220

Asn Arg Ala Arg Asn Lys Arg Glu Asp Leu
225                 230

<210> SEQ ID NO 37
<211> LENGTH: 224
<212> TYPE: PRT
<213> ORGANISM: Rattus norvegicus

<400> SEQUENCE: 37

Met Ala Ala Ser Ser Trp Leu Arg Ala Val Leu Leu Phe Leu Cys Ala
1               5                   10                  15

Ser Asp Leu Leu Leu Leu Ser Pro Pro Glu Ala Tyr Ala Thr Asp Thr
                20                  25                  30

Pro Gly Glu Ala Ile Thr Pro Pro Arg Lys Lys Lys Asp Ile Arg Asp
                35                  40                  45

Tyr Asn Asp Ala Asp Met Ala Arg Leu Leu Glu Gln Trp Glu Lys Asp
    50                  55                  60

```
Asp Asp Ile Glu Glu Gly Asp Leu Pro Glu His Lys Arg Pro Ser Ala
 65                  70                  75                  80

Pro Ile Asp Phe Ser Lys Leu Asp Pro Gly Lys Pro Glu Ser Ile Leu
                 85                  90                  95

Lys Met Thr Lys Lys Gly Lys Thr Leu Met Met Phe Val Thr Ile Ser
            100                 105                 110

Gly Asn Pro Thr Glu Lys Glu Thr Glu Glu Ile Thr Ser Leu Trp Gln
        115                 120                 125

Gly Ser Leu Phe Asn Ala Asn Tyr Asp Val Gln Arg Phe Ile Val Gly
    130                 135                 140

Ser Asp Arg Ala Ile Phe Met Leu Arg Asp Gly Ser Tyr Ala Trp Glu
145                 150                 155                 160

Ile Lys Asp Phe Leu Val Asn Gln Asp Arg Cys Ala Glu Val Thr Leu
                165                 170                 175

Glu Gly Gln Met Tyr Pro Gly Lys Gly Gly Ser Lys Glu Lys Asn
            180                 185                 190

Lys Thr Lys Pro Glu Lys Gly Lys Lys Glu Gly Asp Pro Lys Pro
        195                 200                 205

Arg Ala Ser Lys Glu Asp Asn Arg Ala Gly Ser Arg Arg Glu Asp Leu
    210                 215                 220

<210> SEQ ID NO 38
<211> LENGTH: 158
<212> TYPE: PRT
<213> ORGANISM: Xenopus laevis

<400> SEQUENCE: 38

Met Gly Arg Ser Arg Ser Arg Ser Pro Glu Arg Arg Glu Arg Arg
 1               5                  10                  15

Arg Ser Arg Ser Ala Ser Arg Glu Arg Glu Arg Arg Arg Glu Arg
            20                  25                  30

Ser Arg Ser Arg Glu Arg Arg Ser Arg Ser Arg Ser Pro His Arg
        35                  40                  45

Arg Arg Ser Arg Ser Pro Arg Arg His Arg Ser Ser Ile Ser Pro
    50                  55                  60

Ser Arg Leu Lys Asp Arg Arg Asp Asp Asp Lys Lys Glu Pro Lys Glu
 65                  70                  75                  80

Ser Lys Gly Gly Gly Ser Lys Glu Arg Gln Leu Ala Ala Glu Asp Leu
                 85                  90                  95

Glu Gly Lys Thr Glu Glu Ile Glu Met Met Lys Leu Met Gly Phe
            100                 105                 110

Ala Ser Phe Asp Ser Ser Lys Gly Lys Lys Thr Asp Gly Ser Val Asn
        115                 120                 125

Ala Tyr Ala Ile Asn Val Ser Gln Lys Arg Lys Tyr Arg Gln Tyr Met
    130                 135                 140

Asn Arg Lys Gly Gly Phe Asn Arg Pro Leu Asp Phe Val Ala
145                 150                 155

<210> SEQ ID NO 39
<211> LENGTH: 12
<212> TYPE: DNA
<213> ORGANISM: Artificial Sequence
```

-continued

<220> FEATURE:
<223> OTHER INFORMATION: sequence at shRNA target site in LRP6 shRNA-res construct

<400> SEQUENCE: 39
ctgaggtgta ac                                                                12